United States Patent
Arakawa et al.

(10) Patent No.: US 11,911,341 B2
(45) Date of Patent: Feb. 27, 2024

(54) MULTILAYER VESSEL, AND APPLICATION THEREOF

(71) Applicant: MITSUBISHI GAS CHEMICAL COMPANY, INC., Tokyo (JP)

(72) Inventors: Shota Arakawa, Kanagawa (JP); Toshiya Naito, Tokyo (JP); Satoshi Okada, Kanagawa (JP); Kenichiro Usuda, Kanagawa (JP); Takumi Toida, Niigata (JP); Haruka Okazaki, Tokyo (JP); Fumihiro Ito, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 1596 days.

(21) Appl. No.: 16/077,640

(22) PCT Filed: Feb. 15, 2017

(86) PCT No.: PCT/JP2017/005537
§ 371 (c)(1),
(2) Date: Aug. 13, 2018

(87) PCT Pub. No.: WO2017/141969
PCT Pub. Date: Aug. 24, 2017

(65) Prior Publication Data
US 2019/0070072 A1    Mar. 7, 2019

(30) Foreign Application Priority Data

Feb. 16, 2016  (JP) ............................ JP2016-026632
Dec. 6, 2016   (JP) ............................ JP2016-236445

(51) Int. Cl.
*A61J 1/14*  (2023.01)
*A61J 1/05*  (2006.01)
(Continued)

(52) U.S. Cl.
CPC ............. *A61J 1/1468* (2015.05); *A61J 1/05* (2013.01); *A61J 1/06* (2013.01); *A61M 5/3129* (2013.01);
(Continued)

(58) Field of Classification Search
CPC .. B32B 1/02; B32B 1/08; B32B 27/18; B32B 27/32; B32B 27/34; B32B 27/325;
(Continued)

(56) References Cited

U.S. PATENT DOCUMENTS

2004/0076781 A1* 4/2004 Kanda ................. C08G 69/265
                                                     428/35.7
2004/0230028 A1   11/2004 Sato et al.
(Continued)

FOREIGN PATENT DOCUMENTS

EP    2724860 A1    4/2014
JP    H08-127641 A  5/1996
(Continued)

OTHER PUBLICATIONS

Machine translation of Kanda et al. (JP 2004-351769 A), Kanda et al. was cited in Written Opinion dated Aug. 13, 2018 in U.S. Appl. No. 16/077,640 file.*
(Continued)

*Primary Examiner* — Lee E Sanderson
(74) *Attorney, Agent, or Firm* — GREENBLUM & BERNSTEIN, P.L.C.

(57) ABSTRACT

Provided is a multilayer vessel excellent in gas barrier performance and transparency and its application. The multilayer vessel contains a layer (X) that contains at least one type of polyolefin resin as the major ingredient; and a layer (Y) that contains a polyamide resin (A) as the major ingredient, the polyamide resin (A) being composed of a structural unit derived from diamine, and a structural unit derived
(Continued)

from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

26 Claims, 1 Drawing Sheet

(51) Int. Cl.
| | | |
|---|---|---|
| B65D 1/09 | (2006.01) | |
| B32B 27/32 | (2006.01) | |
| B32B 27/08 | (2006.01) | |
| B32B 27/34 | (2006.01) | |
| B32B 1/02 | (2006.01) | |
| B65D 1/00 | (2006.01) | |
| C08G 69/32 | (2006.01) | |
| A61J 1/06 | (2006.01) | |
| B32B 27/18 | (2006.01) | |
| A61M 5/31 | (2006.01) | |
| B29C 49/00 | (2006.01) | |
| B29C 49/06 | (2006.01) | |
| C08G 69/06 | (2006.01) | |
| C08G 69/26 | (2006.01) | |
| B29K 77/00 | (2006.01) | |
| B29L 31/00 | (2006.01) | |

(52) U.S. Cl.
CPC .......... *B29C 49/0005* (2013.01); *B29C 49/06* (2013.01); *B32B 1/02* (2013.01); *B32B 27/08* (2013.01); *B32B 27/18* (2013.01); *B32B 27/32* (2013.01); *B32B 27/325* (2013.01); *B32B 27/34* (2013.01); *B65D 1/00* (2013.01); *B65D 1/09* (2013.01); *C08G 69/06* (2013.01); *C08G 69/26* (2013.01); *C08G 69/32* (2013.01); *A61M 2005/3131* (2013.01); *A61M 2207/00* (2013.01); *B29C 2949/3032* (2022.05); *B29C 2949/3034* (2022.05); *B29K 2077/00* (2013.01); *B29L 2031/712* (2013.01); *B32B 2250/02* (2013.01); *B32B 2250/03* (2013.01); *B32B 2250/05* (2013.01); *B32B 2250/24* (2013.01); *B32B 2250/40* (2013.01); *B32B 2307/30* (2013.01); *B32B 2307/412* (2013.01); *B32B 2307/7244* (2013.01); *B32B 2439/80* (2013.01); *B32B 2535/00* (2013.01); *C08G 2390/00* (2013.01)

(58) Field of Classification Search
CPC ... B32B 27/327; B29C 45/0001; B29C 45/16; B29C 49/0005; B29C 49/06; A61J 1/1468; A61M 5/3129
See application file for complete search history.

(56) References Cited

U.S. PATENT DOCUMENTS

| | | | |
|---|---|---|---|
| 2012/0302723 A1* | 11/2012 | Oda ................. | C08L 77/06 528/324 |
| 2013/0065005 A1* | 3/2013 | Yamamoto .............. | C08J 3/226 524/879 |
| 2014/0106103 A1* | 4/2014 | Arakawa ............ | B29C 45/1642 428/36.8 |
| 2015/0298887 A1 | 10/2015 | Okada et al. | |
| 2015/0368023 A1 | 12/2015 | Kashiba et al. | |
| 2016/0046765 A1 | 2/2016 | Oda et al. | |
| 2018/0296437 A1* | 10/2018 | Arakawa ................. | G01N 1/10 |

FOREIGN PATENT DOCUMENTS

| | | | |
|---|---|---|---|
| JP | 2004-229750 A | | 8/2004 |
| JP | 2004-351769 A | | 12/2004 |
| JP | 2004-352985 A | | 12/2004 |
| JP | 2012-30556 A | | 2/2012 |
| JP | 2012-201412 A | | 10/2012 |
| JP | 2014-57632 A | | 4/2014 |
| JP | 2014-68767 A | | 4/2014 |
| JP | 2014057632 A | * | 4/2014 |
| JP | 2014-113305 A | | 6/2014 |
| JP | 2014-171554 A | | 9/2014 |
| WO | 2014/141978 A1 | | 9/2014 |

OTHER PUBLICATIONS

The product data sheet for Zeonex 5000 from Zeon Corporation available online at https://www.zeonex.com/downloads/datasheets/pharma ceuticals/ZEONEX_5000.pdf, p. 1. (Year: 2015).*
The product data sheet for Zeonex 690R from Zeon Corporation available online at https://www.zeonex.com/downloads/datasheets/pharmaceuticals /ZEONEX_690R.pdf (Year: 2015).*
International Search Report issued with respect to Patent Application No. PCT/JP2017/005537, dated Apr. 4, 2017.
International Preliminary Report on Patentability issued with respect to Patent Application No. PCT/JP2017/005537, dated Aug. 21, 2018.
Extended European Search Report, European Patent Office, Application No. 17753225.6, dated Sep. 23, 2019, 7 pages.

* cited by examiner

[Fig. 1]
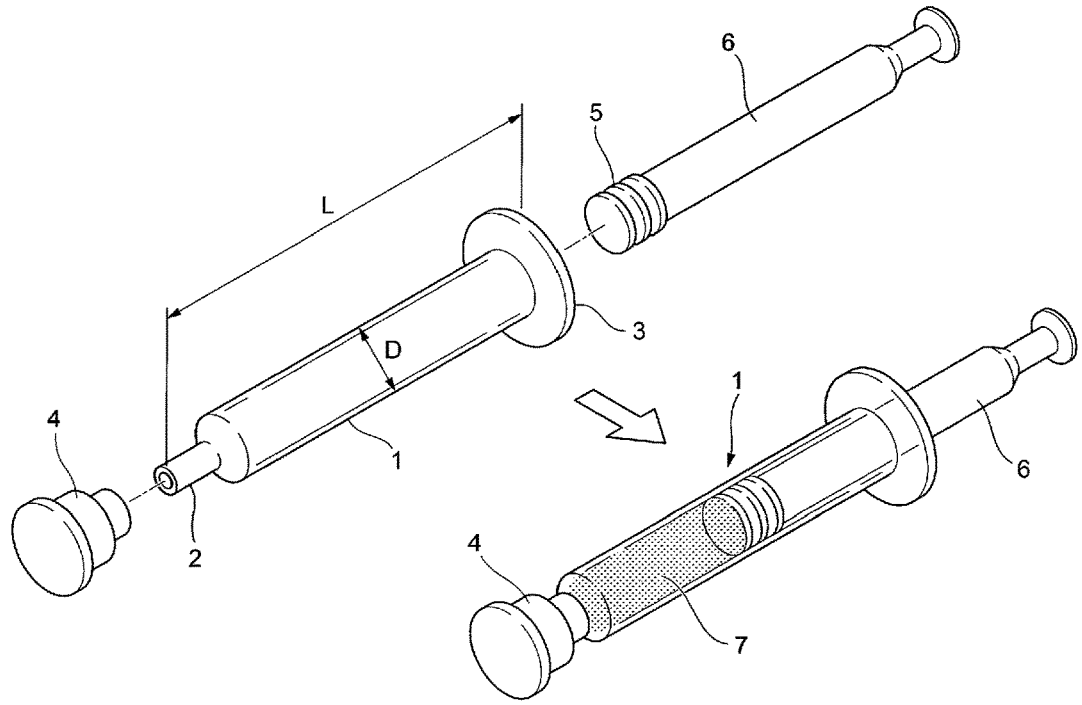
[Fig 2]
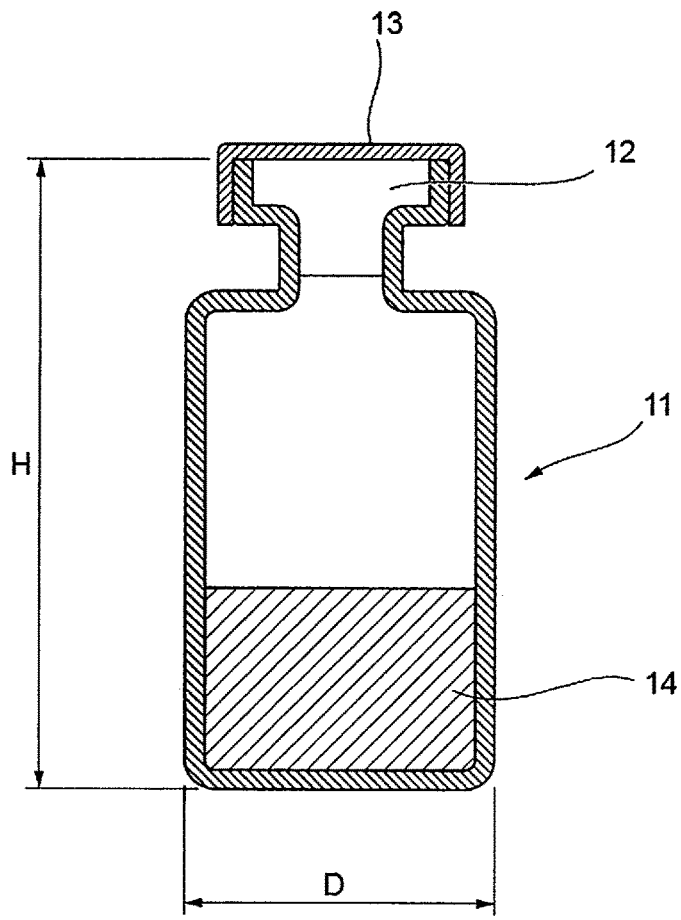

MULTILAYER VESSEL, AND APPLICATION THEREOF

TECHNICAL FIELD

This invention relates to a multilayer vessel, a syringe, a prefilled syringe, a multilayer body, a method for manufacturing a multilayer vessel, an article, a method for a storing a bio-pharmaceutical and a method for manufacturing the article. Particularly, it relates to a multilayer vessel for medical packaging.

BACKGROUND ART

Glass vessels in the forms of ampule, vial and prefilled syringe have been used as a medical packing vessel for storing chemicals filled therein in a sealed manner. These glass vessels, however, suffer from that they generate a fine vitreous substance called "flakes" when it used, and that they easily fractures upon impact caused by dropping or the like. Another disadvantage of the glass vessels is that the vessels per se are heavy due to a relatively large specific gravity of glass.

In contrast, plastic is lighter than glass, and some of them even excels in impact resistance, heat resistance and transparency, depending on their materials. Plastic vessels have therefore been investigated as a substitute for the glass vessels. For example, Patent Literature 1 discloses a medial vessel made of a polyester resin. Also cycloolefin polymer (occasionally be referred to as "COP", hereinafter) has widely been used as a substitute for glass materials in the field of medical vessel, by virtue of its high impact resistance, heat resistance and transparency.

Many of the plastic vessels are, however, inferior to the glass vessels in terms of gas barrier performance, which is desired to be improved. With the aim of improving the gas barrier property of plastic vessels, there has been investigated a multilayer vessel having a gas barrier layer as an intermediate layer. For example, Patent Literature 2 discloses a prefilled syringe whose innermost layer and outermost layer are made of a polyolefin resin, and whose intermediate layer is made of a resin with a high barrier performance.

Polymetaxylylene adipamide (occasionally be referred to as "N-MXD6", hereinafter) has been known as a thermoplastic resin with a high oxygen barrier performance (Patent Literatures 3 to 6). N-MXD6, however, very quickly crystallizes at 250 to 320° C., which is a temperature range for heat forming of the polyolefin resin such as COP. Hence, in some case when forming a multilayer vessel that uses N-MXD6 for the gas barrier layer and uses COP for the innermost layer and the outermost layer, the N-MXD6 layer would cause breakage, non-uniform thickness or blushing, resulting in degraded performances such as gas barrier performance and transparency, or deformation. It would also cause blushing after heat sterilization, damaging the transparency.

Known methods for suppressing N-MXD6 from causing blushing includes a method of adding a specific metal salt of aliphatic acid as a blushing inhibitor, and a method of adding a specific diamide compound or a diester compound. These methods for suppressing blushing with the aid of additives are known to be effective for a single-layered film which is brought into direct contact with water, or for an application associated with stretching, such as a multilayer stretched bottle with a layer structure of PET/N-MXD6/PET using polyethylene terephthalate (occasionally be referred to as "PET", hereinafter). However, as for a multilayer vessel with a layer structure of COP/N-MXD6/COP, an effect of suppressing blushing after heat sterilization is not satisfactory.

Other known methods include a method of adding a nucleation agent for crystallization to N-MXD6; and a method of blending a crystalline polyamide resin such as nylon 6, which acts as a nucleation agent for crystallization in the process of heat sterilization, with N-MXD6.

CITATION LIST

Patent Literature

[Patent Literature 1] JP-A-08-127641
[Patent Literature 2] JP-A-2004-229750
[Patent Literature 3] JP-A-2012-201412
[Patent Literature 4] JP-A-2012-30556
[Patent Literature 6] JP-A-2014-68767

SUMMARY OF INVENTION

Technical Problem

This invention is aimed at solving the above-described problems, and is to provide a multilayer vessel and multilayer body of material of the multilayer vessel with gas barrier performance and transparency suitable enough for medical packaging materials which are subject to heat sterilization.

Solution to Problem

The present inventors have extensively studied the multilayer vessel which excels both in gas barrier performance and transparency after heat sterilization, and found that excellent gas barrier performance and transparency could be achieved even after heat sterilization, by using a specific polyamide resin composition for the gas barrier layer. The finding led us to complete this invention.

That is, this invention relates to a multilayer vessel, a syringe, a prefilled syringe, a multilayer body, a method for manufacturing a multilayer vessel, an article, a method for a storing a bio-pharmaceutical and a method for manufacturing the article.

<1-1> A multilayer vessel comprising: a layer (X) that contains at least one type of polyolefin resin as the major ingredient; and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<1-2> The multilayer vessel of <1-1>, wherein the polyamide resin (A) contains calcium atom.

<1-3> The multilayer vessel of <1-2>, wherein the calcium atom contained in the polyamide resin (A) is derived from calcium hypophosphite.

<1-4> The multilayer vessel of any one of <1-1> to <1-3>, wherein the polyamide resin (A) contains 3 to 300 ppm by mass of phosphorus atom.

<1-5> The multilayer vessel of <1-1> or <1-3>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<1-6> The multilayer vessel of any one of <1-1> to <1-5>, wherein the polyolefin resin is at least one polymer selected from the group consisting of cycloolefin-based polymer and polypropylene-based polymer.

<1-7> The multilayer vessel of any one of <1-1> to <1-6>, wherein 30 to 60 mol % of the structural unit derived from dicarboxylic acid is an adipic acid-derived structural unit.

<1-8> The multilayer vessel of anyone of <1-1> to <1-7>, comprising at least three layers, whose inner layer and outer layer being the layer (X), and at least one of intermediate layers being the layer (Y).

<1-9> The multilayer vessel of any one of <1-1> to <1-8>, wherein the layer (Y) has a thickness that accounts for 2 to 40% of the total thickness of the multilayer vessel.

<1-10> The multilayer vessel of any one of <1-1> to <1-9>, being allowed for medical packaging.

<1-11> The multilayer vessel of <1-10>, being an ampule, vial, cartridge, or prefilled syringe.

<1-12> The multilayer vessel of any one of <1-1> to <1-11>, being an infusion vessel.

<1-13> A multilayer article comprising: a layer (X) that contains at least one type of polyolefin resin as the major ingredient, and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<1-14> The multilayer article of <1-13>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<1-15> A method for manufacturing a multilayer vessel that was described in any one of <1-1> to <1-12>, comprising molding based on injection blow molding.

<2-1> A multilayer vessel comprising: a layer (X) that contains the cycloolefin-based polymer (B) as the major ingredient, and a layer (Y) that contains the polyamide resin (A) as the major ingredient, wherein the polyamide resin (A) is composed of a structural unit derived from diamine and a structural unit derived from dicarboxylic acid, 70 mol % or more of the structural unit derived from diamine is derived from metaxylylenediamine, meanwhile 30 to 60 mol % of the structural unit derived from dicarboxylic acid is derived from a straight chain aliphatic α,ω-dicarboxylic acid having 4 to 20 carbon atoms, and 70 to 40 mol % is derived from isophthalic acid, the cycloolefin-based polymer (B) has a glass transition temperature of 50 to 170° C., the polyamide resin (A) has a glass transition temperature of 100 to 160° C., the cycloolefin-based polymer (B) shows a melt viscosity of 100 to 250 Pa·sec at one or more temperatures between 260 and 300° C., under a shear rate of 1216 sec$^{-1}$, and the polyamide resin (A) shows a melt viscosity of 200 to 400 Pa·sec at 270° C., under a shear rate 1216 sec$^{-1}$.

<2-2> The multilayer vessel of <2-1>, wherein the polyamide resin (A) contains calcium atom.

<2-3> The multilayer vessel of <2-2>, wherein the calcium atom contained in the polyamide resin (A) is derived from calcium hypophosphite.

<2-4> The multilayer vessel of any one of <2-1> to <2-3>, wherein the polyamide resin (A) contains 3 to 300 ppm by mass of phosphorus atom.

<2-5> The multilayer vessel of <2-1> or <2-3>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<2-6> The multilayer vessel of any one of <2-1> to <2-5>, which has a difference between the glass transition temperatures of the cycloolefin-based polymer (B) and the polyamide resin (A) of 70° C. or smaller.

<2-7> The multilayer vessel of any one of <2-1> to <2-6>, wherein 30 to 60 mol % of the structural unit derived from dicarboxylic acid is an adipic acid-derived structural unit.

<2-8> The multilayer vessel of anyone of <2-1> to <2-7>, comprising at least three layers, whose inner layer and outer layer being the layer (X), and at least one of intermediate layer(s) being the layer (Y).

<2-9> The multilayer vessel of any one of <2-1> to <2-8>, wherein the layer (Y) has a thickness that accounts for 2 to 40% of the total thickness of the multilayer vessel.

<2-10> The multilayer vessel of any one of <2-1> to <2-9>, being allowed for medical packaging.

<2-11> The multilayer vessel of <2-10>, being an ampule, vial, cartridge, or prefilled syringe.

<2-12> A multilayer vessel, or a multilayer article comprising: a layer (X) that contains at least one type of cycloolefin-based polymer as the major ingredient; and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid, wherein the cycloolefin-based polymer (B) has a glass transition temperature of 50 to 170° C., the polyamide resin (A) has a glass transition temperature of 100 to 160° C., the cycloolefin-based polymer (B) shows a melt viscosity of 100 to 250 Pa·sec at one or more temperatures between 260 and 300° C., under a shear rate of 1216 sec$^{-1}$, and the polyamide resin (A) shows a melt viscosity of 200 to 400 Pa·sec at 270° C., under a shear rate 1216 sec$^{-1}$.

<2-13> The multilayer vessel of <2-12>, wherein the polyamide resin contains 20 to 200 ppm by mass of phosphorus atom, and contains calcium atom so that the molar ratio given by (phosphorus atom):(calcium atom) will be 1:0.3 to 0.7.

<2-14> A method for manufacturing a multilayer vessel, the method comprising: molding a multilayer preform by individually injecting the layer (X) that contains the cycloolefin-based polymer (B) as the major ingredient, and the layer (Y) that contains the polyamide resin (A) as the major ingredient, to thereby form a multilayer preform; and, molding the multilayer preform by blow molding, wherein the polyamide resin (A) is composed of a structural unit derived from diamine and a structural unit derived from dicarboxylic acid, 70 mol % or more of the structural unit derived from diamine is derived from metaxylylenediamine, meanwhile 30 to 60 mol % of the structural unit derived from dicarboxylic acid is derived from a straight chain aliphatic α,ω-dicarboxylic acid having 4 to 20 carbon atoms, and 70 to 40 mol % is derived from isophthalic acid, the cycloolefin-based polymer (B) has a glass transition temperature of 50 to 170° C., the polyamide resin (A) has a glass transition temperature of 100 to 160° C., the cycloolefin-based polymer (B) shows a melt viscosity of 100 to 250 Pa·sec at one or more temperatures between 260 and 300° C., under a shear rate of 1216 sec$^{-1}$, and the polyamide resin (A) shows a melt viscosity of 200 to 400 Pa·sec at 270° C., under a shear rate 1216 sec$^{-1}$.

<2-15> The method for manufacturing a multilayer vessel of <2-14>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<3-1> A multilayer syringe barrel for prefilled syringe comprising a layer (X) that contains at least one type of cycloolefin-based polymer having a glass transition temperature of lower than 100° C. as the major ingredient; and a layer (Y) that contains a polyamide resin (A) as the major ingredient,
the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<3-2> The multilayer syringe barrel for prefilled syringe of <3-1>, wherein the polyamide resin (A) contains calcium atom.

<3-3> The multilayer syringe barrel for prefilled syringe of <3-2>, wherein the calcium atom contained in the polyamide resin (A) is derived from calcium hypophosphite.

<3-4> The multilayer syringe barrel for prefilled syringe of any one of <3-1> to <3-3>, wherein the polyamide resin (A) contains 3 to 300 ppm by mass of phosphorus atom.

<3-5> The multilayer syringe barrel for prefilled syringe of <3-1> or <3-3>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<3-6> The multilayer syringe barrel for prefilled syringe of any one of <3-1> to <3-5>, wherein the cycloolefin-based polymer having a glass transition temperature of lower than 100° C. has a glass transition temperature of 50 to 90° C.

<3-7> The multilayer syringe barrel for prefilled syringe of any one of <3-1> to <3-6>, wherein 30 to 60 mol % of the structural unit derived from dicarboxylic acid is an adipic acid-derived structural unit.

<3-8> The multilayer syringe barrel for prefilled syringe of any one of <3-1> to <3-7>, comprising at least three layers, whose inner layer and outer layer being the layer (X), and at least one of intermediate layer(s) being the layer (Y).

<3-9> A syringe comprising the multilayer syringe barrel for prefilled syringe described in any one of <3-1> to <3-8>.

<3-10> A prefilled syringe comprising the syringe described in <3-9>, and a chemical liquid filled in the syringe.

<4-1> A multilayer syringe barrel for prefilled syringe comprising: a layer (X) that contains at least one polymer selected from polypropylene-based polymer and cycloolefin-based polymer having a glass transition temperature of 100° C. or higher as the major ingredient, and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<4-2> The multilayer syringe barrel for prefilled syringe of <4-1>, wherein the polyamide resin (A) contains calcium atom.

<4-3> The multilayer syringe barrel for prefilled syringe of <4-2>, wherein the calcium atom contained in the polyamide resin (A) is derived from calcium hypophosphite.

<4-4> The multilayer syringe barrel for prefilled syringe of any one of <4-1> to <4-3>, wherein the polyamide resin (A) contains 3 to 300 ppm by mass of phosphorus atom.

<4-5> The multilayer syringe barrel for prefilled syringe of <4-1> or <4-3>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<4-6> The multilayer syringe barrel for prefilled syringe of any one of <4-1> to <4-5>, wherein the layer (X) contains, as the major ingredient, at least one polymer selected from cycloolefin-based polymer.

<4-7> The multilayer syringe barrel for prefilled syringe of any one of <4-1> to <4-6>, wherein 30 to 60 mol % of the structural unit derived from dicarboxylic acid is an adipic acid-derived structural unit.

<4-8> The multilayer vessel of any one of <4-1> to <4-7>, comprising at least three layers, whose inner layer and outer layer being the layer (X), and at least one of intermediate layer(s) being the layer (Y).

<4-9> A syringe comprising the multilayer syringe barrel for prefilled syringe described in any one of <4-1> to <4-8>.

<4-10> A prefilled syringe comprising the syringe described in <4-9>, and a chemical liquid filled in the syringe.

<5-1> A multilayer vessel comprising: a layer (X) that contains at least one type of polyolefin resin as the major ingredient, an adhesive layer, and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<5-2> The multilayer vessel of any one of <5-1>, wherein the polyamide resin (A) contains calcium atom.

<5-3> The multilayer vessel of <5-2>, wherein the calcium atom contained in the polyamide resin (A) is derived from calcium hypophosphite.

<5-4> The multilayer vessel of any one of <5-1> to <5-3>, wherein the polyamide resin (A) contains 3 to 300 ppm by mass of phosphorus atom.

<5-5> The multilayer vessel of <5-1> or <5-3>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<5-6> The multilayer vessel of any one of <5-1> to <5-5>, wherein the layer (X) contains at least one type of polypropylene-based polymer as the major ingredient.

<5-7> The multilayer syringe barrel for prefilled syringe of any one of <5-1> to <5-6>, wherein 30 to 60 mol % of the structural unit derived from dicarboxylic acid is an adipic acid-derived structural unit.

<5-8> The multilayer vessel of <5-1> and <5-7>, comprising at least five layers, whose inner layer and outer layer being the layer (X), and at least one of intermediate layers being the layer (Y).

<5-9> The multilayer vessel of any one of <5-1> to <5-8>, being a bio-pharmaceutical vessel for storing a protein-derived medicinal component.

<5-10> The multilayer vessel of any one of <5-1> to <5-8>, being an infusion vessel.

<5-11> A multilayer article comprising: a layer (X) that contains at least one type of polyolefin resin as the major ingredient, an adhesive layer, and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<5-12> The multilayer article of <5-11> and claim 18, wherein the polyamide resin (A) contains 20 to 200 ppm by mass of phosphorus atom, and contains calcium atom so that the molar ratio given by (phosphorus atom):(calcium atom) will be 1:0.3 to 0.7.

<6-1> A bio-pharmaceutical vessel comprising: a layer (X) that contains at least one type of polyolefin resin as the major ingredient, and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<6-2> The bio-pharmaceutical vessel of <6-1>, wherein the polyamide resin (A) contains calcium atom.

<6-3> The bio-pharmaceutical vessel of <6-2>, wherein the calcium atom contained in the polyamide resin (A) is derived from calcium hypophosphite.

<6-4> The bio-pharmaceutical vessel of any one of <6-1> to <6-3>, wherein the polyamide resin (A) contains 3 to 300 ppm by mass of phosphorus atom.

<6-5> The bio-pharmaceutical vessel of <6-1> or <6-3>, wherein the polyamide resin (A) contains 20 to 200 ppm by mass of phosphorus atom, and contains calcium atom so that the molar ratio given by (phosphorus atom):(calcium atom) will be 1:0.3 to 0.7.

<6-6> The bio-pharmaceutical vessel of any one of <6-1> to <6-5>, wherein the polyolefin resin is at least one polymer selected from the group consisting of cycloolefin-based polymer and polypropylene-based polymer.

<6-7> The bio-pharmaceutical vessel of any one of <6-1> to <6-6>, wherein 30 to 60 mol % of the structural unit derived from dicarboxylic acid is an adipic acid-derived structural unit.

<6-8> The bio-pharmaceutical vessel of any one of <6-1> to <6-7>, comprising at least three layers, whose inner layer and outer layer being the layer (X), and at least one of intermediate layer(s) being the layer (Y).

<6-9> The bio-pharmaceutical vessel of any one of <6-1> to <6-8>, wherein the layer (Y) has a thickness that accounts for 2 to 40% of the total thickness of the multilayer vessel.

<6-10> The bio-pharmaceutical vessel of any one of <6-1> to <6-9>, being a vial.

<6-11> The bio-pharmaceutical vessel of any one of <6-1>~<6-10>, wherein the protein-derived medicinal component is selected from the group consisting of antibody, hormone, enzyme, and complexes containing them.

<6-12> An article comprising the bio-pharmaceutical vessel that was described in any one of <6-1> to <6-11>, and a bio-pharmaceutical contained in the bio-pharmaceutical vessel.

<6-13> A method for storing a bio-pharmaceutical that contains a protein-derived medicinal component using a vessel, the vessel comprising: a layer (X) that contains at least one type of polyolefin resin as the major ingredient, and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<6-14> The method for storing a bio-pharmaceutical of <6-13>, wherein the vessel is the bio-pharmaceutical vessel described in any one of <6-2> to <6-10>.

<6-15> The method for storing a bio-pharmaceutical of <6-13> or <6-14>, wherein the protein-derived medicinal component is selected from the group consisting of antibody, hormone, enzyme, and complexes containing them.

<6-16> A method for manufacturing an article having a vessel and a bio-pharmaceutical contained therein, the method comprising enclosing a bio-pharmaceutical that contains a protein-derived medicinal component, the vessel comprising: a layer (X) that contains at least one type of polyolefin resin as the major ingredient, and a layer (Y) that contains a polyamide resin (A) as the major ingredient, the polyamide resin (A) being composed of a structural unit derived from diamine, and a structural unit derived from dicarboxylic acid, 70 mol % or more of the structural unit derived from diamine being derived from metaxylylenediamine, meanwhile 30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid.

<6-17> The manufacturing method of <6-16>, wherein the vessel is a bio-pharmaceutical vessel described in any one of <6-2> to <6-10>.

<6-18> The manufacturing method of <6-16> or <6-17>, wherein the protein-derived medicinal component is selected from the group consisting of antibody, hormone, enzyme, and complexes containing them.

The embodiments which are the combination of at least two of the above <1-1>~<6-18> are contained in the present invention.

Advantageous Effects of Invention

The multilayer vessel of this invention keeps excellent gas barrier performance and transparency even after heat treatment. The multilayer vessel of this invention is therefore suitable for medical packaging vessel which needs to be sterilized by heating. In addition, the multilayer vessel of this invention can keep high transparency like glass vessels even after heat sterilization, and can therefore serve the customer's convenience as a substitute for the glass vessels.

BRIEF EXPLANATION OF THE DRAWINGS

FIG. 1 Schematic drawing showing an example of a prefilled syringe according to this invention.
FIG. 2 Schematic drawing showing an example of a vessel for bio-pharmaceutical according to this invention.

DESCRIPTION OF EMBODIMENTS

This invention will be detailed below. Note that all numerical ranges given in this specification, using "to" preceded and succeeded by numerals, are used to represent the ranges including these numerals respectively as the lower and upper limit values.

The multilayer vessel of this invention includes a layer (X) that contains at least one type of polyolefin resin as the major ingredient; and a layer (Y) that contains a polyamide resin (A) as the major ingredient. The polyamide resin (A) is composed of a structural unit derived from diamine, and a structural unit derived from dicarboxylic acid, where 70 mol % or more of the structural unit derived from diamine is derived from metaxylylenediamine, meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid.

The polyamide resin (A) is typically an amorphous polyamide resin. By using such polyamide resin, the resultant multilayer vessel will have excellent gas barrier performance and transparency even after heat sterilization. This multilayer vessel will occasionally be referred to as "basic mode multilayer vessel", hereinafter.

The amorphous polyamide resin is now defined to be a resin showing no definite melting point, and more specifically has a crystal melting enthalpy ΔHm of smaller than 5 J/g, which is more preferably 3 J/g or smaller, and even more preferably 1 J/g or smaller.

<Layer Structure>

Layer structure of the multilayer vessel in the basic mode of this invention is not specifically limited. The number and types of the layer (X) and the layer (Y) are not specifically limited.

The multilayer vessel is preferably composed of at least 3 layers, more preferably 3 to 10 layers, and even more preferably 3 to 5 layers.

The multilayer vessel preferably has 1 to 5 layers (X), and more preferably 2 to 4 layers (X). The multilayer vessel preferably has 1 to 3 layers (Y), and more preferably 1 or 2 layers (Y).

For example, the multilayer vessel may have one layer (X) and one layer (Y) to form a X/Y structure (the layer (X) for the inner layer) or a Y/X structure (the layer (Y) for the inner layer); or may have two layers (X) and one layer (Y) to form a three-layered X/Y/X structure. Still alternatively, the multilayer vessel of this invention may have the layer (X) and the layer (Y) that are brought into contact, or may have an optional layer such as an adhesive layer (AD).

The multilayer vessel of this invention preferably has the layers (X) as the inner layer and the outer layer, and has the layer (Y) as at least one of intermediate layer (X/Y/X structure). In this embodiment, each of the layers (X) that serves as the inner layer or the outer layer may be brought into contact with the layer (Y) that serves as the intermediate layer (X/Y/X), or the layer (Y) and each of the layer (X) may be adhered while placing the adhesive layer (AD) in between (X/AD/Y/AD/X). This invention is, however, not limited to these structures, allowing usage of various thermoplastic resin layers depending on purposes.

Now the inner layer is defined by a layer which resides inside of the layer (Y) as one intermediate layer, out of the layers that compose the multilayer vessel, meanwhile the outer layer is defined by a layer which resides outside of the layer (Y) as one intermediate layer, out of the layers that compose the multilayer vessel. The inner layer and the outer layer may be the innermost layer and the outermost layer, respectively, or may have additional innermost layer and outermost layer.

<Layer (X)>

The layer (X) that composes the multilayer vessel according to the basic mode of this invention contains at least one type of polyolefin resin as the major ingredient, and typically serves as a water vapor barrier layer. Now, "has . . . polyolefin resin as the major ingredient" means that the polyolefin resin (water vapor barrier polymer) accounts for 70% by mass or more of the layer (X), which is more preferably 80% by mass or more, and even more preferably 90 to 100% by mass. The layer (X) may contain only one type, or two or more types, of polyolefin resins. When two or more types are contained, the total content of the polyolefin resins falls within the above described ranges.

Besides the polyolefin resin, the layer (X) may contain an additive such as antioxidant, matting agent, weathering stabilizer, UV absorber, crystal nucleating agent, plasticizer, flame retardant, antistatic agent or the like, depending on desired performances, but without adversely affecting the effects of the invention.

The multilayer vessel of this invention may have a plurality of layers (X), wherein the structure of such plurality of layers (X) may be same with, or different from each other. The layer (X) is preferably, but not restrictively, 20 to 2000 μm thick from the viewpoint of strength and cost, and is more preferably 50 to 1500 μm thick.

<<Polyolefin Resin>>

The polyolefin resin used in this invention is not specifically limited, for which any of known polyolefin resins are employable. The polyolefin resin is specifically exemplified by those described in paragraphs [0101] to [0103] of JP-A-2014-068767, the contents of which are incorporated into this specification.

The polyolefin resin is preferably COP, COC or polypropylenes (PP). COP and COC are preferable since they have chemical properties such as heat resistance and light resistance, are chemical resistance expectable from polyolefin resin; and has physical properties such as mechanical characteristics, melting characteristics, fluidity characteristics, and dimensional accuracy expectable from amorphous resin. Meanwhile, PP is preferable from the viewpoint of oil resistance.

COP is a polymer obtained typically by ring-opening polymerization of norbornene, followed by hydrogenation. COP is described for example in JP-A-H05-317411, and commercially available as ZEONEX (registered trademark) or ZEONOR (registered trademark) from ZEON Corporation, and as Daikyo Resin CZ (registered trademark) from Daikyo Seiko Ltd.

COC is typically a copolymer originated from olefins such as norbornene and ethylene; or a copolymer originated from olefins such as tetracyclododecene and ethylene. COC is commercially available as APEL (registered trademark) from Mitsui Chemicals, Inc.

For PP, any of known polymers such as propylene homopolymer, propylene-ethylene block copolymer, and propylene-ethylene random copolymer are employable. PP is commercially available, for example, as Bormed RB845MO from Borealis AG.

<Layer (Y)>

The layer (Y) that composes the multilayer vessel according to the basic mode of this invention contains at least one type of predetermined polyamide resin (A) as the major ingredient, and typically serves as a gas barrier layer.

The layer (Y) typically acts to cut off oxygen that tends to enter the vessel from the outside, and to prevent content of the vessel from being oxidized and degraded. From the viewpoint of good gas barrier performance, the layer (Y) preferably shows an oxygen transmission coefficient of 1.0 mL·mm/(m$^2$·day·atm) or less when measured in an environment at 23° C. with a relative humidity of 60%, which is more preferably 0.05 to 0.8 mL·mm/(m$^2$·day·atm). The oxygen transmission coefficient may be measured in accordance with ASTM D3985, typically by using "OX-TRAN (registered trademark) 2/61" (from MOCON Inc.).

Now, "contains . . . as the major ingredient" means that, the polyamide resin (A) (gas barrier polymer) accounts for 70 to 100% by mass of the layer (Y), which is more preferably 80 to 100% by mass, even more preferably 90 to 100% by mass, yet more preferably 95 to 100% by mass, and furthermore preferably 98 to 100% by mass. The layer (Y) may contain only one type, or two or more types, of the polyamide resins (A). When two or more types are contained, the total content of the polyamide resins (A) falls within the above-described ranges.

The multilayer vessel of this invention may have a plurality of the layers (Y), wherein such plurality of layers (Y) may be same with, or different from each other. The layer is preferably, but not restrictively, 1 to 800 µm thick from the viewpoint of gas barrier performance, transparency and cost, which is more preferably 100 to 700 µm. The thickness of the layer (Y) in the multilayer vessel of this invention preferably accounts for 2 to 40% of the total thickness of the multilayer vessel, from the viewpoint of gas barrier performance, transparency and cost, which is more preferably 5 to 38%, and even more preferably 10 to 35%. The thickness of the layer (Y) in the multilayer vessel may be measured by cutting the vessel, and by peeling off the layer (Y) from the layer (X). For the case where two or more layers (Y) are used, the total thickness is calculated as the thickness of layer (Y).

Besides the polyamide resin (A), the layer (Y) may contain an additive, depending on desired performances, but without adversely affecting the effects of the invention. The additive is specifically exemplified by pigment (inorganic pigment, etc.), lubricant (sodium stearate, calcium stearate, etc.), matting agent, heat stabilizer (antioxidant, more preferably phosphorus-containing antioxidant, etc.), weathering stabilizer, UV absorber, crystal nucleating agent, plasticizer, flame retardant, antistatic agent, anticoloring agent, and antigelling agent. A single additive may be used, or two or more additives may be used in a combined manner. The content of additive in the layer (Y) is preferably 10% by mass or less, and more preferably 5% by mass or less, which is variable depending on types of the additive. As for details of the additive, descriptions in paragraphs [0071] to [0099] of JP-A-2014-068767 may be referred to, the contents of which are incorporated by reference into this specification.

Preferred embodiments of the layer (Y) in this invention are exemplified by below:

(1) a layer composed substantially solely of one type, or two or more types, of polyamide resins (A);
(2) a layer composed substantially solely of one type, or two or more types of polyamide resins (A), and a polyamide resin other than the polyamide resin (A);
(3) a layer composed substantially solely of one type, or two or more types of polyamide resins (A), and an antioxidant;
(4) a layer composed solely of one type, or two or more types of polyamide resins (A), a polyamide resin other than the polyamide resin (A), and an antioxidant;
(5) a layer composed solely of one type, or two or more types of polyamide resins (A), and a lubricant;
(6) a layer composed solely of one type, or two or more types of polyamide resins (A), a polyamide resin other than the polyamide resin (A), and a lubricant;
(7) a layer composed solely of one type, or two or more types of polyamide resins (A), an antioxidant, and a lubricant;
(8) a layer composed solely of one type, or two or more types of polyamide resins (A), a polyamide resin other than the polyamide resin (A), an antioxidant, and a lubricant; and
(9) the aforementioned layers wherein the polyamide resin other than the polyamide resin (A) is an amorphous polyamide resin.

<<Polyamide Resin (A)>>

The polyamide resin (A) used in this invention is composed of a structural unit derived from diamine and a structural unit derived from dicarboxylic acid, wherein 70 mol % or more of the structural unit derived from diamine is derived from metaxylylenediamine; meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid. The polyamide resin (A) used in this invention is an amorphous resin. By using the amorphous resin, the transparency may be improved. The polyamide resin (A) used in this invention also excels in barrier performance after heat sterilization.

The polyamide resin (A) used in this invention preferably contains calcium atom. By containing calcium atom, the transparency after heat treatment may further be improved.

The polyamide resin (A) used in this invention preferably contains 20 to 200 ppm by mass of phosphorus atom, and contains calcium atom so that the molar ratio given by (phosphorus atom):(calcium atom) will be 1:0.3 to 0.7. With such design, the obtainable multilayer vessel will have still higher transparency after heat treatment, and a still lower YI value (yellowness index) after heat treatment. Calcium atom is preferably derived from calcium hypophosphite.

In some cases, the polyamide resin synthesized from metaxylylenediamine, the straight chain aliphatic α,ω-dicarboxylic acid having 4 to 20 carbon atoms, and isophthalic acid will have high yellowness index. One possible measure might be addition of a phosphorus-containing compound as an anticoloring agent in the process of polycondensation. However, when ratio of isophthalic acid reaches 40 mol % or more of the total dicarboxylic acids that compose the structural unit derived from dicarboxylic acid, and when using sodium hypophosphite which is widely used as the phosphorus-containing compound, the transparency was occasionally found to degrade, despite improvement in the yellowness index. When sodium hypophosphite was used, the obtained polyamide resin would be transparent, but was found to degrade the transparency after immersion in water. From further investigations, the present inventors also found that the transparency (haze) was further improved, and remained improved even after immersion in water, by adding, as the phosphorus-containing compound, calcium hypophosphite rather than sodium hypophosphite. Calcium salt, such as calcium hypophosphite, however less soluble in the straight chain aliphatic α,ω-dicarboxylic acid having 4 to 20 carbon atoms or in isophthalic acid, so that a white foreign matter would be occasionally found to occur under an increased amount of addition of calcium salt. Based on these findings, this invention succeeded in providing a polyamide resin that further excels in transparency, by presetting the ratio of phosphorus atom and calcium atom in the polyamide resin, and in further improving the transparency of the multilayer vessel.

In this invention, 70 mol % or more of the structural unit derived from diamine is derived from metaxylylenediamine. As for the structural unit derived from diamine, preferably 80 mol % or more, more preferably 90 mol % or more, even more preferably 95 mol % or more, yet more preferably 98 mol % or more, and furthermore preferably 99 mol % or more thereof is derived from metaxylylenediamine.

Diamines other than metaxylylenediamine are exemplified by aromatic diamines such as paraphenylenediamine and paraxylylenediamine; and aliphatic diamines such as 1,3-bis(aminomethyl)cyclohexane, 1,4-bis(aminomethyl) cyclohexane, tetramethylenediamine, pentamethylenediamine, hexamethylenediamine, octamethylenediamine and nonamethylenediamine. Only one type, or two or more types, of these other diamines may be used.

In this invention, 30 to 60 mol % of the structural unit derived from dicarboxylic acid is derived from the straight chain aliphatic α,ω-dicarboxylic acid having 4 to 20 carbon atoms, and 70 to 40 mol % is derived from isophthalic acid.

Of the whole dicarboxylic acid that composes the structural unit derived from dicarboxylic acid, the lower limit value of ratio of isophthalic acid is preferably 41 mol % or above, more preferably 43 mol % or above, and even more preferably 45 mol % or above. The upper limit value of ratio of isophthalic acid is preferably 68 mol % or below, and more preferably 66 mol % or below. Within these ranges, the multilayer vessel will tend to have a further reduced haze after heat treatment, which is preferable.

Of the whole dicarboxylic acid that composes the structural unit derived from dicarboxylic acid, the lower limit value of ratio of straight chain aliphatic α,ω-dicarboxylic acid having 4 to 20 carbon atoms is preferably 32 mol % or above, and more preferably 34 mol % or above. The upper limit value of ratio of straight chain aliphatic dicarboxylic acid having 4 to 20 carbon atoms is preferably 59 mol % or below, more preferably 57 mol % or below, and even more preferably 55 mol % or below. Within these ranges, the multilayer vessel will tend to have a further improved oxygen barrier performance, in particular, oxygen barrier performance after heat treatment.

The straight chain aliphatic α,ω-dicarboxylic acid having 4 to 20 carbon atoms is exemplified by aliphatic dicarboxylic acids such as succinic acid, glutaric acid, pimelic acid, suberic acid, azelaic acid, adipic acid, sebacic acid, undecanedioic acid and dodecanedioic acid; among them adipic acid and sebacic acid are preferable, and adipic acid is more preferable. Only one type, or two or more types, of the straight chain aliphatic α,ω-dicarboxylic acids having 4 to 20 carbon atoms may be used.

Of the whole dicarboxylic acid that composes the structural unit derived from dicarboxylic acid, the ratio of total of isophthalic acid and the straight chain aliphatic α,ω-dicarboxylic acid having 4 to 20 carbon atoms is preferably 90 mol % or above, more preferably 95 mol % or above, even more preferably 98 mol % or above, and may even be 100 mol %. Within these ranges, the multilayer vessel will tend to have an improved transparency, and a reduced yellowness index.

The dicarboxylic acid other than isophthalic acid and the straight chain aliphatic α,ω-dicarboxylic acid having 4 to 20 carbon atoms is exemplified by terephthalic acid, 2,6-naphthalenedicarboxylic acid, and alicyclic dicarboxylic acids having 6 to 12 carbon atoms. Specific examples include 1,4-cyclohexanedicarboxylic acid, and 1,3-cyclohexanedicarboxylic acid.

The polyamide resin (A) used in this invention is composed of the structural unit derived from dicarboxylic acid and the structural unit derived from diamine, but can contain additional structural unit other than the structural unit derived from dicarboxylic acid and the structural unit derived from diamine, and other moieties such as terminal group. The additional structural unit is exemplified by, but not limited to, lactams such as ε-caprolactam, valorolactam, laurolactam and undecalactam; and structural units derived from aminocarboxylic acids such as 11-aminoundecanoic acid and 12-aminododecanoic acid. The polyamide resin (A) used in this invention can also contain a trace component such as additives used for the synthesis. In the polyamide resin (A) used in this invention, the structural unit derived from dicarboxylic acid or the structural unit derived from diamine typically accounts for 95% by mass or more, and preferably accounts for 98% by mass or more.

As described above, the polyamide resin (A) used in this invention preferably contains 3 to 300 ppm by mass of phosphorus atom, which is more preferably 4 to 250 ppm by mass, and even more preferably 20 to 200 ppm by mass. The polyamide resin (A) also preferably contains calcium atom so that the molar ratio given by (phosphorus atom):(calcium atom) will be 1:0.3 to 0.7.

The lower limit value of phosphorus atom concentration in the polyamide resin (A) used in this invention is preferably 3 ppm by mass or above, more preferably 4 ppm by mass or above, even more preferably 20 ppm by mass or above, yet more preferably 22 ppm by mass or above, may even be 50 ppm by mass or above, furthermore preferably 100 ppm by mass or above, and particularly 150 ppm by mass or above. By increasing the phosphorus atom concentration in the polyamide resin (A), it now becomes possible to more effectively reduce the yellowness index (YI value). The upper limit value of phosphorus atom concentration is preferably 300 ppm by mass or below, more preferably 250 ppm by mass or below, even more preferably 230 ppm by mass or below, yet more preferably 200 ppm by mass or below, furthermore preferably 190 ppm by mass or below, particularly 180 ppm by mass or below, even may be 100 ppm by mass or below, still may be 50 ppm by mass or below, and again may be 30 ppm by mass or below. With the phosphorus atom concentration in the polyamide resin controlled to the lower limit value or above, the multilayer vessel will have small yellowness index, and an improved hue. Meanwhile, with the phosphorus atom concentration in the polyamide resin controlled to the upper limit value or below, the obtainable multilayer vessel will tend to have an improved transparency.

In the polyamide resin (A) used in this invention, the molar ratio given by (phosphorus atom):(calcium atom) is preferably 1:0.3 to 0.7, more preferably 1:0.4 to 0.6, even more preferably 1:0.45 to 0.55, and particularly 1:0.48 to 0.52. Each of phosphorus atom and calcium atom contained in the polyamide resin (A) used in this invention is preferably derived from calcium hypophosphite. With the molar ratio given by (phosphorus atom):(calcium atom) in the polyamide resin controlled to the lower limit value or above, the obtainable multilayer vessel will tend to have a further reduced haze. Meanwhile with the molar ratio given by (phosphorus atom):(calcium atom) in the polyamide resin controlled to the upper limit value or below, the obtainable multilayer vessel will tend to have a further reduced haze.

Methods for measuring the phosphorus atom concentration and the calcium atom concentration follow the methods described later in EXAMPLES. Note that instruments, etc. used in EXAMPLES are no more available due to discontinuation or other reasons, other equivalent instruments will suffice. The same will apply to other methods for measurement.

<<<Physical Properties of Polyamide Resin (A)>>>

The degree of polymerization of the polyamide resin is commonly indexed by relative viscosity. The relative viscosity of the polyamide resin (A) used in this invention is preferably 1.5 to 3.0, from the viewpoint of melt viscosity of the layer (X) and co-injection moldability. The lower limit value of relative viscosity is preferably 1.6 or above, more preferably 1.8 or above, and particularly preferably 1.9 or above. The upper limit value of relative viscosity is preferably 2.8 or below, more preferably 2.5 or below, even more preferably 2.3 or below, and yet more preferably 2.0 or below. Within these ranges, the co-injection moldability will be improved, and the obtained multilayer vessel will have high interlayer adhesiveness.

Now the relative viscosity in this context is measured by dissolving 0.2 g of precisely weighed polyamide resin in 20 mL of a 96% by mass aqueous sulfuric acid solution at 25° C. under stirring for thorough dissolution, immediately sampling 5 mL of the solution into a viscometer, allowing it to stand in a thermostat chamber at 25° C. for 10 minutes, and measuring the drop time (t). Also drop time (t0) of the 96% by mass aqueous sulfuric acid solution per se is measured in the same way. The relative viscosity is calculated using t and t0, based on the equation below. In more details, follow the method described later in EXAMPLES.

Relative viscosity=t/t0

<<<Method for Manufacturing Polyamide Resin (A)>>>

Next, an exemplary method for manufacturing the polyamide resin (A) used in this invention will be described. The polyamide resin (A) used in this invention is preferably, but of course not restrictively, a polyamide resin manufactured by the method described below.

The method for manufacturing the polyamide resin (A) used in this invention includes polycondensing the diamine and the dicarboxylic acid in the presence of a hypophosphite salt (for example, sodium hypophosphite and/or calcium hypophosphite, preferably calcium hypophosphite), wherein 70 mol % or more of the diamine is metaxylylenediamine; meanwhile 30 to 60 mol % of the dicarboxylic acid is a straight chain aliphatic α,ω-dicarboxylic acid having 4 to 20 carbon atoms, and 70 to 40 mol % is isophthalic acid.

In particular, as a result of synthesis in the presence of calcium hypophosphite, the obtainable polyamide resin will have a predetermined level of phosphorus atom concentration, a further reduced yellowness index, and, a predetermined range of calcium atom concentration, which further improves the transparency. Now, apart or the entire hypophosphite salt will be converted into phosphite salt (calcium phosphite, for example), phosphate salt (calcium phosphate, for example), polyphosphate salt (calcium polyphosphate, for example) or the like, due to oxidation during polycondensation or secondary process. The ratio will vary depending on polycondensation conditions or oxygen concentration during polycondensation. Hence, there would be the case where the polyamide resin (A) used in this invention contains calcium atom and phosphorus atom, but absolutely no calcium hypophosphite.

The polycondensation is typically melt polycondensation, wherein preferable is a method by which a starting diamine is added dropwise into a molten starting dicarboxylic acid under pressure and heating, so as to allow the mixture to polycondensate while removing water released as a result of condensation; or, a method by which a salt composed of a starting diamine and a starting dicarboxylic acid is heated under pressure in the presence of water, and the melt is allowed to polymerize while removing the added water, and water released as a result of condensation.

In this invention, hypophosphite salt (for example, sodium hypophosphite and/or calcium hypophosphite, preferably calcium hypophosphite) is preferably added, so that the phosphorus atom concentration in the polyamide resin (A) will be 3 to 300 ppm by mass. A more preferable range is same as the above-described range in which the ratio of phosphorus atom in the polyamide resin (A) falls.

In the process of polycondensation, it is also preferable to add other alkali metal compound, to be used in combination with the hypophosphite salt (for example, sodium hypophosphite and/or calcium hypophosphite, preferably calcium hypophosphite). By adding the alkali metal compound, it now becomes possible to control the rate of amidation. The alkali metal compound is exemplified by sodium acetate. When the alkali metal compound is added, the molar ratio given by (alkali metal compound)/(hypophosphite salt) (for example, sodium hypophosphite and/or calcium hypophosphite, preferably calcium hypophosphite) is preferably 0.5 to 2.0.

As for other polymerization conditions, descriptions in JP-A-2015-098669 and International Publication WO2012/140785 pamphlet may be referred to, the contents of which are incorporated by reference into this specification.

Details of the diamine, dicarboxylic acid and so forth are same as those described in the paragraphs above regarding the polyamide resin. The same will apply to preferable ranges.

The layer (Y) in this invention may contain a polyamide resin other than the polyamide resin (A). The polyamide resin other than the polyamide resin (A) may be an amorphous resin or may be a crystalline resin. Amorphous resin is preferable.

The layer (Y) in this invention may alternatively be designed so as to contain substantially no polyamide resin other than the polyamide resin (A). The phrase "to contain substantially no . . . " means, for example, that the content of the polyamide resin other than the polyamide resin (A) in the layer (Y) is 1% by mass or less of the polyamide resin (A).

<Optional Layer>

Besides the layer (X) and the layer (Y), the multilayer vessel according to the basic mode of this invention may contain an optional layer depending on desired performances. The optional layer is exemplified by the adhesive layer described above.

<<Adhesive Layer>>

In multilayer vessel according to the basic mode of this invention, an adhesive layer is preferably provided between these two adjoining layers, if the adhesion strength between these two adjoining layers is below a practical level.

The adhesive layer preferably contains an adhesive thermoplastic resin. The adhesive thermoplastic resin is exemplified by acid-modified polyolefin resins that are composed of polyolefin resins such as polyethylene or polypropylene, modified with an unsaturated carboxylic acid such as acrylic acid, methacrylic acid, maleic acid, maleic anhydride, fumaric acid or itaconic acid; and, polyester-based thermoplastic elastomers that contain polyester-based block copolymer as the major ingredient. The adhesive layer preferably uses a product obtained by modifying a resin same as, or equivalent to, the resin used for the layer (X), from the viewpoint of adhesiveness.

The adhesive layer is preferably 2 to 100 μm thick from the viewpoint of exhibiting a practical level of adhesion strength, and keeping a good moldability, which is more preferably 5 to 90 μm thick, and even more preferably 10 to 80 μm thick.

<Physical Properties of Multilayer Vessel>

The multilayer vessel according to the basic mode of this invention preferably has the individual physical properties including haze, total light transmittance, YI, oxygen transmission rate (OTR), and water vapor transmission rate (WVTR) controlled within the ranges described below, and in particular, has all of these physical properties controlled within these ranges.

<<Haze>>

The multilayer vessel of this invention preferably has a haze (%) after heat treatment at 121° C. for 30 minutes of 6% or smaller, more preferably 5% or smaller, and even more preferably 4% or smaller. The lower limit value of haze is preferably 0%, but may be practical enough even if it is 2% or above, and even 3% or above. Method for measuring the haze (%) after heat treatment at 121° C. for 30 minutes will follow a method described later in EXAMPLES.

<<Total Light Transmittance>>

The multilayer vessel of this invention preferably has a total light transmittance (%) after heat treatment at 121° C. for 30 minutes of 71% or larger, which is more preferably 73% or larger, even more preferably 75% or larger, yet more preferably 80% or larger, and further more preferably 85% or larger. The upper limit value of total light transmittance is preferably 100%, but may be practical enough even if it is 95% or below, even 93% or below, and in particular 90% or below. Method for measuring the total light transmittance (%) after heat treatment at 121° C. for 30 minutes will follow a method described later in EXAMPLES.

<<YI>>

The multilayer vessel of this invention preferably has a YI value after heat treatment at 121° C. for 30 minutes of 8 or smaller, more preferably 6 or smaller, and even more preferably 5 or smaller. The lower limit value of YI value is preferably 0, but may be practical enough even if it is 2 or above, even 3 or above, and in particular 4 or above. Method for measuring the YI value after heat treatment at 121° C. for 30 minutes will follow a method described later in EXAMPLES.

<<Oxygen Transmission Rate (OTR)>>

The multilayer vessel of this invention preferably shows an oxygen transmission rate (OTR) of 0.00100 mL/(0.21 atm·day·package) or smaller, when measured at 23° C. with a relative humidity inside the multilayer vessel of 100%, and with a relative humidity outside the multilayer vessel of 50%, which is more preferably 0.00030 mL/(0.21 atm·day·package) or smaller. The lower limit value of oxygen transmission rate is preferably 0 mL/(0.21 atm·day·package), but may be practical enough even if it is 0.00025 mL/(0.21 atm·day·package) or above. Method for measuring the oxygen transmission rate will follow a method descried later in EXAMPLE The multilayer vessel of this invention preferably shows an oxygen transmission rate (mL/(0.21 atm·day·package)) after heat treatment at 121° C. for 30 minutes of 0.00100 mL/(0.21 atm·day·package) or smaller, more preferably 0.00090 mL/(0.21 atm·day·package) or smaller, even more preferably 0.00030 mL/(0.21 atm·day·package) or smaller, and yet more preferably 0.00028 mL/(0.21 atm·day·package) or smaller. The lower limit value of oxygen transmission rate is preferably 0 mL/(0.21 atm·day·package), but may be practical enough even if it is 0.00025 mL/(0.21 atm·day·package) or above. Method for measuring the oxygen transmission rate after heat treatment will follow a method described later in EXAMPLES.

Difference between the oxygen transmission rate of the multilayer vessel of this invention measured at 23° C. with a relative humidity inside the multilayer vessel of 100%, and with a relative humidity outside the multilayer vessel of 50%, and, the oxygen transmission rate of the multilayer vessel of this invention measured after heat treatment at 121° C. for 30 minutes, is preferably 0.00005 mL/(0.21 atm·day·package) or smaller, more preferably 0.00003 mL/(0.21 atm·day·package) or smaller, and even more preferably 0.00002 mL/(0.21 atm·day·package) or smaller.

<<Water Vapor Transmission Rate (WVTR)>>

The multilayer vessel of this invention preferably has a water vapor transmission rate (WVTR) of 0.0009 g/(day·package) or smaller, and more preferably 0.0008 g/(day·package) or smaller. The lower limit value of water vapor transmission rate is preferably 0 g/(day·package), but may be practical enough even if it is 0.0005 g/(day·package) or above. Method for measuring the water vapor transmission rate will follow a method described later in EXAMPLES.

Embodiments of the multilayer vessel of this invention will be described below. This invention is, of course, not limited to these embodiments. The individual constituents are same as those of the multilayer vessel of the basic mode. The same will apply to preferable ranges. Again the same will apply to a method for manufacturing a multilayer vessel and a multilayer article described later.

The first embodiment of the multilayer vessel of this invention includes the layer (X) that contains a cycloolefin-based polymer (B) as the major ingredient, and the layer (Y) that contains the polyamide resin (A) as the major ingredient; the polyamide resin (A) is composed of a structural unit derived from diamine, and a structural unit derived from dicarboxylic acid; 70 mol % or more of the structural unit derived from diamine is derived from metaxylylenediamine; meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid; the cycloolefin-based polymer (B) has a glass transition temperature of 50 to 170° C.; the polyamide resin (A) has a glass transition temperature of 100 to 160° C.; the cycloolefin-based polymer (B) shows a melt viscosity of 100 to 250 Pa·sec at one or more temperatures between 260 and 300° C., under a shear rate of 1216 sec$^{-1}$; and the polyamide resin (A) shows a melt viscosity of 200 to 400 Pa·sec at 270° C., under a shear rate 1216 sec$^{-1}$.

With such design, the multilayer vessel will have excellent appearance and moldability, while keeping the barrier performance. More specifically, with the glass transition temperatures controlled within the above described ranges, the polyamide resin (A) that composes the layer (Y) will be less likely to adhere to mold, thereby the product with a good appearance will be obtained in high yield, and the moldability will improve. Meanwhile, with the melt viscosity controlled within the above described ranges, the layer (Y) and its adjoining layer (for example, layer (X)) will have small difference of viscosity at the interface, and thereby the molded article will have improved appearance.

By using the polyamide resin (A), which is usually an amorphous polyamide resin, the obtainable multilayer vessel will have good barrier performance. The multilayer vessel may also have a good transparency. The multilayer vessel may also have a good barrier performance and transparency even after heat treatment.

<Layer Structure>

In the first embodiment of this invention, the layer structure of the multilayer vessel is same as the above-described multilayer vessel of the basic mode. In particular in the first embodiment, the layer (X) and the layer (Y) are preferably brought into contact.

The total thickness of the multilayer vessel in the first embodiment of this invention is preferably least 0.5 mm or larger at the lowest, more preferably 0.8 mm or larger, and even more preferably 1.0 mm or larger. Meanwhile, the total thickness is preferably 2.5 mm or smaller, and more preferably 2.0 mm or smaller.

<Layer (X)>

The layer (X) that composes the multilayer vessel in the first embodiment of this invention is a layer that contains the cycloolefin-based polymer (B) as the major ingredient, and commonly serves as the water vapor barrier layer. Now, "contains . . . as the major ingredient" means that the content of the cycloolefin-based polymer (water vapor barrier polymer) in the layer (X) is 70% by mass or above, more preferably 80% by mass or above, and even more preferably 90 to 100% by mass. The layer (X) may contain only one type, or two or more types of cycloolefin-based polymers. When two or more types are contained, the total content of the cycloolefin-based polymers falls within the above described ranges.

Besides the cycloolefin-based polymer, the layer (X) may contain an additive such as antioxidant, matting agent, weathering stabilizer, UV absorber, crystal nucleating agent, plasticizer, flame retarder, and antistatic agent, depending on desired needs, without adversely affecting the effects of the invention.

The multilayer vessel according to the first embodiment of this invention may have a plurality of layers (X), and such plurality of layers (X) may have the same structure or different structures. The thickness of the layer (X) is preferably, but not restrictively, 20 to 2000 μm from the viewpoint of strength and cost, which is more preferably 50 to 1500 μm.

<<Cycloolefin-Based Polymer>>

The cycloolefin-based polymer (B) used in the first embodiment is not specifically limited, and may be selectable from known cycloolefin-based polymers. Specifically exemplified are the cycloolefin-based polymers described in paragraphs [0101] to [0103] of JP-A-2014-068767, the contents of which are incorporated by reference into this specification.

The cycloolefin-based polymer may be a cycloolefin polymer (COP), or may be a cycloolefin copolymer (COC). COP and COC advantageously exhibit good chemical properties such as heat resistance, light resistance or chemical resistance, which are typical features of cycloolefin-based polymer; and good physical properties such as mechanical characteristics, melting characteristics, fluid characteristics and dimensional accuracy, which are typical features of amorphous resin.

COP is typically a polymerized product obtained by ring-opening polymerization of norbornene, followed by hydrogenation. COP is described, for example, in JP-A-5-317411, and is commercially available from ZEON Corporation under the names ZEONEX (registered trademark) (ZEONEX 5000 (glass transition temperature=69° C.), ZEONEX 690R (glass transition temperature=136° C.), ZEONEX 790R (glass transition temperature=163° C.) etc.) and ZEONOR (registered trademark) (ZEONOR 1020R (glass transition temperature=102° C.)); and from Daikyo Seiko, Ltd. under the name Daikyo Resin CZ (registered trademark).

COC is typically a copolymer started from norbornene and olefin such as ethylene; and a copolymer started from tetracyclododecene and olefin such as ethylene. COC is commercially available, for example, from Mitsui Chemicals, Inc. under the name APEL (registered trademark).

The cycloolefin-based polymer (B) used in this invention preferably has a glass transition temperature of 50° C. or above at the lowest, preferably 60° C. or above, more preferably 65° C. or above, may be 100° C. or above, still may be 120° C. or above, and even may be 130° C. or above. Meanwhile, the cycloolefin-based polymer (B) preferably has a glass transition temperature of 170° C. or below at the highest, more preferably 150° C. or below, even more preferably 145° C. or below, and yet more preferably 140° C. or below.

The cycloolefin-based polymer (B) used in this invention shows a melt viscosity of 100 to 250 Pa·sec at one or more temperatures between 260 and 300° C., under a shear rate of 1216 sec$^{-1}$. More preferably, the melt viscosity is 100 to 250 Pa·sec, when measured at 300° C., under a shear rate of 1216 sec$^{-1}$. The melt viscosity is preferably 100 Pa·sec or above at the lowest, more preferably 110 Pa·sec or above, and even more preferably 120 Pa·sec or above. The melt viscosity is preferably 250 Pa·sec or below at the highest, more preferably 240 Pa·sec or below, and even more preferably 230 Pa·sec or below.

<Layer (Y)>

The layer (Y) in the first embodiment of this invention is synonymous to the layer (Y) in the multilayer vessel of the basic mode. The same will apply to preferable ranges.

<<Polyamide Resin (A)>>

The polyamide resin (A) used in the first embodiment of this invention is synonymous to the polyamide resin (A) in the multilayer vessel of the basic mode. In particular, the polyamide resin (A) used in the first embodiment has a glass transition temperature of 100° C. or above at the lowest, preferably 110° C. or above, and more preferably 115° C. or above. Meanwhile, the polyamide resin (A) has a glass transition temperature of 160° C. or below at the highest, preferably 150° C. or below, and more preferably 145° C. or below.

The Polyamide resin (A) used in the first embodiment of this invention has a melt viscosity of 200 Pa·sec or above at the lowest, when measured at 270° C., under a shear rate of 1216 sec$^{-1}$, preferably 230 Pa·sec or above, and more preferably 250 Pa·sec or above. Meanwhile, the polyamide resin (A) has a melt viscosity of 400 Pa·sec or below at the highest, when measured at 270° C., under a shear rate of 1216 sec$^{-1}$, more preferably 350 Pa·sec or below, and even more preferably 330 Pa·sec or below.

When the layer (Y) contains two or more types of polyamide resins (A), at least one type of polyamide resin (A) preferably satisfies the above described ranges, and 90% by mass or more of the polyamide resin (A) contained in the layer (Y) preferably satisfies the above described ranges.

The polyamide resin (A) used in the first embodiment of this invention preferably has a moisture content, when measured in a nitrogen atmosphere at 235° C. for 30 minutes, of 1000 ppm by mass or less, more preferably 800 ppm by mass or less, which may be 500 ppm by mass or less, even may be 400 ppm by mass or less, yet may be 350 ppm by mass or less, and again may be 300 ppm by mass or less. The lower limit value of moisture content may be 0 ppm by mass, but may be practical enough even if it is 100 ppm by mass or above. Method for measuring the moisture content will follow a method described later in EXAMPLES.

<Relation Between Layer (X) and Layer (Y)>

In the multilayer vessel according to the first embodiment of this invention, difference between the glass transition temperatures of the cycloolefin-based polymer (B) contained in the layer (X) and the polyamide resin (A) contained in the layer (Y) is 110° C. or smaller, and preferably 70° C. or smaller. The lower limit value may, for example, be 1° C. or larger. With the difference of the glass transition temperatures controlled within the above described ranges, the moldability may be improved.

In this invention, although it suffices that at least one layer in the layer (X) and at least one layer in the layer (Y) satisfy the above-described relations, it is preferable that all layers in the layer (X) and all layers in the layer (Y), which compose the multilayer vessel, satisfy the above-described relations.

When two or more types of cycloolefin-based polymers are contained in the layer (X), and/or, two or more types of polyamide resins (A) are contained in the layer (Y), it is preferable that 70% by mass or more, preferably 80% by mass or more, and even more preferably 90 to 100% by mass of the resins in the individual layers satisfy the above-described relation.

<Optional Layer>

Besides the layer (X) and the layer (Y), the multilayer vessel according to the first embodiment of this invention may contain an optional layer depending on desired performances. Details of such optional layer is synonymous to those of the multilayer vessel of the basic mode, and the same will apply to the preferable ranges.

<Oxygen Transmission Rate of Multilayer Vessel>

The multilayer vessel according to the first embodiment of this invention preferably shows an oxygen transmission rate (OTR) of 0.00100 mL/(0.21 atm·day·package) or smaller, when measured at 23° C. with a relative humidity inside the multilayer vessel of 100%, and with a relative humidity outside the multilayer vessel of 50%, which is more preferably 0.00030 mL/(0.21 atm·day·package) or smaller. The lower limit value of oxygen transmission rate is preferably 0 mL/(0.21 atm·day·package), but may be practical enough even if it is 0.00025 mL/(0.21 atm·day·package) or above. Method for measuring the oxygen transmission rate will follow a method described later in EXAMPLES.

The second embodiment of the multilayer vessel of this invention is a multilayer syringe barrel for prefilled syringe (may simply be referred to as "multilayer syringe barrel", hereinafter). More specifically, the multilayer syringe barrel disclosed in the second embodiment includes the layer (X) that contains, as the major ingredient, the cycloolefin-based polymer whose glass transition temperature is lower than 100° C., and the layer (Y) that contains the polyamide resin (A) as the major ingredient; the polyamide resin (A) is composed of a structural unit derived from diamine, and a structural unit derived from dicarboxylic acid; 70 mol % or more of the structural unit derived from diamine is derived from metaxylylenediamine; meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid. By using such amorphous polyamide resin with a specific composition, obtainable is the multilayer syringe barrel for prefilled syringe which excels in oxygen barrier performance even after being filled with a chemical liquid and kept for a predetermined period, and is suppressed from whitening (kept highly translucent).

By using such polyamide resin (A) which is commonly an amorphous polyamide resin, the obtainable multilayer syringe barrel will have excellent gas barrier performance and transparency, even after heat disinfection (sterilization).

<Layer Structure>

The layer structure in the second embodiment of this invention is same as that in the above-described multilayer vessel of the basic mode.

In particular, in the multilayer syringe barrel for prefilled syringe of the second embodiment, at least one layer in the outer layer is preferably thicker than at least one layer in the inner layer. Difference in the thickness between the outer layer and the inner layer is preferably 200 μm or larger, more preferably 300 μm or larger, and even more preferably 300 to 900 μm.

The total thickness of the multilayer syringe barrel for prefilled syringe of the second embodiment is preferably 0.5 mm or above at the lowest, more preferably 0.8 mm or above, and even more preferably 1.0 mm or above. The total thickness is preferably 2.5 mm or smaller, and more preferably 2.0 mm or smaller.

<Layer (X)>

In the second embodiment of this invention, the layer (X) that composes the multilayer syringe barrel for prefilled syringe contains, as the major ingredient, at least one type of cycloolefin-based polymer (may be referred to as "low Tg cycloolefin-based polymer", hereinafter) whose glass transition temperature is lower than 100° C., and usually acts as a water vapor barrier layer. Now, "contains, as the major ingredient," means that the content of the low Tg cycloolefin-based polymer (water vapor barrier polymer) in the layer (X) is 70% by mass or more, more preferably 80% by mass or more, and even more preferably 90 to 100% by mass. The layer (X) may contain only one type of, or two or more types of, the low Tg cycloolefin-based polymers. When two or more types are contained, the total content of the low Tg cycloolefin-based polymers falls within the above-described ranges.

Besides the low Tg cycloolefin-based polymer, the layer (X) may contain a polyolefin resin other than the low Tg cycloolefin-based polymer, or any other additive such as antioxidant, matting agent, weathering stabilizer, UV absorber, crystal nucleating agent, plasticizer, flame retarder, antistatic agent or the like, depending on desired performances, without adversely affecting the effects of this invention.

The multilayer syringe barrel for prefilled syringe of the second embodiment of this invention may have a plurality of layers (X), whose structures may be same with, or different from each other. The thickness of the layer (X) is preferably, but not restrictively in particular, 20 to 2000 μm from the viewpoint of strength and cost, which is more preferably 50 to 1500 μm.

<<Low Tg Cycloolefin-Based Polymer>>

In the second embodiment of this invention, the cycloolefin-based polymer whose glass transition temperature is lower than 100° C. is used. Usage of such cycloolefin-based polymer, whose glass transition temperature is lower than 100° C., allows injection molding under relatively mild temperature conditions. The low Tg cycloolefin-based polymer preferably has a glass transition temperature of 90° C. or below at the highest. The lower limit value of glass transition temperature is preferably 50° C. or above, and more preferably 60° C. or above. The glass transition temperature may be measured as described later in EXAMPLES. Note that instruments, etc. used in EXAMPLES are no more available due to discontinuation or other reasons, other equivalent instruments will suffice. The same will apply to other methods for measurement.

The low Tg cycloolefin-based polymer, which is used in the second embodiment of this invention as the major ingredient of the layer (X), may be any of known cycloolefin-based polymers, and any of those having a glass transition temperature of lower than 100° C.

The cycloolefin-based polymer may be a cycloolefin polymer (COP), or may be a cycloolefin copolymer (COC). COP and COC advantageously exhibit good chemical properties such as heat resistance, light resistance or chemical resistance, which are typical features of cycloolefin-based polymer; and good physical properties such as mechanical characteristics, melting characteristics, fluid characteristics and dimensional accuracy, which are typical features of amorphous resin.

COP is typically a polymerized product obtained by ring-opening polymerization of norbornene, followed by hydrogenation. COP is described, for example, in JP-A-5-317411, and is commercially available from ZEON Corporation under the name ZEONEX (registered trademark).

COC is typically a copolymer started from norbornene and olefin such as ethylene; and a copolymer started from tetracyclododecene and olefin such as ethylene. COC is commercially available, for example, from Mitsui Chemicals, Inc. under the name APEL (registered trademark).

<Layer (Y)>

In the second embodiment of this invention, the layer (Y) that composes the multilayer syringe barrel for prefilled syringe contains at least one type of predetermined polyamide resin (A) as the major ingredient, and typically serves as a gas barrier layer. The layer (Y) in the second embodiment is synonymous to that in the multilayer vessel according to the basic mode of this invention, and the same will apply to preferable ranges.

<Physical Properties of Multilayer Syringe Barrel for Prefilled Syringe>

The multilayer syringe barrel, which is the second embodiment of the multilayer vessel of this invention, preferably has the individual physical properties including haze, total light transmittance, YI and oxygen transmission rate (OTR), controlled within the ranges described below, and in particular, has all of these physical properties controlled within these ranges.

<<Haze>>

The multilayer syringe barrel for prefilled syringe, which is the second embodiment of the multilayer vessel of this invention, preferably has a haze (%) of 4.0% or smaller, which is more preferably 3.0% or smaller, and even more preferably 2.8% or smaller. The lower limit value of haze is preferably 0.0%, but may be practical enough even if it is 2.0% or above. Difference in the haze of the multilayer syringe barrel for prefilled syringe, which is the second embodiment of the multilayer vessel of this invention, between before and after storage with filled water (haze after storage–initial haze) is preferably 3.0% or smaller, more preferably 1.0% or smaller, and even more preferably 0.5% or smaller. The lower limit value may be −0.2% or above for example, allowing that the haze can even be reduced than before, as a result of storage with filled water.

Method for measuring the haze, and details of the storage with filled water will follow the description later in EXAMPLES.

<<Oxygen Transmission Rate>>

The multilayer syringe barrel for prefilled syringe, which is the second embodiment of the multilayer vessel of this invention, preferably shows an oxygen transmission rate (mL/(0.21 atm·day·package)) of 0.00100 mL/(0.21 atm·day·package) or below, which is more preferably 0.00090 mL/(0.21 atm·day·package) or below, even more preferably 0.00030 mL/(0.21 atm·day·package) or below, and yet more preferably 0.00028 mL/(0.21 atm·day·package) or below. The lower limit value of oxygen transmission rate is preferably 0 mL/(0.21 atm·day·package), but may be practical enough even if it is 0.00025 mL/(0.21 atm·day·package) or above.

The multilayer syringe barrel for prefilled syringe, which is the second embodiment of the multilayer vessel of this invention, preferably show a difference in the oxygen transmission rate between before and after storage with filled water (oxygen transmission rate after storage–initial oxygen transmission rate) of 0.00002 mL/(0.21 atm·day·package) or below, which is more preferably 0.00001 mL/(0.21 atm·day·package) or below. The lower limit value may, for example, be 0.00000 mL/(0.21 atm·day·package) or above.

The oxygen transmission rate may be measured according to the method described later in EXAMPLES.

<<YI Value>>

The multilayer syringe barrel for prefilled syringe, which is the second embodiment of the multilayer vessel of this invention, preferably show a YI value of 4.0 or smaller, which is more preferably 3.0 or smaller, and even more preferably 2.5 or smaller. The lower limit value of YI value is preferably 0.0, but may be practical enough even if it is 2.0 or above.

The multilayer syringe barrel for prefilled syringe, which is the second embodiment of this invention, preferably show a difference in the YI value between before and after storage with filled water (YI value after storage–initial YI value) of 3.0 or smaller, which is more preferably 2.0 or smaller. The difference is preferably 0.0, but may be practically applicable if it is 1.0 or above.

The YI value may be measured according to the method described later in EXAMPLE.

<Structure of Multilayer Syringe Barrel for Prefilled Syringe>

Next, a structure of the multilayer syringe barrel for prefilled syringe, which is the second embodiment of the multilayer vessel of this invention, will be explained referring to FIG. 1. Note that the multilayer syringe barrel for prefilled syringe, which is the second embodiment of the multilayer vessel of this invention, is of course not limited to that illustrated in FIG. 1.

FIG. 1 is a schematic drawing illustrating the prefilled syringe of the second embodiment, wherein reference numeral 1 stands for a multilayer syringe barrel of a prefilled syringe, 2 for a hub of the multilayer syringe barrel, 3 for a flange of the multilayer syringe barrel, 4 for a cap for the hub, 5 for a gasket, 6 for a rod of a plunger, and 7 for a chemical liquid.

According to the second embodiment, by employing the above-described multilayer structure, the multilayer syringe barrel 1 will excel in the oxygen barrier performance, and will be less likely to be whitened even after filled with a chemical liquid and stored for a certain period of time.

The multilayer syringe barrel 1 of the second embodiment preferably has a length (L) of 50 to 200 mm, which is more preferably 55 to 175 mm. The length (L) of the multilayer syringe barrel of the second embodiment is measured, typically as illustrated in FIG. 1, from the end of the hub to the opposite end (flange in FIG. 1).

The body (a part to be filled with chemical liquid) of the multilayer syringe barrel 1 of the second embodiment is preferably cylindrical. The body of the multilayer syringe barrel 1 of the second embodiment, when given in the form of cylinder, preferably has an outer diameter (D) of 2 to 40 mm, which is more preferably 5 to 36 mm. The outer diameter (D) of the multilayer syringe barrel of the second embodiment is defined by, typically as illustrated in FIG. 1, the outer diameter of a part of the multilayer syringe barrel in which a chemical liquid will be filled.

The chemical liquid 7 to be filled in the multilayer syringe barrel 1 of the second embodiment preferably amounts, for example, 0.1 to 150 mL, which is more preferably 0.4 to 120 mL.

The hub 2 of the multilayer syringe barrel 1 may have an optional form such as tapered form or cylindrical form.

Also the geometry of the flange 3 of the multilayer syringe barrel is not specifically limited. Even an embodiment without providing the flange will be acceptable.

The cap 4 is not specifically limited so long as it can seal the multilayer syringe barrel. The material is typically a rubber. Also employable is a cap having a preset needle.

In addition, the syringe in this invention typically has the cap 4 that seals the hub 2 of the multilayer syringe barrel 1, and, a plunger that has the rod 6 with the gasket 5 attached to the end thereof.

The syringe of this invention is used as a prefilled syringe, with the multilayer syringe barrel 1 of the syringe filled with the chemical liquid 7, and sealed with the cap 4 and the gasket 5.

The chemical liquid is exemplified by aqueous solution containing a chemical dissolved in water; high-concentration sodium chloride injection; glucose injection; aqueous heparin sodium solution; nitroglycerin, isosorbide dinitrate; cyclosporin; benzodiazepines; antibiotic; antithrombotic agent such as heparin; insulin; antiulcer agent; analgesic; cardiotonic; intravenous anesthetic; antiparkinsonian; ulcer treatment agent; adrenocortical hormone preparation; anti-arrhythmic agent; corrective electrolyte solution; antiviral agent; immunostimulant; and adrenaline preparation. The aqueous solution containing a chemical dissolved in water is preferable. When the aqueous solution containing a chemical dissolved in water is used, the concentration thereof is preferably 0.0001 to 30% by mass.

The adrenaline preparation is used as an adjuvant remedy for anaphylaxis, when occurs, by temporarily moderating progress of the symptom to prevent shock, and is also marketed as a self-injection medicine. The preparation needs be injected promptly upon onset of the symptom, and a less fragile, small-sized resin vessel is preferably used. By using the multilayer syringe barrel of the second embodiment of this invention as a vessel for the adrenaline preparation, there will be a reduced risk of fracture, and adrenalin will be suppressed from being oxidized.

The chemical to be stored in the syringe of this invention conceptually include, besides medicine, ingredients to be administered for nutrition support. The chemical used in this invention is exemplified by minerals, vitamins, and various amino acids.

The third embodiment of the multilayer vessel of this invention is the multilayer syringe barrel for prefilled syringe. More specifically, the multilayer syringe barrel disclosed in the third embodiment has the layer (X) that contains, as the major ingredient, at least one polymer selected from polypropylene-based polymer and cycloolefin-based polymer having a glass transition temperature of 100° C. or higher, and the layer (Y) that contains the polyamide resin (A) as the major ingredient, wherein the polyamide resin (A) is composed of a structural unit derived from diamine and a structural unit derived from dicarboxylic acid, 70 mol % or more of the structural unit derived from diamine is derived from metaxylylenediamine, meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid.

By using such amorphous polyamide resin having the specific composition, it now becomes possible to provide the multilayer syringe barrel for prefilled syringe, the syringe, and the prefilled syringe, which will excel in the oxygen barrier performance even after filled with a chemical liquid and stored for a certain period of time, and will be less likely to be whitened even after heat sterilization. The multilayer syringe will also be well suppressed in whitening even after stored for a certain period of time with a chemical liquid filled therein, and will excel in the oxygen barrier performance even after heat sterilization.

These effects may be achieved by using the polyamide resin (A) with a specific composition as the polyamide resin (A), and by using the polypropylene-based polymer or the cycloolefin-based polymer with a glass transition temperature of 100° C. or above as the polyolefin resin.

By using such polyamide resin (A), which is typically an amorphous polyamide resin, the multilayer syringe barrel will have further improved barrier performance and translucency even after heat sterilization.

<Layer Structure>

The layer structure in the third embodiment of this invention is same as that in the above-described multilayer vessel of the basic mode.

In particular, the total thickness of the multilayer vessel in the third embodiment is preferably 0.5 mm or above at the lowest, more preferably 0.8 mm or above, and even more preferably 1.0 mm or above. The total thickness is preferably 2.5 mm or below at the highest, and more preferably 2.0 mm or below.

<Layer (X)>

The layer (X), which composes the multilayer syringe barrel for prefilled syringe of the third embodiment of this invention, contains as the major ingredient at least one polymer selected from polypropylene-based polymer and cycloolefin-based polymer having a glass transition temperature of 100° C. or higher (may occasionally be referred to as "specific polyolefin resin", hereinafter), and usually acts as a water vapor barrier layer. Now, "contains as the major ingredient" means that the content of the specific polyolefin resin (water vapor barrier polymer) in the layer (X) is 70% by mass or more, preferably 80% by mass or more, and even more preferably 90 to 100% by mass or more. The layer (X) may contain only one type of, or two or more types of, the specific polyolefin resins. When two or more types are contained, the total content of the specific polyolefin resins falls within the above-described ranges.

Besides the specific polyolefin resin, the layer (X) may contain a polyolefin resin other than the specific polyolefin resin, or any other additive such as antioxidant, matting agent, weathering stabilizer, UV absorber, crystal nucleating agent, plasticizer, flame retarder, antistatic agent or the like, depending on desired performances, without adversely affecting the effects of this invention.

The multilayer syringe barrel for prefilled syringe according to the third embodiment may have a plurality of layers (X), whose structures may be same with, or different from each other. The thickness of the layer (X) is preferably, but not restrictively in particular, 20 to 2000 μm from the viewpoint of strength and cost, which is more preferably 50 to 1500 μm.

<<Specific Polyolefin Resin>>

In the third embodiment of this invention, as has been described above, at least one type of polymer selected from polypropylene-based polymer and cycloolefin-based polymer having a glass transition temperature of 100° C. or above is used. By using such specific polyolefin resin, the multilayer syringe barrel will effectively be prevented from whitening after heat sterilization.

The specific polyolefin resin preferably contains at least one type selected from the cycloolefin-based polymers.

The lower limit value of glass transition temperature of the cycloolefin-based polymer, having a glass transition temperature of 100° C. or above, is more preferably 110° C. or above, and even more preferably 120° C. or above. The upper limit value of glass transition temperature is preferably 200° C. or below, more preferably 190° C. or below, and may also be 150° C. or below. The glass transition temperature may be measured according to the method described later in EXAMPLES. Note however that instruments, etc. used in EXAMPLES are no more available due to discontinuation or other reasons, other equivalent instruments will suffice. The same will apply to other methods for measurement.

The specific polyolefin resin is selectable from known polyolefins.

More specifically, exemplified are those come under the specific polyolefin resin, among the polyolefin resins described in paragraphs [0101] to [0103] of JP-A-2014-068767, the contents of which are incorporated by reference into this specification.

The cycloolefin-based polymer may be a cycloolefin polymer (COP), or may be a cycloolefin copolymer (COC). COP and COC advantageously exhibit good chemical properties such as heat resistance, light resistance or chemical resistance, which are typical features of cycloolefin-based polymer; and good physical properties such as mechanical characteristics, melting characteristics, fluid characteristics and dimensional accuracy, which are typical features of amorphous resin. Meanwhile, the polypropylene-based polymer (PP) is preferable from the viewpoint of oil resistance.

COP is typically a polymerized product obtained by ring-opening polymerization of norbornene, followed by hydrogenation. COP is described, for example, in JP-A-5-317411, and is commercially available from ZEON Corporation under the name ZEONEX (registered trademark) or ZEONOR (registered trademark); and from Daikyo Seiko, Ltd. under the name Daikyo Resin CZ (registered trademark). More specifically, ZEONEX 690R is exemplified.

COC is typically a copolymer started from norbornene and olefin such as ethylene; and a copolymer started from tetracyclododecene and olefin such as ethylene. COC is commercially available, for example, from Mitsui Chemicals, Inc. under the name APEL (registered trademark).

As PP, usable are known polymers such as propylene homopolymer, propylene-ethylene block copolymer, and propylene-ethylene random copolymer. The commercially available product is exemplified by Bormed RB845MO from BOREALIS AG.

<Layer (Y)>

In the third embodiment of this invention, the layer (Y) that composes the multilayer syringe barrel for prefilled syringe is a layer having at least one type of predetermined polyamide resin (A) as the major ingredient, and usually acts as a gas barrier layer. The layer (Y) in the third embodiment is synonymous to that in the multilayer vessel according to the basic mode of this invention, and the same will apply to preferable ranges.

<Physical Properties of Multilayer Syringe Barrel for Prefilled Syringe>

The multilayer syringe barrel for prefilled syringe according to the third embodiment of this invention preferably has the haze, total light transmittance, YI value and oxygen transmission rate controlled within the ranges described below, and in particular, has all of these physical properties controlled within these ranges.

<<Haze>>

The multilayer syringe barrel for prefilled syringe according to the third embodiment preferably has a haze (%) of 4.0% or smaller, which is more preferably 3.0% or smaller. The lower limit value of haze is preferably 0.0%, but may be practical enough even if it is 2.0% or above.

The multilayer syringe barrel for prefilled syringe according to the third embodiment preferably shows a decrease of haze after heat sterilization (haze after heat sterilization−initial haze) of 2.0% or smaller, more preferably 1.5% or smaller, and even more preferably 0.8% or smaller. The lower limit value may be 0% or above for example, but may be practical enough even if it is 0.1% or above.

Moreover, the multilayer syringe barrel for prefilled syringe according to the third embodiment preferably shows a decrease of haze after storage with filled water (haze after storage−initial haze) of 2.0% or smaller, more preferably 1.5% or smaller, even more preferably 1.0% or smaller, and yet more preferably 0.8% or smaller. The lower limit value is ideally 0% or above, but may be practical enough even if it is 0.1% or above.

Method for measuring the haze, and details of heat sterilization and storage with filled water will follow the descriptions later in EXAMPLES.

<<Total Light Transmittance>>

The multilayer syringe barrel for prefilled syringe according to the third embodiment preferably shows a total light transmittance (%) of 85.0% or larger, which is more preferably 86.0% or larger, and even more preferably 88.0% or larger. The upper limit value of total light transmittance is preferably 100.0%, but may be practical enough even if it is 90.0% or above.

The multilayer syringe barrel for prefilled syringe according to the third embodiment preferably shows a decrease of total light transmittance after heat sterilization (total light transmittance after heat sterilization−initial total light transmittance) of 2.0% or smaller, more preferably 1.5% or smaller, even more preferably 1.0% or smaller, and yet more preferably 0.8% or smaller. The lower limit value is ideally 0% or above, but may be practical enough even if it is 0.1% or above.

Moreover, the multilayer syringe barrel for prefilled syringe according to the third embodiment preferably shows a decrease of total light transmittance after storage with filled water (total light transmittance after storage–initial total light transmittance) of 2.0% or smaller, more preferably 1.5% or smaller, and even more preferably 1.2% or smaller. The lower limit value is ideally 0% or above, but practically acceptable if it is 0.1% or above.

Method for measuring the total light transmittance will follow the description later in EXAMPLES.

<<YI Value>>

The multilayer syringe barrel for prefilled syringe according to the third embodiment preferably has a YI value of 4.0 or smaller, which is more preferably 3.0 or smaller, and even more preferably 2.5 or smaller. The lower limit value of YI value is preferably 0, but may be practical enough even if it is 2.0 or above.

The multilayer syringe barrel for prefilled syringe according to the third embodiment preferably shows a decrease of YI value after heat treatment (YI value after heat treatment–initial YI value) of 2.5 or smaller, which is more preferably 2.2 or smaller. The lower limit value is preferably 0, but may be practical enough even if it is 0.1 or above.

Moreover, the multilayer syringe barrel for prefilled syringe according to the third embodiment preferably shows a decrease of YI value after storage with filled water (YI value after storage–initial YI value) of 2.5 or smaller, which is more preferably 2.0 or smaller. The lower limit value is preferably 0, but may be practical enough even if it is 0.1 or above.

The YI value may be measured according to the method described later in EXAMPLES.

<<Oxygen Transmission Rate>>

The multilayer syringe barrel for prefilled syringe according to the third embodiment preferably shows an oxygen transmission rate (mL/(0.21 atm·day·package)) of 0.00100 mL/(0.21 atm·day·package) or below, more preferably 0.00090 mL/(0.21 atm·day·package) or below, even more preferably 0.00030 mL/(0.21 atm·day·package) or below, and yet more preferably 0.00028 mL/(0.21 atm·day·package) or below. The lower limit value of oxygen transmission rate is preferably 0 mL/(0.21 atm·day·package), but may be practical enough even if it is 0.00025 mL/(0.21 atm·day·package) or above.

The multilayer syringe barrel for prefilled syringe according to the third embodiment preferably shows a decrease of oxygen transmission rate after heat sterilization (oxygen transmission rate after heat sterilization–initial oxygen transmission rate) of 0.00002 mL/(0.21 atm·day·package) or below, which is more preferably 0.00001 mL/(0.21 atm·day·package) or below. The lower limit value may, for example, be 0.00000 mL/(0.21 atm·day·package) or above.

Moreover, the multilayer syringe barrel for prefilled syringe according to the third embodiment preferably shows a decrease of oxygen transmission rate after storage with filled water (oxygen transmission rate after storage–initial oxygen transmission rate) of 0.00002 mL/(0.21 atm·day·package) or smaller, which is more preferably 0.00001 mL/(0.21 atm·day·package) or smaller. The lower limit value may, for example, be 0.00000 mL/(0.21 atm·day·package) or above.

The oxygen transmission rate may be measured according to the method described later in EXAMPLES.

<Structure of Multilayer Syringe Barrel for Prefilled Syringe>

The structure of the multilayer syringe barrel for prefilled syringe according to the third embodiment is synonymous to that of the multilayer syringe barrel for prefilled syringe according to the second embodiment, and the same will apply to preferable ranges. Also the chemical liquid is synonymous to that described regarding the multilayer syringe barrel for prefilled syringe according to the second embodiment, and the same will apply to preferable ranges.

The multilayer vessel according to the fourth embodiment of this invention includes the layer (X) that contains at least one type of the polyolefin resin as the major ingredient, an adhesive layer, and the layer (Y) that contains the polyamide resin (A) as the major ingredient, arranged in this order; the polyamide resin (A) is composed of a structural unit derived from diamine and a structural unit derived from dicarboxylic acid; 70 mol % or more of the structural unit derived from diamine is derived from metaxylylenediamine; meanwhile 30 to 60 mol % of the structural unit derived from dicarboxylic acid is derived from straight chain aliphatic $\alpha,\omega$-dicarboxylic acid having 4 to 20 carbon atoms, and 70 to 40 mol % is derived from isophthalic acid.

The polyamide resin (A) is usually an amorphous polyamide resin. By using such polyamide resin, the multilayer vessel will have excellent gas barrier performance and transparency even after heat sterilization.

<Layer Structure>

The layer structure of the multilayer vessel according to the fourth embodiment of this invention is not specifically limited so long as the layer (X), the adhesive layer, and the layer (Y) are arranged in this order, without special limitations on the number and types of layer (X) and layer (Y). In the fourth embodiment, provided that the layer (X), the adhesive layer, and the layer (Y) are arranged in this order, an additional layer may be interposed between the layer (X) and the adhesive layer, and, between the adhesive layer and the layer (Y). It is however preferable in the fourth embodiment that the layer (X) and the adhesive layer are brought into contact, and also that the layer (Y) and the adhesive layer are brought into contact.

The multilayer vessel according to the fourth embodiment of this invention is preferably composed of at least three layers, which is more preferably 3 to 10 layers, and even more preferably 3 to 5 layers.

The number of layers (X) in the multilayer vessel according to the fourth embodiment is preferably 1 to 5, and more preferably 2 to 4. The number of layers (Y) in the multilayer vessel is preferably 1 to 3, and more preferably 1 or 2.

For example, the multilayer vessel according to the fourth embodiment may have one layer (X), one adhesive layer and one layer (Y) to form an X/adhesive layer/Y structure (layer (X) for the inner layer), or to form a Y/adhesive layer/X structure (layer (Y) for the inner layer), or alternatively may have two layers (X), two adhesive layers, and one layer (Y) to form a five-layered structure given by X/adhesive layer/Y/adhesive layer/X.

The multilayer vessel according to the fourth embodiment preferably has the layers (X) for the inner layer and the outer layer, and has the layer (Y) for at least one intermediate layer (X/adhesive layer/Y/adhesive layer/X structure). In the fourth embodiment, there may be both regions having therein the layer (X) and the adhesive layer and the layer (Y) arranged in this order, and having therein these layers not arranged in this order, such as given by (X/adhesive layer/Y/X/Y/X). In this invention, various thermoplastic resin layers may additionally be contained depending on purposes, without special limitation.

Now the "inner layer" means a layer that resides inside the layer (Y) which serves as one intermediate layer, among the layers composing the multilayer vessel, meanwhile the "outer layer" means a layer that resides outside the layer (Y) which serves as one intermediate layer, among the layers composing the multilayer vessel. The inner layer and the outer layer may be the innermost layer and the outermost layer, respectively, or may have additional innermost layer and outermost layer.

The total thickness of the multilayer vessel according to the fourth embodiment of this invention may properly be determined depending on applications. In one embodiment, the lower limit value is preferably 0.3 mm or above, more preferably 0.5 mm or above, and even more preferably 0.7 mm or above. The upper limit value is preferably 2.0 mm or below, more preferably 1.5 mm or below, and even more preferably 1.2 mm or below.

<Layer (X)>

The layer (X) that composes the multilayer vessel according to the fourth embodiment of this invention is synonymous to that in the multilayer vessel according to the basic mode of this invention, and the same will apply to preferable ranges. In particular in the fourth embodiment, the layer (X) of the multilayer vessel, when manufactured by direct blow molding, is preferably 20 to 800 μm thick, and more preferably 50 to 700 μm thick. Since the adhesive layer is provided therein, this invention can effectively suppress separation of the layers, even if the individual layers are thinned and the multilayer vessel is designed to have a large capacity.

When the multilayer vessel according to the fourth embodiment of this invention is manufactured by direct blow molding, the layer (Y) is preferably 1 to 500 μm thick, more preferably 20 to 300 μm thick, and even more preferably 50 to 200 μm thick.

<Adhesive Layer>

In the multilayer vessel according to the fourth embodiment of this invention, the adhesive layer is provided. The adhesive layer preferably contains an adhesive thermoplastic resin. The adhesive thermoplastic resin is exemplified by acid-modified polyolefin resins obtained by modifying a polyolefin resin such as polyethylene or polypropylene, with an acid such as unsaturated carboxylic acid (acrylic acid, methacrylic acid, maleic acid, maleic anhydride, fumaric acid, itaconic acid, etc.); and polyester-based thermoplastic elastomers containing polyester-based block copolymers as the major ingredients. The acid-modified polyolefin resin is preferable. More specifically, when a polypropylene-based polymer is used as the polyolefin resin, a possible embodiment is such that the resin contained in the adhesive layer is the acid-modified polypropylene-based polymer.

The adhesive layer may contain one type of, or two or more types of, adhesive thermoplastic resins. In the adhesive layer, the total content of the adhesive thermoplastic resins preferably accounts for 80% by mass or more of the whole, which is more preferably 90% by mass or more. Possible ingredient of the adhesive layer, other than the adhesive thermoplastic resin, is exemplified by additives such as antioxidant, matting agent, weathering stabilizer, UV absorber, crystal nucleating agent, plasticizer, flame retarder, and antistatic agent.

From the viewpoints of allowing the adhesive layer to exhibit a practical level of adhesion strength and to be sufficiently moldable, the thickness is preferably 2 μm or above at the lowest, more preferably 5 μm or above, and even more preferably 10 μm or above. Meanwhile, the thickness is preferably 100 μm or below at the largest, more preferably 90 μm or below, even more preferably 80 μm or below, yet more preferably 50 μm or below, furthermore preferably 30 μm or below, and again furthermore preferably 20 μm or below.

<Optional Layer>

Besides the layer (X), the adhesive layer and the layer (Y), the multilayer vessel according to the fourth embodiment of this invention may include an optional layer depending on desired performances.

<Physical Properties of Multilayer Vessel>

The multilayer vessel according to the fourth embodiment of this invention preferably has the individual physical properties including YI, oxygen transmission rate (OTR), and water vapor transmission rate (WVTR) controlled within the ranges described below, and in particular, has all of these properties well controlled within these ranges.

<<YI>>

The multilayer vessel according to the fourth embodiment of this invention preferably has a YI value after heat treatment at 121° C. for 30 minutes of 8 or smaller, more preferably 7 or smaller, and even more preferably 6 or smaller. The lower limit value of YI value is preferably 0, but may be practical enough even if it is 2 or above, preferably 3 or above, and particularly 4 or above. Method for measuring the YI value after heat treatment at 121° C. for 30 minutes will follow a method described later in EXAMPLES.

<<Oxygen Transmission Rate (OTR)>>

The multilayer vessel according to the fourth embodiment of this invention preferably shows an oxygen transmission rate (OTR), when measured at 23° C. with a relative humidity inside the multilayer vessel of 100%, and with a relative humidity outside the multilayer vessel of 50%, of 0.00100 mL/(0.21 atm·day·package) or smaller, which is more preferably 0.00031 mL/(0.21 atm·day·package) or smaller. The lower limit value of oxygen transmission rate is preferably 0 mL/(0.21 atm·day·package), but may be practical enough even if it is 0.00025 mL/(0.21 atm·day·package) or above. Method for measuring the oxygen transmission rate will follow a method described later in EXAMPLES.

The multilayer vessel according to the fourth embodiment of this invention preferably shows an oxygen transmission rate after heat treatment at 121° C. for 30 minutes (mL/(0.21 atm·day·package)) of 0.00100 mL/(0.21 atm·day·package) or smaller, more preferably 0.00090 mL/(0.21 atm·day·package) or smaller, even more preferably 0.00032 mL/(0.21 atm·day·package) or smaller, and yet more preferably 0.00029 mL/(0.21 atm·day·package) or smaller. The lower limit value of oxygen transmission rate is preferably 0 mL/(0.21 atm·day·package), but may be practical enough even if it is 0.00025 mL/(0.21 atm·day·package) or above. Method for measuring the oxygen transmission rate after heat treatment will follow a method described later in EXAMPLES.

The multilayer vessel according to the fourth embodiment of this invention preferably shows a difference between the oxygen transmission rate measured at 23° C. with a relative humidity inside the multilayer vessel of 100%, and with a relative humidity outside the multilayer vessel of 50%, and the oxygen transmission rate measured after heat treatment at 121° C. for 30 minutes, of 0.00005 mL/(0.21 atm·day·package) or smaller, more preferably 0.00004 mL/(0.21 atm·day·package) or smaller, and even more preferably 0.00003 mL/(0.21 atm·day·package) or smaller. In particular in this invention, with the polyamide resin (A) that contains 20 to 200 ppm by mass of phosphorus atom, and contains calcium atom so that the molar ratio given by (phosphorus atom):(calcium atom) will be 1:0.3 to 0.7, it now becomes possible to improve the oxygen transmission rate after heat treatment.

<<Water Vapor Transmission Rate (WVTR)>>

The multilayer vessel according to the fourth embodiment of this invention preferably has a water vapor transmission rate (WVTR) of 0.0009 g/(day·package) or smaller, which is more preferably 0.0008 g/(day·package) or smaller. The lower limit value of water vapor transmission rate is preferably 0 g/(day·package), but may be practical enough even if it is 0.0005 g/(day·package) or above. The water vapor transmission rate may be measured according to the method described later in EXAMPLES.

The fifth embodiment of the multilayer vessel of this invention relates to a bio-pharmaceutical vessel. More specifically, the bio-pharmaceutical vessel of the fifth embodiment is the one for storing a protein-derived medicinal component, wherein the vessel includes the layer (X) that contains at least one type of polyolefin resin as the major ingredient, and the layer (Y) that contains the polyamide resin (A) as the major ingredient; the polyamide resin (A) is composed of a structural unit derived from diamine, and a structural unit derived from dicarboxylic acid; 70 mol % or more of the structural unit derived from diamine is derived from metaxylylenediamine; meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid.

The polyamide resin (A) is usually an amorphous polyamide resin. By using such polyamide resin, the bio-pharmaceutical vessel will have excellent gas barrier performance and transparency even after heat sterilization. The vessel will also be able to keep a high level of medical efficacy of a medicine that contains a protein-derived medicinal component.

<Layer Structure>

The layer structure of the bio-pharmaceutical vessel according to the fifth embodiment of this invention is synonymous to that in the basic mode of the multilayer vessel of this invention, and the same will apply to preferable ranges.

In particular in the bio-pharmaceutical vessel according to the fifth embodiment of this invention, at least one layer of the outer layer is preferably thicker than at least one layer of the inner layer. Difference of the thickness between the outer layer and the inner layer is preferably 200 μm or larger, more preferably 300 μm or larger, and even more preferably 300 to 900 μm.

The total thickness of the bio-pharmaceutical vessel according to the fifth embodiment of this invention is preferably 0.5 mm or above at the smallest, more preferably 0.8 mm or above, and even more preferably 1.0 mm or above. The total thickness is preferably 2.5 mm or below, and more preferably 2.0 mm or below.

<Layer (X)>

The layer (X) in the fifth embodiment of this invention is synonymous to that in the basic mode of the multilayer vessel, and the same will apply to preferable ranges. In particular, the polyolefin resin that composes the layer (X) is preferably at least one type of cycloolefin-based polymer. In this embodiment, also employable are polyolefin resins described in paragraphs [0101] to [0103] of JP-A-2014-068767, the contents of which are incorporated by reference into this specification.

<Layer (Y)>

The layer (Y) in the fifth embodiment of this invention is synonymous to that in the basic mode of the multilayer vessel, and the same will apply to preferable ranges.

<Physical Properties of Bio-pharmaceutical Vessel>

The bio-pharmaceutical vessel according to the fifth embodiment of this invention preferably has the individual physical properties including haze, total light transmittance, YI, and oxygen transmission rate (OTR) controlled within the ranges described below, and in particular, has all of these properties well controlled within these ranges.

<<Haze>>

The bio-pharmaceutical vessel according to the fifth embodiment of this invention preferably has a haze (%) after heat treatment at 121° C. for 30 minutes of 6% or smaller, more preferably 5% or smaller, and even more preferably 4% or smaller. The lower limit value of haze is preferably 0%, but may be practical enough even if it is 2% or above, and further 3% or above. Method for measuring the haze (%) after heat treatment at 121° C. for 30 minutes will follow a method described later in EXAMPLES.

<<Total Light Transmittance>>

The bio-pharmaceutical vessel according to the fifth embodiment of this invention preferably has a total light transmittance (%) after heat treatment at 121° C. for 30 minutes of 71% or larger, which is more preferably 73% or larger, even more preferably 75% or larger, yet more preferably 80% or larger, and furthermore preferably 85% or larger. The upper limit value of total light transmittance is preferably 100%, but may be practical enough even if it is 95% or below, further 93% or below, and particularly 90% or below. Method for measuring the total light transmittance (%) after heat treatment at 121° C. for 30 minutes will follow a method described later in EXAMPLES.

<<YI>>

The bio-pharmaceutical vessel according to the fifth embodiment of this invention preferably has a YI value after heat treatment at 121° C. for 30 minutes of 8 or smaller, which is more preferably 6 or smaller, and even more preferably 5 or smaller. The lower limit value of YI value is preferably 0, but may be practical enough even if it is 2 or above, further 3 or above, and particularly 4 or above. Method for measuring the YI value after heat treatment at 121° C. for 30 minutes will follow a method described later in EXAMPLES.

<<Oxygen Transmission Rate (OTR)>>

The bio-pharmaceutical vessel according to the fifth embodiment of this invention preferably shows an oxygen transmission rate (OTR), measured at 23° C. with a relative humidity inside bio-pharmaceutical vessel of 100%, and a relative humidity outside the bio-pharmaceutical vessel of 50%, of 0.00100 mL/(0.21 atm·day·package) or smaller, which is more preferably 0.00030 mL/(0.21 atm·day·package) or smaller. The lower limit value of oxygen transmission rate is preferably 0 mL/(0.21 atm·day·package), but may be practical enough even if it is 0.00025 mL/(0.21 atm·day·package) or above. Method for measuring the oxygen transmission rate will follow a method described later in EXAMPLES.

The bio-pharmaceutical vessel according to the fifth embodiment of this invention preferably shows an oxygen transmission rate (mL/(0.21 atm·day·package)) after heat treatment at 121° C. for 30 minutes of 0.00100 mL/(0.21 atm·day·package) or smaller, more preferably 0.00090 mL/(0.21 atm·day·package) or smaller, even more preferably 0.00030 mL/(0.21 atm·day·package) or smaller, and yet more preferably 0.00028 mL/(0.21 atm·day·package) or smaller. The lower limit value of oxygen transmission rate is preferably 0 mL/(0.21 atm·day·package), but may be practical enough even if it is 0.00025 mL/(0.21 atm·day·package) or above. Method for measuring the oxygen transmission rate after heat treatment will follow a method described later in EXAMPLES.

The bio-pharmaceutical vessel according to the fifth embodiment of this invention preferably shows a difference between the oxygen transmission rate measured at 23° C. with a relative humidity inside bio-pharmaceutical vessel of 100%, and with a relative humidity outside the bio-pharmaceutical vessel of 50%, and the oxygen transmission rate of the bio-pharmaceutical vessel of the fifth embodiment measured after heat treatment at 121° C. for 30 minutes, of 0.00005 mL/(0.21 atm·day·package) or smaller, which is more preferably 0.00003 mL/(0.21 atm·day·package) or smaller, and even more preferably 0.00002 mL/(0.21 atm·day package) or smaller.

<Specific Examples of Bio-Pharmaceutical Vessel>

Type of the bio-pharmaceutical vessel according to the fifth embodiment of this invention may be any of known ones including vial, syringe, ampule and so forth, without special limitation. The bio-pharmaceutical vessel of this invention is preferably a vial.

Next, the bio-pharmaceutical vessel according to the fifth embodiment of this invention will be explained with reference to a vial, and referring to FIG. 2. Note that, the bio-pharmaceutical vessel of the fifth embodiment is, of course, not limited to the one illustrated in FIG. 2.

FIG. 2 is a schematic drawing illustrating a structure of the vial, as one exemplary vessel according to the fifth embodiment of this invention, wherein reference numeral 11 stands for the vial, 12 for a packing 13 for a cap, and 14 for a medicine. In this invention, by using the vessel with the above-described layer structure for the vial 11, the vessel will less likely be whitened even after stored for a certain period of time with a chemical liquid filled therein, and will keep a high medical efficacy of a medicine to be contained therein.

The vial 11 in the fifth embodiment of this invention preferably has a height (H) of 10 to 80 mm, which is more preferably 20 to 60 mm. The height (H) of the vial in this invention is given, as illustrated in FIG. 2, by a height measured from the bottom to the opening.

The vial 11 in the fifth embodiment of this invention is (a part to be filled with medicine) is preferably cylindrical. The vial 11 in the fifth embodiment of this invention, when given a cylindrical form, preferably has an outer diameter (D) of 2 to 40 mm, which is more preferably 5 to 30 mm. The outer diameter (D) of the vial of this invention, whose body is given a cylindrical form, means the outer diameter of the cylinder.

In the bio-pharmaceutical vessel according to the fifth embodiment of this invention, the residual space beside the medicine is preferably filled with nitrogen gas.

The packing 12 is not specifically limited so long as it can seal the vial. The material is exemplified by rubber.

The cap 13 acts to hold the packing, and is typically made of metal. Alternatively, the packing is omissible by employing a valve seal structure.

Still alternatively, the bio-pharmaceutical vessel according to the fifth embodiment of this invention may have a vial threaded around the opening, to be fitted with a cap.

<Bio-Pharmaceutical>

The bio-pharmaceutical relevant to the fifth embodiment of this invention is not specifically limited so long as it contains a protein-derived medicinal component, and is widely selectable from bio-pharmaceuticals known to the skilled persons. More specifically, the bio-pharmaceutical is preferably selected from the group consisting of antibody, hormone, enzyme, and complexes containing them.

Specific examples of bio-pharmaceutical include adrenalin antagonist, analgesic, anesthetic, angiotensin antagonist, anti-inflammatory drug, anti-anxiety drug, anti-arrhythmic drug, anticholinergic, anticoagulant, anticonvulsant, antidiarrheal, antihistamine, antineoplastic drug and antimetabolite, antineoplastic drug and antimetabolite, anti-plastic drug, antiulcer drug, bisphosphonate, bronchodilator, cardiotonic, cardiovascular drug, CNS-acting α2 stimulant, contrast agent, converting enzyme inhibitor, dermatologic agent, diuretic, erectile dysfunction drug, drug of abuse, endothelin antagonist, hormone drug and cytokine, hypoglycemic drug, uricosuric drug and gout suppressant, immunosuppressive drug, hypolipidemic drug, various chemicals, psychotherapeutic drug, renin inhibitor, serotonin antagonist, steroid, sympathomimetic drug, thyroid drug and antithyroid drug, and vasodilator, vasopeptidase inhibitor, insulin, blood factor, thrombolytic drug, hormone, hematopoietic growth factor, interferon, interleukin system product, vaccine, monoclonal antibody, tumor necrosis factor, therapeutic enzyme, antibody-drug complex, biosimilar, erythropoietin, immunoglobulin, somatic cell, gene therapeutic drug, tissue, and recombinant therapeutic protein.

The bio-pharmaceutical may be liquid, solid, or liquid-solid mixture.

<Method for Manufacturing Multilayer Vessel>

Method for molding the multilayer vessel according to the basic mode of this invention is suitably selected depending on applications. It is preferably manufactured by injection molding or injection blow molding.

Injection blow molding is advantageous in that the obtainable multilayer vessel (injection blow molded article) will be less likely to deform even after sterilized under high pressure steam, will effectively be suppressed from whitening, and will keep a high level of barrier performance. In injection blow molding, first a test tube-like preform (parison) is molded by injection molding, the preform that is kept properly heated is then placed in mold (blow molding dies) corresponded to the final geometry, air is blown therein through the neck to expand the preform so as to match the mold, and then cooled to solidify, to obtain a bottle-like product.

The preform may be molded by any of well-known methods for injection molding.

For example, using a molding machine equipped with two or more injection units and injection mold, a material for composing the layer (X) and a material for composing the layer (Y) are independently injected from the individual injection cylinders through hot runners of the dies into a cavity. A multilayer preform, whose shape is corresponded to the shape of the injection mold, is thus manufactured.

Alternatively, first a material for composing the layer (X) may be injected through an injection cylinder, next a material for composing the layer (Y) may be injected through other injection cylinder concurrently with the resin for composing the layer (X), and further a necessary amount of the material for composing the layer (X) may be injected to fill the cavity, to thereby obtain a three-layered multilayer preform with an X/Y/X structure.

Still alternatively, first a material for composing the layer (X) may be injected, next a material for composing the layer (Y) may be injected through other injection cylinder solely by itself, and lastly a necessary amount of the material for composing the layer (X) may be injected to fill the cavity, to thereby obtain a five-layered multilayer preform with an X/Y/X/Y/X structure.

In the process of blow molding, the above-described mold corresponded to the final geometry are preferably heated to 120 to 170° C., more preferably heated to 130 to 160° C. Against the inner wall of the mold, the outer wall of the molded article is brought into contact for a predetermined period of time.

According to another method for manufacturing a blow-molded article, employable is two-step blow molding, according to which a multilayer preform is manufactured using primary stretch blow mold, so as to obtain a primary blow molded article which is larger than the final blow molded article, the primary blow molded article is then allowed to shrink under heating, and further subjected to stretch blow molding in secondary dies to obtain a final blow molded article. According to such method for manufacturing a blow molded article, the obtainable blow molded article will have a thoroughly stretched and thinned bottom, and will excel in deformation and impact resistance of the bottom during hot filling or heat sterilization.

In particular, a preferred method for manufacturing a multilayer vessel according to the first embodiment includes molding a multilayer preform by individually injecting the layer (X) that contains the cycloolefin-based polymer (B) as the major ingredient, and the layer (Y) that contains the polyamide resin (A) as the major ingredient, to thereby form a multilayer preform, and, molding the multilayer preform by blow molding; wherein the polyamide resin (A) is composed of a structural unit derived from diamine and a structural unit derived from dicarboxylic acid, 70 mol % or more of the structural unit derived from diamine is derived from metaxylylenediamine; meanwhile 30 to 60 mol % of the structural unit derived from dicarboxylic acid is derived from a straight chain aliphatic α,ω-dicarboxylic acid having 4 to 20 carbon atoms, and 70 to 40 mol % is derived from isophthalic acid; the cycloolefin-based polymer (B) has a glass transition temperature of 50 to 170° C.; the polyamide resin (A) has a glass transition temperature of 100 to 160° C.; the cycloolefin-based polymer (B) shows a melt viscosity of 100 to 250 Pa·sec at one or more temperatures between 260 and 300° C., under a shear rate of 1216 sec$^{-1}$; and the polyamide resin (A) shows a melt viscosity of 200 to 400 Pa·sec at 270° C., under a shear rate 1216 sec$^{-1}$.

The layer (X) and the layer (Y) are respectively synonymous to the layer (X) and the layer (Y) of the multilayer vessel of the first embodiment, and the same will apply to preferable ranges.

In method for manufacturing a multilayer vessel of the first embodiment, temperature of the injection cylinder for layer (X) is preferably 200 to 350° C., and more preferably 250° C. to 330° C. Temperature of the injection cylinder for layer (Y) is preferably 200 to 330° C., and more preferably 230 to 300° C. Difference between the temperature of injection cylinder for layer (X), and the temperature of injection cylinder for layer (Y), is preferably 0 to 100° C., more preferably 0 to 50° C., and even more preferably 0 to 40° C.

Within these ranges, it now becomes possible to reduce difference between temperature of the resin flow path in co-extrusion mold, and temperature of the cylinders for layer (X) and layer (Y). Effects of improving moldability and appearance will therefore be demonstrated in a more effective manner.

Temperature of the resin flow path in injection dies is preferably 200 to 350° C., and more preferably 250 to 330° C. Temperature of the injection dies is preferably 0 to 140° C., and more preferably 20° C. to 100° C.

The polyamide resin, when fed into the injection cylinder, preferably has a moisture content of 0 to 1000 ppm by mass, which is more preferably 0 to 500 ppm by mass.

Within these ranges, the molded article will tend to have an improved appearance.

The multilayer vessel of the first embodiment is usually an unstretched article, although it may be stretched.

The blow mold are preferably kept at 10 to 30° C. Within the range, the effect of this invention will more effectively be demonstrated.

The multilayer syringe barrels for prefilled syringe according to the second embodiment and the third embodiment of this invention are preferably manufactured by injection molding.

For example, using a molding machine equipped with two or more injection units and injection mold, a material for composing the layer (X) and a material for composing the layer (Y) are independently injected from the individual injection cylinders through hot runners of the mold into a cavity. A multilayer syringe barrel, whose shape is corresponded to the shape of injection mold, is thus manufactured.

Alternatively, first a material for composing the layer (X) may be injected through an injection cylinder, next a material for composing the layer (Y) may be injected through other injection cylinder concurrently with the resin for composing the layer (X), and further a necessary amount of the material for composing the layer (X) may be injected to fill the cavity, to thereby obtain a three-layered multilayer syringe barrel with an X/Y/X structure.

Still alternatively, first a material for composing the layer (X) may be injected, next a material for composing the layer (Y) may be injected through other injection cylinder solely by itself, and lastly a necessary amount of the material for composing the layer (X) may be injected to fill the cavity, to thereby obtain a five-layered multilayer syringe barrel with an X/Y/X/Y/X structure.

The multilayer syringe barrel used in this invention is usually an unstretched article, although it may be stretched.

The multilayer vessel according to the fourth embodiment of this invention is preferably manufactured by direct blow molding. By employing direct blow molding, it now becomes possible to reduce the total thickness of the multilayer vessel, in particular, the thickness of the layer (X).

That is, this invention discloses a method for manufacturing a multilayer vessel, which includes conducting direct blow molding, using a material that composes the layer (X) containing at least one type of polyolefin resin as the major ingredient, a material that composes the adhesive layer, and, a material that composes the layer (Y) containing the polyamide resin (A) as the major ingredient; the polyamide resin (A) is composed of a structural unit derived from diamine and a structural unit derived from dicarboxylic acid; 70 mol % or more of the structural unit derived from diamine is derived from metaxylylenediamine; meanwhile 30 to 60 mol % of the structural unit derived from dicarboxylic acid is derived from a straight chain aliphatic α,ω-dicarboxylic acid having 4 to 20 carbon atoms, and 70 to 40 mol % is derived from isophthalic acid. The material that composes the layer (X) containing at least one type of polyolefin resin, the material that composes the adhesive layer, and the material that composes the layer (Y) containing the polyamide resin (A) as the major ingredient, are respectively composed of the materials having been explained previously regarding the layer (X), the layer (Y) and the adhesive layer, and the same will apply to the amounts of addition, etc. of the individual ingredients.

In an exemplary method of direct blow molding, by using a multilayer direct blow molding machine equipped with a plurality of extrusion units and molds, a multilayer parison that contains a material for composing the layer (X), a material for composing the layer (Y), and a material for composing the adhesive layer is formed, the parison is then extruded into a tubular form, held between the molds, and blown from the bottom to be expanded. In a preferred embodiment, the multilayer parison is composed solely of the material for composing the layer (X), the material for composing the layer (Y), and the material for composing the adhesive layer. Geometry of the dies may be determined depending on the multilayer vessel to be formed, and is typically cylindrical. In this invention, it is preferable to extrude the multilayer parison into a tubular form, to hold the multilayer parison between the dies conditioned at 10° C. to 80° C., to pinch off the bottom of parison and thereby allow it to fuse, and to blow the multilayer parison with a high pressure air or the like before being cooled down, to thereby expand the parison into a bottle or into other vessel form suited to the mode of usage.

The direct blow molding machine is not specifically limited, and may be a machine having a single set of cylindrical dies and a single set of molds; a machine having a plurality of sets of dies and a plurality of molds; or a rotary-type direct blow molding machine.

Also employable is an in-mold labelling method by which a label is preliminarily inserted in the molds, to finally place it on the surface of vessel. Not only for the case of in-mold labelling, but for all cases where the label is placed, the label is preferably subjected to flame treatment or corona treatment prior to the placement. It is also possible to create a frosty appearance, by treating inside of the molds by sand blasting.

Regarding the direct blow molding, the descriptions in JP-A-2015-217971 and JP-B2-5895935 may be referred to, the contents of which are incorporated by reference into this specification.

The multilayer vessel according to the basic mode of this invention may be coated with an evaporated film composed of an inorganic substance or inorganic oxide, or with an amorphous carbon film.

The inorganic substance or inorganic oxide is exemplified by aluminum, alumina, and silicon oxide. The evaporated film composed of the inorganic substance or inorganic oxide can block any eluate such as acetaldehyde, formaldehyde and so forth from the multilayer vessel of this invention. Method for forming the evaporated film is not specifically limited, and is exemplified by physical vapor deposition methods such as vacuum evaporation, sputtering and ion plating; and chemical vapor deposition methods such as PECVD. The evaporated film preferably has a thickness of 5 to 500 nm, from the viewpoint of gas barrier performance, light shielding performance and flex resistance, which is more preferably 5 to 200 nm.

The amorphous carbon film is a sort of diamond like carbon film, which is a hard carbon film also called i-carbon film or hydrogenated amorphous carbon film. In an exemplary method for forming the film, the inside of a hollow molded article is evacuated, a carbon source gas is fed therein, and plasma-producing energy is input to excite the carbon source gas to produce a plasma. In this way, the amorphous carbon film may be formed on the inner surface of the multilayer vessel. The amorphous carbon film not only can distinctively reduce permeability of low-molecular inorganic gases such as oxygen and carbon dioxide, but also can suppress sorption of various odorous low molecular organic compounds. The amorphous carbon film is preferably 50 to 5000 nm thick, from the viewpoints of effect of suppressing sorption of low molecular organic compounds, effect of improving the gas barrier performance, adhesiveness with plastics, durability, and transparency.

The multilayer vessel according to the basic mode of this invention is suitable for usage as medical packaging, in particular as ampule, vial, cartridge, or prefilled syringe, and preferably as ampule, vial and prefilled syringe. "Usage as medical packaging" means that the vessel is used for packaging medicine, quasi-drug or medical supplies. The multilayer vessel of this invention is also suitably used as an infusion vessel.

The multilayer vessel of the first embodiment is preferably a vial.

The multilayer vessel according to the basic mode of this invention, and in particular, the multilayer vessel of the first embodiment can store various types of medicine and quasi-drug. Medicine is preferably stored. The medicine and quasi-drug may be liquid, solid, or mixture of liquid and solid.

The multilayer vessel according to the fourth embodiment of this invention is preferably used particularly for medical packaging.

The multilayer vessel according to the fourth embodiment of this invention is particularly suitable as ampule, vial, prefilled syringe, vacuum blood collection tube and infusion vessel (also referred to as infusion bag), and is more suitable as an infusion vessel.

The multilayer vessel for medical packaging according to this invention, when used as the infusion vessel, preferably has a capacity of 10 to 1000 mL for example, which may be 50 to 700 mL, and may particularly be 80 to 700 mL.

Geometry of the multilayer vessel of this invention is exemplified by a bottle which has a bottom, and a cylindrical or polyhedral columnar trunk.

In particular, the multilayer vessel used in this invention is preferably self-supportable. "Self-supportable" means that the bottle, after allowed to stand still in an atmosphere at 25° C. with a relative humidity of 35%, for one week, neither deforms nor falls. The aforementioned bottle is specifically exemplified.

The multilayer vessel of this invention can store various types of medicine. For more details, paragraph [0100] of JP-A-2014-148076 may be referred to, the content of which is incorporated by reference into this specification.

The multilayer vessel according to the basic mode of this invention is intended to be heat sterilized. Method for heat sterilization is exemplified by those using a steam system, hot water bath system, and shower system. Sterilization temperature preferably falls within the range from 80° C. to 140° C., and sterilization time preferably falls within the range from 10 to 120 minutes.

In particular, the multilayer syringe barrel for prefilled syringe according to the second embodiment is preferably heat sterilized. Heat sterilization is preferably given by using high energy radiation (gamma ray or electron beam, for example), or ethylene oxide gas (EOG). The multilayer syringe barrel for prefilled syringe according to the second embodiment may be heat sterilized, but has better not be sterilized at 100° C. or above, and further 90° C. or above.

The multilayer syringe barrel for prefilled syringe according to the third embodiment, and the bio-pharmaceutical vessel according to the fifth embodiment are preferably sterilized. The sterilization is preferably given by using high energy radiation (gamma ray or electron beam, for example), or ethylene oxide gas (EOG). The multilayer syringe barrel for prefilled syringe of this invention is also preferably heat sterilized. Heat sterilization temperature is 100° C. or above, and preferably 110° C. or above. The heat sterilization temperature is typically 150° C. or below, at the highest. Heat sterilization time is preferably 10 minutes to 1 hour.

<Multilayer Article>

The multilayer article of this invention includes the layer (X) that contains at least one type of polyolefin resin as the major ingredient, and a layer (Y) that contains a polyamide resin (A) as the major ingredient; the polyamide resin (A) is composed of a structural unit derived from diamine, and a structural unit derived from dicarboxylic acid; wherein 70 mol % or more of the structural unit derived from diamine is derived from metaxylylenediamine, meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid. The aforementioned multilayer preform is exemplified as an exemplary multilayer article. The multilayer article of this invention is preferably used as a wrapping sheet.

The layer (X) and the layer (Y) are respectively synonymous to the layer (X) and the layer (Y) in the aforementioned multilayer vessel, and the same will apply to preferable ranges.

In particular, the polyamide resin (A) in the multilayer article of this invention preferably contains calcium atom, and more preferably contains 20 to 200 ppm by mass of phosphorus atom, so that the molar ratio given by (phosphorus atom):(calcium atom) will be 1:0.3 to 0.7.

The first embodiment of the multilayer article of this invention includes the layer (X) that contains at least one type of cycloolefin-based polymer as the major ingredient, and the layer (Y) that contains a polyamide resin (A) as the major ingredient; the polyamide resin (A) is composed of a structural unit derived from diamine, and a structural unit derived from dicarboxylic acid; wherein 70 mol % or more of the structural unit derived from diamine is derived from metaxylylenediamine, meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid; the cycloolefin-based polymer (B) has a glass transition temperature of 50 to 170° C.; the polyamide resin (A) has a glass transition temperature of 100 to 160° C.; the cycloolefin-based polymer (B) shows a melt viscosity of 100 to 250 Pa·sec at one or more temperatures between 260 and 300° C., under a shear rate of 1216 $sec^{-1}$; and the polyamide resin (A) shows a melt viscosity of 200 to 400 Pa·sec at 270° C., under a shear rate 1216 $sec^{-1}$.

The second embodiment of the multilayer article of this invention includes the layer (X) that contains at least one type of polyolefin resin as the major ingredient, and the layer (Y) that contains a polyamide resin (A) as the major ingredient, arranged in this order; wherein the polyamide resin (A) is composed of a structural unit derived from diamine, and a structural unit derived from dicarboxylic acid; wherein 70 mol % or more of the structural unit derived from diamine is derived from metaxylylenediamine, meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid.

<Method for Storing Bio-Pharmaceutical>

This invention also discloses a method for storing a bio-pharmaceutical that contains a protein-derived medicinal component using a vessel; wherein the vessel includes the layer (X) that contains at least one type of polyolefin resin as the major ingredient, and the layer (Y) that contains a polyamide resin (A) as the major ingredient; the polyamide resin (A) is composed of a structural unit derived from diamine, and a structural unit derived from dicarboxylic acid, 70 mol % or more of the structural unit derived from diamine is derived from metaxylylenediamine, meanwhile 30 to 60 mol % of the structural unit derived from dicarboxylic acid is derived from straight chain aliphatic α,ω-dicarboxylic acid having 4 to 20 carbon atoms, and 70 to 40 mol % is derived from isophthalic acid.

Details of the vessel are same as those for the aforementioned bio-pharmaceutical vessel. Also details of the bio-pharmaceutical are same as described above.

The bio-pharmaceutical is preferably stored in the vessel so that the filling ratio exceeds 0% by volume and does not exceed 70% by volume. The vessel is preferably filled also with nitrogen, together with the bio-pharmaceutical. Storage temperature of bio-pharmaceutical may suitable be determined depending on types of bio-pharmaceutical, which is typically 2 to 8° C.

<Article that Includes Bio-Pharmaceutical Contained in Bio-Pharmaceutical Vessel>

This invention also discloses an article that includes the bio-pharmaceutical vessel of this invention, and a bio-pharmaceutical contained in the bio-pharmaceutical vessel. Now "contained in . . . vessel" means that the bio-pharmaceutical is stored or enclosed in the vessel. Details of the bio-pharmaceutical vessel and the bio-pharmaceutical are same as described above. The vessel is preferably filled with nitrogen, together with the bio-pharmaceutical. The bio-pharmaceutical is preferably filled in the vessel, so that the content thereof exceeds 0% by volume and does not exceed 70% by volume in the vessel.

<Method for Manufacturing Article Having Vessel and Bio-Pharmaceutical Contained Therein>

This invention also discloses a method for manufacturing an article having a vessel and a bio-pharmaceutical contained therein; the method includes enclosing a bio-pharmaceutical that contains a protein-derived medicinal component; the vessel includes the layer (X) that contains at least one type of polyolefin resin as the major ingredient, and the layer (Y) that contains the polyamide resin (A) as the major ingredient; wherein the polyamide resin (A) is composed of a structural unit derived from diamine, and a structural unit derived from dicarboxylic acid; 70 mol % or more of the structural unit derived from diamine is derived from metaxylylenediamine; meanwhile 30 to 60 mol % of the structural unit derived from dicarboxylic acid is derived from straight chain aliphatic α,ω-dicarboxylic acid having 4 to 20 carbon atoms, and 70 to 40 mol % being derived from isophthalic acid.

Details of the vessel are same as those of the aforementioned bio-pharmaceutical vessel. Also details of the bio-pharmaceutical are same as those described above.

The bio-pharmaceutical, when enclosed in the vessel, is preferably filed so that the content thereof exceeds 0% by volume and does not exceed 70% by volume in the vessel. The vessel is preferably filled also with nitrogen, together with the bio-pharmaceutical. Storage temperature of bio-pharmaceutical may suitable be determined depending on types of bio-pharmaceutical, which is typically 2 to 8° C. The bio-pharmaceutical is preferably filled into the vessel under aseptic conditions. It is also preferable to sterilize the vessel before being filled with the bio-pharmaceutical.

The article that includes the bio-pharmaceutical contained in the inventive vessel may entirely be enclosed in a case and stored. The case is exemplified by cartons made of paper or plastics. Also cases capable of keeping the contents at temperatures different from the outer temperature, such as cooler case and thermostat case, are suitably used as the case.

EXAMPLES

This invention will more specifically be explained referring to Examples. Materials, amounts of consumption, ratios, details of processes and procedures of processes are suitably modified without departing from the spirit of this invention. The scope of this invention is, therefore, by no means limited to the specific Examples below.

(1) Relative Viscosity

Precisely weighed was 0.2 g of polyamide resin, and was then dissolved in 20 mL of a 96% by mass aqueous sulfuric acid solution at 25° C. After the polyamide resin was completely dissolved, 5 mL of the solution is immediately sampled into a Cannon-Fenske viscometer, allowed to stand in a thermostatic chamber at 25° C. for 10 minutes, and the drop time (t) was measured. Also drop time (t0) of the 96% by mass aqueous sulfuric acid solution per se was measured in the same way. The relative viscosity was calculated using t and t0, based on the equation below:

Relative viscosity=$t/t0$.

(2) Oxygen Transmission Rate (OTR) of Multilayer Vessel

Oxygen transmission rate (OTR) of the multilayer vessel at 23° C. with a relative humidity inside the multilayer vessel of 100%, and with a relative humidity outside the multilayer vessel of 50%, was measured in accordance with ASTM D3985, using an oxygen transmission rate measuring instrument ("OX-TRAN (registered trademark) 2/61", from MOCON Inc.). The smaller the measured value, the better the oxygen barrier performance.

(3) Water Vapor Transmission Rate (WVTR) of Multilayer Vessel

Water vapor transmission rate (WVTR) at 40° C. with a relative humidity outside the multilayer vessel of 0% was measured on the 10th day after the start of measurement. A water vapor transmission rate measuring instrument ("PERMATRAN-W (registered trademark) 3/33G", from MOCON Inc.) was used for the measurement. The smaller the measured value, the better the water vapor barrier performance.

(4) Heat Treatment at 121° C. for 30 Minutes (Heat Sterilization, In-Vessel Heating)

The multilayer vessel was heat treated (in-vessel heating) at 121° C. for 30 minutes, in an autoclave ("SR-240", from Tomy Seiko Co., Ltd.). The heating time excludes times for temperature elevation and cooling.

(5) Transparency of Multilayer Vessel (Haze and Total Light Transmittance)

A side wall portion of the multilayer vessel was cut out, and subjected to measurement of haze and total light transmittance. The haze was measured in accordance with JIS K7136. The total light transmittance was measured in accordance with JIS K7375. A measuring instrument employed was a color-turbidity meter ("COH-300A", from Nippon Denshoku Industries, Ltd.). The thickness of the side wall portion of the multilayer vessel, where the measurement was made, was determined, and the measured haze was converted assuming the thickness as 300 μm.

(6) Hue of Multilayer Vessel

A side wall portion of the multilayer vessel was cut out, and subjected to measurement of yellowness index (YI value). A measuring instrument employed was a color-turbidity meter ("COH-300A", from Nippon Denshoku Industries, Ltd.).

(7) Oil Resistance Test of Multilayer Vessel

Into the multilayer vessel, 10 mL of Nisshin MCT Oil (100% medium-chain fatty acid triglycerides (carbon atoms number of the chain of fatty acid triglycerides is 8 to 12)) was injected, and stored at 40° C. for six months. The multilayer syringe barrel was handled so that the hub was sealed with a rubber cap, the oil was injected, and then the flange side was sealed with a gasket.

The multilayer vessels showing no change in the appearance were marked with "○", and those showing oil leakage were marked with "x".

(8) Method for Measuring Phosphorus Atom Concentration and Calcium Atom Concentration Into a TFM-modified PTFE (from 3M Company) vessel, placed were 0.2 g of polyamide resin and 8 mL of a 35% by mass aqueous nitric acid solution, and the content was subjected to microwave digestion in ETHOS One from Milestone General K.K., at an internal temperature of 230° C. for 30 minutes. The digested liquid was then diluted with ultrapure water up to a predetermined volume, to be used as a sample liquid for ICP measurement. The phosphorus atom concentration and the calcium atom concentration were measured using ICPE-9000 from Shimadzu Corporation.

(9) Method for Measuring Melt Viscosity

The melt viscosity was measured using a capillary rheometer at 300° C. or 260° C. at a shear rate 1216 sec$^{-1}$ for the cycloolefin-based polymer (B), and at 270° C. and a shear rate of 1216 sec$^{-1}$ for the polyamide resin (A).

The capillary rheometer employed was "Capilograph 1D" from Toyo Seiki Seisaku-sho, Ltd.

(10) Method for Measuring Glass Transition Temperature

The glass transition temperature was measured in accordance with JIS K7122. A measuring instrument employed was differential scanning calorimeter (DSC) ("DSC-60" from Shimadzu Corporation). Measurement conditions for DSC were as below:

Measuring instrument: "DSC-60", from Shimadzu Corporation

Start temperature for measurement: 25° C.

Heating rate: 10° C./min

End point temperature: 220° C.

Cooling rate: 5° C./min.

(11) Method for Measuring Moisture Content of Polyamide Resin

The moisture content was measured using a trace level water content titrator AQ-2000 from Hiranuma Sangyo Co., Ltd., in a nitrogen atmosphere at 235° C. for 30 minutes.

(12) Method for Evaluating Appearance

The appearance of the multilayer vessel (bottle part) was visually observed to determine a degree of surface undulation, ascribable to that the interface between the layer X and the layer Y in the three-layered structure being not flat but disturbed, and evaluated on a four-point scale from A to D, where A for the best (no surface undulation), and B, C and D are given in this order as the surface undulation increases. A to C are within a practically acceptable range, whereas D is out of the practically acceptable range.

(13) Method for Evaluating Moldability

The moldability of the multilayer vessel was evaluated based on occurrence of surface irregularity, ascribable to adhesion of a resin component or so at the bottom (which corresponds to the gate part when injected from the dies) of the multilayer vessel (occurrence of "irregularity"). Ratio of the number of the multilayer vessels that were judged to be irregularity-free, relative to the total number of the multilayer vessels produced over three-hour continuous molding, was determined. The ratio was termed "yield ratio" (number of irregularity-free multilayer vessels/total number of multilayer vessels), and was used for judging the moldability.

A: yield ratio≥90%
B: 90%>yield ratio≥70%
C: 70%>yield ratio≥50%
D: 50%>yield ratio

(14) Storage of Multilayer Syringe Barrel with Filled Water

The hub of the multilayer syringe barrel was sealed with a rubber cap, the barrel was filled with water, and the flange side was then sealed with a gasket so as not to leave a space in the multilayer syringe barrel. The multilayer syringe barrel, kept as it is, was stored at 40° C. with a relative humidity of 50%, for three months. The water was then drained.

(15) Storage Test of Adrenalin-Containing Chemical Liquid

Water was added to 500 mg of adrenalin and 1670 mg of sodium pyrosulfite, to prepare 100 mL of colorless clear chemical liquid. The hub of the multilayer syringe barrel was sealed with a rubber cap, the barrel was filled with 1 mL of the thus prepared chemical liquid, and the flange side was then sealed with a gasket so as not to leave a space in the multilayer syringe barrel. The multilayer syringe barrel, kept as it is, was stored at 30° C. with a relative humidity of 50%, for six months, and thereafter the hue of the chemical liquid was visually observed.

The chemical liquid, looked colorless and clear immediately after preparation, would yellow if adrenalin were oxidized.

(16) Self-Supportability

The multilayer vessel (bottle) was allowed to stand still, with its bottom directed downward, at 25° C. with a relative humidity of 35% for one week, and evaluated as below.
A: Multilayer bottle was neither deformed nor collapsed.
B: Multilayer found to be other than "A".

(17) Storage Test of Bio-pharmaceutical (Retention Rate of Antibody Activity)

(Method for Measuring Binding Ratio)

An isothermal titration calorimeter was used. A 5 μM antigen solution (FGF1-Mouse, from Biological Industries, Inc.) was filled in a cell, and the binding ratio at 25° C. was measured while adding dropwise 10 μL each of an antibody solution into the cell.

(Storage Test)

Into the bio-pharmaceutical vessel before heat treatment, 1 cc (1 mL) of a 50 μM antibody solution of ANTI FGF1, Monoclonal Antibody (mAb1) from Wako Pure Chemical Industry, Ltd. was injected, and stored at 8° C. with a relative humidity of 50%, for 180 days. The solvent employed was phosphate buffer (pH7.4) from Invitrogen. The binding ratio of the antibody solution, before and after 180-day storage, was measured as described above, and the retention rate of antibody activity before and after storage was determined by the equation below.

Retention Rate of Antibody Activity (%)=(Binding ratio of antibody solution after 180-day storage/Binding ratio of antibody solution before storage)×100

Example 1-1

A polyamide resin listed in Table 1-1 was synthesized, according to the method described below.

Into a reaction vessel equipped with a stirrer, a partial condenser, a total condenser, a thermometer, a dropping funnel, a nitrogen gas feeding tube, and a strand die, placed were 6,000 g (41.06 mol) of precisely weighed adipic acid, 6,821 g (41.06 mol) of isophthalic acid, 10.04 g of calcium hypophosphite ($Ca(H_2PO_2)_2$) (175 ppm by mass of phosphorus atom concentration in the polyamide resin), and 7.26 g of sodium acetate, the system was thoroughly replaced with nitrogen gas and then filled with nitrogen gas up to an inner pressure of 0.4 MPa, and the system was heated to 190° C. under stirring while feeding a small flow rate of nitrogen gas. The molar ratio given by sodium acetate/calcium hypophosphite was set to 1.50.

To the content kept under stirring, 11,185 g (82.12 mol) of metaxylylenediamine was added dropwise, and the system was continuously heated while removing the produced water out of the system. After completion of dropwise addition of metaxylylenediamine, the inner temperature was elevated, and upon reaching 265° C., the inside of the reaction vessel was evacuated, the inner temperature was further elevated and kept at 270° C. for 10 minutes, so as to allow the melt polycondensation to proceed. The system was then replaced with nitrogen gas, the obtained polymer was taken out through the strand die, and pelletized, to obtain approximately 21 kg of polyamide resin (A1) pellets. The polyamide resin (A1) was found to have a glass transition temperature of 128° C., and a relative viscosity of 1.95.

Next, according to the conditions listed below, a material for composing the layer (X) was injected through an injection cylinder, a material for composing the layer (Y) was injected through other injection cylinder concurrently with the resin for composing the layer (X), and further a necessary amount of the material for composing the layer (X) was injected to fill the cavity, to thereby obtain a three-layered multilayer preform (5.1 g) with an X/Y/X structure.

The resin used for composing the layer (X) was a cycloolefin polymer ("ZEONEX (registered trademark) 690R", from ZEON Corporation). The resin used for composing the layer (Y) was the polyamide resin (A1) obtained above.

The thus obtained preform was cooled down to a predetermined temperature, and then subjected to blow molding as a secondary process, wherein the preform was transferred into mold, air was blown therein through the neck to expand the preform so as to match the mold, and then cooled to solidify. A multilayer vessel was thus manufactured.

<<Geometry of Multilayer Vessel>>

Full length=45 mm, outer diameter=24 mm, thickness (total thickness of multilayer vessel, that is, sum of thicknesses of outer layer (X), inner layer (X) and intermediate layer (Y))=1.0 mm, thickness of outer layer (X)=600 μm, thickness of inner layer (X)=200 μm, thickness of intermediate layer (Y)=200 μm. The multilayer vessel was manufactured by injection blow molding, using an integrated injection/blow molding machine (model "ASB-12N/10T", four-cavity type, from Nissei ASB Machine Co., Ltd.).

(Molding Conditions for Multilayer Vessel)
Injection cylinder temperature for layer (X): 300° C.
Injection cylinder temperature for layer (Y): 280° C.
Temperature of resin flow path in injection mold: 300° C.
Blow temperature: 150° C.
Temperature of cooling water for blow mold: 40° C.

Example 1-2

All conducted in the same way as in Example 1-1, except that the molar ratio of adipic acid and isophthalic acid was controlled to 40:60, to obtain polyamide resin (A2) pellets. The polyamide resin (A2) was found to have a relative viscosity of 1.94.

A multilayer vessel was manufactured in the same way as in Example 1-1, except that the polyamide resin (A2) was used in place of the polyamide resin (A1).

Example 1-3

All conducted in the same way as in Example 1-1, except that the molar ratio of adipic acid and isophthalic acid was controlled to 60:40, to obtain polyamide resin (A3) pellets. The polyamide resin (A3) was found to have a relative viscosity of 1.94.

A multilayer vessel was manufactured in the same way as in Example 1-1, except that the polyamide resin (A3) was used in place of the polyamide resin (A1).

Example 1-4

All conducted in the same way as in Example 1-1, except that sodium hypophosphite was used as the hypophosphite salt, to obtain polyamide resin (A4) pellets. The polyamide resin (A4) was found to have a relative viscosity of 1.95.

A multilayer vessel was manufactured in the same way as in Example 1-1, except that the polyamide resin (A4) was used in place of the polyamide resin (A1).

Example 1-5

All conducted in the same way as in Example 1-1, except that the amount of addition of calcium hypophosphite was changed as summarized in Table 1-1, to obtain polyamide resin (A5) pellets. The polyamide resin (A5) was found to have a relative viscosity of 1.93.

A multilayer vessel was manufactured in the same way as in Example 1-1, except that the polyamide resin (A5) was used in place of the polyamide resin (A1).

Example 1-6

All conducted in the same way as in Example 1-1, except that the amount of addition of calcium hypophosphite was changed as summarized in Table 1-1, to obtain polyamide resin (A6) pellets. The polyamide resin (A6) was found to have a relative viscosity of 1.93.

A multilayer vessel was manufactured in the same way as in Example 1-1, except that the polyamide resin (A6) was used in place of the polyamide resin (A1).

Example 1-7

All conducted in the same way as in Example 1-1, except that the amount of addition of calcium hypophosphite was changed as summarized in Table 1-1, to obtain polyamide resin (A7) pellets. The polyamide resin (A7) was found to have a relative viscosity of 1.93.

A multilayer vessel was manufactured in the same way as in Example 1-1, except that the polyamide resin (A7) was used in place of the polyamide resin (A1).

Examples 1-8 to 1-10

Multilayer vessels were manufactured respectively in the same way as in Examples 1-1 to 1-3, except that a cycloolefin copolymer ("TOPAS (registered trademark) 6013S-04", from TOPAS Advanced Polymers GmbH) was used as the resin for composing the layer (X), in place of the cycloolefin polymer ("ZEONEX (registered trademark) 690R", from ZEON Corporation).

Examples 1-11 to 1-13

Multilayer vessels were manufactured respectively in the same way as in Examples 1-1 to 1-3, except that a polypropylene-based polymer ("Bormed RB845MO", from BOREALIS AG) was used as the resin for composing the layer (X), in place of the cycloolefin polymer ("ZEONEX (registered trademark) 690R", from ZEON Corporation).

Comparative Example 1-1

All conducted in the same way as in Example 1-1, except that the molar ratio of adipic acid and isophthalic acid was controlled to 94:6, to obtain polyamide resin (A8) pellets of Comparative Example 1-1. The polyamide resin (A8) was found to have a relative viscosity of 2.65.

A multilayer vessel was manufactured in the same way as in Example 1-1, except that the polyamide resin (A8) was used in place of the polyamide resin (A1).

Comparative Example 1-2

A multilayer vessel was manufactured in the same way as in Example 1-1, except that N-MXD6 ("MX Nylon S6007", from Mitsubishi Gas Chemical Company, Inc., relative viscosity=2.65), which is composed of a metaxylylenediamine unit and an adipic acid unit, was used in place of the polyamide resin (A1).

Comparative Example 1-3

A multilayer vessel was manufactured in the same way as in Example 1-1, except that a polyhexamethylene isophthalamide/polyhexamethylene terephthalamide copolymer ("Novamid (registered trademark) X21", from DSM Japan Engineering Plastics, Inc.) was used in place of the polyamide resin (A1).

Comparative Example 1-4

A multilayer vessel was manufactured in the same way as in Example 1-11, except that an ethylene-vinyl alcohol copolymer ("Eval (registered trademark) F171B", from Kuraray Co., Ltd.) was used in place of the polyamide resin (A1).

The multilayer vessels obtained in Examples 1-1 to 1-13 and Comparative Examples 1-1 to 1-4 were measured regarding the oxygen transmission rate (OTR) and the water vapor transmission rate (WVTR), according to the methods described above. The obtained multilayer vessels were also heat-treated under the conditions described above, and measured regarding the haze, the total light transmittance, the YI value and the oxygen transmission rate (OTR), after heat treatment. The obtained multilayer vessels were also subjected to oil resistance test. Results are summarized in Table 1-1 or Table 1-2.

TABLE 1-1

|  |  |  |  | Example 1-1 | Example 1-2 | Example 1-3 | Example 1-4 | Example 1-5 | Example 1-6 | Example 1-7 |
|---|---|---|---|---|---|---|---|---|---|---|
| Gas Barrier Layer (Y) |  | Inner Layer and Outer Layer (X) |  | COP | COP | COP | COP | COP | COP | COP |
|  | Polyamide Resin (A) | Diamine Unit | Metaxylylenediamine*1 | 100 | 100 | 100 | 100 | 100 | 100 | 100 |
|  |  | Dicarboxylic Acid Unit | Adipic Acid (mol %)*2 | 50 | 40 | 60 | 50 | 50 | 50 | 50 |
|  |  |  | Isophthalic Acid (mol %)*2 | 50 | 60 | 40 | 50 | 50 | 50 | 50 |
|  |  | Type of Hypophosphite |  | Ca Salt | Ca Salt | Ca Salt | Na Salt | Ca Salt | Ca Salt | Ca Salt |
|  |  | Amount of Added Hypophosphite (Phosphorus Atom Concentration, ppm by mass) |  | 175 | 175 | 175 | 175 | 5 | 250 | 25 |
|  |  | Concentration of Phosphorus Atom in Polyamide Resin (ppm by mass) |  | 173.3 | 172.6 | 172.2 | 170.6 | 4.8 | 247.2 | 24.8 |
|  |  | Molar Ratio of Calcium Atom to Phosphorus Atom in Polyamide Resin |  | 0.5 | 0.5 | 0.5 | 0 | 0.5 | 0.5 | 0.5 |
|  | Haze After Heat Treatment at 121° C. for 30 minutes (%) |  |  | 3.2 | 3.1 | 3.6 | 5.8 | 3.3 | 3.9 | 3.2 |
|  | Total Light Transmittance After Heat Treatment at 121° C. for 30 minutes (%) |  |  | 89.1 | 89.0 | 89.3 | 86.9 | 89.8 | 88.9 | 89.1 |
|  | YI After Heat Treatment at 121° C. for 30 minutes |  |  | 4.8 | 4.5 | 4.2 | 4.6 | 7.8 | 5.0 | 5.1 |
|  | OTR (ml/0.21 atm · day · package) |  |  | 0.00027 | 0.00026 | 0.00028 | 0.00027 | 0.00027 | 0.00027 | 0.00027 |
|  | OTR After Heat Treatment at 121° C. for 30 minutes (ml/0.21 atm · day · package) |  |  | 0.00027 | 0.00026 | 0.00028 | 0.00027 | 0.00027 | 0.00027 | 0.00027 |
|  | WVTR (g/day · package) |  |  | 0.0006 | 0.0006 | 0.0006 | 0.0006 | 0.0006 | 0.0006 | 0.0006 |
|  | Oil Resistance Test |  |  | X | X | X | X | X | X | X |

|  |  |  |  | Example 1-8 | Example 1-9 | Example 1-10 | Example 1-11 | Example 1-12 | Example 1-13 |
|---|---|---|---|---|---|---|---|---|---|
| Gas Barrier Layer (Y) |  | Inner Layer and Outer Layer (X) |  | COC | COC | COC | PP | PP | PP |
|  | Polyamide Resin (A) | Diamine Unit | Metaxylylenediamine*1 | 100 | 100 | 100 | 100 | 100 | 100 |
|  |  | Dicarboxylic Acid Unit | Adipic Acid (mol %)*2 | 50 | 40 | 60 | 50 | 40 | 60 |
|  |  |  | Isophthalic Acid (mol %)*2 | 50 | 60 | 40 | 50 | 60 | 40 |
|  |  | Type of Hypophosphite |  | Ca Salt | Ca Salt | Ca Salt | Ca Salt | Ca Salt | Ca Salt |
|  |  | Amount of Added Hypophosphite (Phosphorus Atom Concentration, ppm by mass) |  | 175 | 175 | 175 | 175 | 175 | 175 |
|  |  | Concentration of Phosphorus Atom in Polyamide Resin (ppm by mass) |  | 173.3 | 172.6 | 172.2 | 173.3 | 172.6 | 172.2 |
|  |  | Molar Ratio of Calcium Atom to Phosphorus Atom in Polyamide Resin |  | 0.5 | 0.5 | 0.5 | 0.5 | 0.5 | 0.5 |
|  | Haze After Heat Treatment at 121° C. for 30 minutes (%) |  |  | 3.8 | 3.7 | 3.9 | 58.0 | 57.3 | 54.3 |
|  | Total Light Transmittance After Heat Treatment at 121° C. for 30 minutes (%) |  |  | 88.8 | 88.9 | 88.7 | 77.2 | 78.3 | 75.2 |
|  | YI After Heat Treatment at 121° C. for 30 minutes |  |  | 4.9 | 4.6 | 4.4 | 4.9 | 4.7 | 4.2 |
|  | OTR (ml/0.21 atm · day · package) |  |  | 0.00029 | 0.00028 | 0.0003 | 0.00029 | 0.00026 | 0.0003 |
|  | OTR After Heat Treatment at 121° C. for 30 minutes (ml/0.21 atm · day · package) |  |  | 0.00027 | 0.00026 | 0.00028 | 0.00027 | 0.00026 | 0.00028 |
|  | WVTR (g/day · package) |  |  | 0.0007 | 0.0007 | 0.0007 | 0.0008 | 0.0008 | 0.0008 |
|  | Oil Resistance Test |  |  | X | X | X | ○ | ○ | ○ |

TABLE 1-2

|  |  |  |  | Comparative Example 1-1 | Comparative Example 1-2 | Comparative Example 1-3 | Comparative Example 1-4 |
|---|---|---|---|---|---|---|---|
| Gas Barrier Layer (Y) |  | Inner Layer and Outer Layer (X) |  | COP | COP | COP | PP |
|  | Polyamide Resin (A) | Diamine Unit | Metaxylylenediamine (mol %)*1 | 100 | 100 | N-6I/6T | EVOH |
|  |  | Dicarboxylic Acid Unit | Adipic Acid (mol %)*2 | 94 | 100 |  |  |
|  |  |  | Isophthalic Acid (mol %)*2 | 6 | 0 |  |  |
|  |  | Type of Hypophosphite |  | Ca salt | Ca salt | — | — |
|  |  | Amount of Added Hypophosphite (Phosphorus Atom Concentration Conversion, ppm by mass) |  | 175 | 175 | — | — |
|  |  | Concentration of Phosphorus Atom in Polyamide Resin (ppm by mass) |  | 171.9 | 172.2 | — | — |
|  |  | Molar Ratio of Calcium Atom to Phosphorus Atom in Polyamide Resin |  | 0.5 | 0.5 | — | — |
|  | Haze After Heat Treatment at 121° C. for 30 minutes (%) |  |  | 87.2 | 92.1 | 5.7 | 59.2 |
|  | Total Light Transmittance After Heat Treatment at 121° C. for 30 minutes (%) |  |  | 60.2 | 56.8 | 89.9 | 70.1 |

TABLE 1-2-continued

|  | Comparative Example 1-1 | Comparative Example 1-2 | Comparative Example 1-3 | Comparative Example 1-4 |
|---|---|---|---|---|
| OTR (ml/0.21 atm · day · package) | 0.00032 | 0.00031 | 0.0022 | 0.00021 |
| OTR After Heat Treatment at 121° C. for 30 minutes (ml/0.21 atm · day · package) | 0.00031 | 0.00030 | 0.0023 | 0.0036 |
| WVTR (g/day · package) | 0.0006 | 0.0006 | 0.0006 | 0.0008 |
| Oil Resistance Test | X | X | X | ○ |

Abbreviations used in Table 1-1 and Table 1-2 are as below (the same will apply to all Tables below).
1: content in diamine unit (mol %)
2: content in dicarboxylic acid unit (mol %)
COP: cycloolefin polymer
COC: cycloolefin copolymer
PP: polypropylene-based polymer
N-6I/6T: polyhexamethylene isophthalamide/polyhexamethylene terephthalamide copolymer
EVOH: ethylene-vinyl alcohol copolymer The multilayer vessels of Comparative Examples 1-1 and 1-2 were found to have high haze after heat treatment and low total light transmittance, proving their inferiority in the transparency after heat treatment. In Comparative Example 1-3 using the polyhexamethylene isophthalamide/polyhexamethylene terephthalamide copolymer, poor oxygen barrier performance was shown both before and after the heat treatment. In Comparative Example 1-4 using the ethylene-vinyl alcohol copolymer, only poor oxygen barrier performance after heat treatment was shown.

In contrast, the multilayer vessels of Examples 1-1 to 1-10 were found to show excellent oxygen barrier performance and transparency, as well as water vapor barrier performance, even after heat treatment. In particular, when the polyamide resin contained 20 to 200 ppm by mass of phosphorus atom, and contained calcium atom so that the molar ratio given by (phosphorus atom):(calcium atom) would be 1:0.3 to 0.7, the obtained multilayer vessels were found to have still higher transparency after heat treatment, as well as still smaller YI value after heat treatment. When intended for use as multilayer vessels for medical packaging, high transparency after heat treatment is an important feature, and for this, the multilayer vessel of this invention is very effective.

Although Examples 1-11 to 1-13 were found to show the transparency after heat treatment that was slightly inferior to that in Examples 1-1 to 1-10, but they were transparent enough to keep the content visually observable therethrough, and were found to keep excellent oxygen barrier performance and excellent water vapor barrier performance even after heat treatment. The vessels were also found to be highly oil resistant.

The polyamide resins (A1) to (A7) used in Examples 1-1 to 1-13 were found to show a crystal melting enthalpy ΔHm in the heating process of nearly 0 J/g, indicating that they were amorphous.

The multilayer vessel of this invention has the oxygen barrier performance and the transparency enough to make itself suitable for use as a medical packaging material in need of heat sterilization. It also excels in water vapor barrier performance. Hence, the vessel can store the content over a long period, can keep the content visually observable therethrough even after heat sterilization, and can therefore serve the customer's convenience through provision of a substitute for glass vessels.

Example 2-1

A polyamide resin listed in Table 2-1 was synthesized, according to the method described below.

Into a reaction vessel equipped with a stirrer, a partial condenser, a total condenser, a thermometer, a dropping funnel, a nitrogen gas feeding tube, and a strand die, placed were 6,000 g (41.06 mol) of precisely weighed adipic acid, 6,821 g (41.06 mol) of isophthalic acid, 1.43 g of calcium hypophosphite ($Ca(H_2PO_2)_2$) (25 ppm by mass of phosphorus atom concentration in the polyamide resin), and 7.26 g of sodium acetate, the system was thoroughly replaced with nitrogen gas and then filled with nitrogen gas up to an inner pressure of 0.4 MPa, and the system was heated to 190° C. under stirring while feeding a small flow rate of nitrogen gas. The molar ratio given by sodium acetate/calcium hypophosphite was set to 1.50.

To the content kept under stirring, 11,185 g (82.12 mol) of metaxylylenediamine was added dropwise, and the system was continuously heated while removing the produced water out of the system. After completion of dropwise addition of metaxylylenediamine, the inner temperature was elevated, and upon reaching 265° C., the inside of the reaction vessel was evacuated, the inner temperature was further elevated and kept at 270° C. for 10 minutes, so as to allow the melt polycondensation to proceed. The system was then pressurized with nitrogen gas, the obtained polymer was taken out through the strand die, and pelletized, to obtain approximately 21 kg of polyamide resin (A10) pellets. The polyamide resin (A10) was found to have a glass transition temperature of 128° C., and a relative viscosity of 1.93.

The thus synthesized polyamide resin (A10) was dried in a vacuum drier, under reduced pressure at 115° C. for 24 hours. The dried polyamide resin (A10) was found to have a moisture content of 215 ppm by mass, and a melt viscosity, under a shear rate of 1216 sec' at 270° C., of 236 Pa·sec.

Next, according to the conditions listed below, a material for composing the layer (X) was injected through an injection cylinder, a material for composing the layer (Y) was injected through other injection cylinder concurrently with the resin for composing the layer (X), and further a necessary amount of the material for composing the layer (X) was injected to fill the cavity, to thereby obtain a three-layered multilayer preform (5.1 g) with an X/Y/X structure.

The resin used for composing the layer (X) was a cycloolefin polymer ("ZEONEX (registered trademark) 690R", from ZEON Corporation). The resin used for composing the layer (Y) was the polyamide resin (A10) obtained above.

The thus obtained preform was cooled down to a predetermined temperature, and then subjected to blow molding as a secondary process, wherein the preform was transferred into molds, air was blown therein through the neck to expand the preform so as to match the molds, and then cooled to solidify. A multilayer vessel was thus manufactured.

<<Geometry of Multilayer Vessel>>

Full length=45 mm, outer diameter=24 mmϕ, thickness (total thickness of multilayer vessel, that is, sum of thicknesses of outer layer (X), inner layer (X) and intermediate layer (Y))=1.8 mm, thickness of outer layer (X)=1000 μm, thickness of inner layer (X)=300 μm, thickness of intermediate layer (Y)=500 μm. The multilayer vessel was manufactured by injection blow molding, using an integrated injection/blow molding machine (model "ASB-12N/10T", four-cavity type, from Nissei ASB Machine Co., Ltd.).

(Molding Conditions for Multilayer Vessel)
Injection cylinder temperature for layer (X): 300° C.
Injection cylinder temperature for layer (Y): 260° C.
Temperature of resin flow path in injection molds: 300° C.
Temperature of injection molds: 90° C.
Temperature of blow molding molds: 20° C.

Example 2-2

All conducted in the same way as in Example 2-1, except that the melt polymerization was further allowed to proceed at 270° C. for additional 20 minutes, to obtain polyamide resin (A11) pellets. The polyamide resin (A11) was found to have a relative viscosity of 2.03. The dried polyamide resin (A11) was found to have a moisture content of 261 ppm by mass, and a melt viscosity under a shear rate of 1216 $\sec^{-1}$ at 270° C. of 265 Pa·sec.

A multilayer vessel was manufactured in the same way as in Example 2-1, except that the polyamide resin (A11) was used in place of the polyamide resin (A10).

Example 2-3

All conducted in the same way as in Example 2-1, except that the melt polymerization was further allowed to proceed at 270° C. for additional 40 minutes, to obtain polyamide resin (A12) pellets. The polyamide resin (A12) was found to have a relative viscosity of 2.12. The dried polyamide resin (A12) was found to have a moisture content of 271 ppm by mass, and a melt viscosity under a shear rate of 1216 $\sec^{-1}$ at 270° C. of 334 Pa·sec.

A multilayer vessel was manufactured in the same way as in Example 2-1, except that the polyamide resin (A12) was used in place of the polyamide resin (A10).

Example 2-4

All conducted in the same way as in Example 2-3 except that the drying time was set to 8 hours, to obtain polyamide resin (A13) pellets. The dried polyamide resin (A13) was found to have a moisture content of 795 ppm by mass, and a melt viscosity under a shear rate of 1216 $\sec^{-1}$ at 270° C. of 251 Pa·sec.

A multilayer vessel was manufactured in the same way as in Example 2-1, except that the polyamide resin (A13) was used in place of the polyamide resin (A10).

Example 2-5

All conducted in the same way as in Example 2-1, except that the molar ratio of adipic acid and isophthalic acid was adjusted to 40:60, to obtain polyamide resin (A14) pellets. The polyamide resin (A14) was found to have a glass transition temperature of 140° C., and a relative viscosity of 2.01. The dried polyamide resin (A14) was found to have a moisture content of 291 ppm by mass, and a melt viscosity under a shear rate of 1216 $\sec^{-1}$ at 270° C. of 273 Pa·sec.

A multilayer vessel was manufactured in the same way as in Example 2-1, except that the polyamide resin (A14) was used in place of the polyamide resin (A10).

Example 2-6

All conducted in the same way as in Example 2-1, except that the molar ratio of adipic acid and isophthalic acid was adjusted to 60:40, to obtain polyamide resin (A15) pellets. The polyamide resin (A15) was found to have a glass transition temperature of 119° C., and a relative viscosity of 2.02. The dried polyamide resin (A15) was found to have a moisture content of 287 ppm by mass, and a melt viscosity under a shear rate of 1216 $\sec^{-1}$ at 270° C. of 270 Pa·sec.

A multilayer vessel was manufactured in the same way as in Example 2-1, except that the polyamide resin (A15) was used in place of the polyamide resin (A10).

Example 2-7

A multilayer vessel was manufactured in the same way as in Example 2-1, except that cycloolefin polymer ("ZEONEX (registered trademark) 5000", from Zeon Corporation) was used as the resin for composing the layer (X), in place of the cycloolefin polymer ("ZEONEX (registered trademark) 690R", from Zeon Corporation), the temperature of injection cylinder for layer (X) was changed from 300° C. to 260° C., the temperature of resin flow path in injection dies was changed from 300° C. to 260° C., and the temperature of injection dies was changed from 90° C. to 30° C.

Referential Example 2-1

All conducted in the same way as in Example 2-1, except that the drying time was set to 8 hours, to obtain polyamide resin (A16) pellets. The dried polyamide resin (A16) was found to have a moisture content of 895 ppm by mass, and a melt viscosity under a shear rate of 1216 $\sec^{-1}$ at 270° C. of 167 Pa·sec.

A multilayer vessel was manufactured in the same way as in Example 2-1, except that the polyamide resin (A16) was used in place of the polyamide resin (A10).

Referential Example 2-2

All conducted in the same way as in Example 2-2, except that the drying time was set to 8 hours, to obtain polyamide resin (A17) pellets. The dried polyamide resin (A17) was found to have a moisture content of 1032 ppm by mass, and a melt viscosity under a shear rate of 1216 $\sec^{-1}$ at 270° C. of 127 Pa·sec.

A multilayer vessel was manufactured in the same way as in Example 2-1, except that the polyamide resin (A17) was used in place of the polyamide resin (A10).

Referential Example 2-3

All conducted in the same way as in Example 2-1, except that the molar ratio of adipic acid and isophthalic acid was adjusted to 80:20, to obtain polyamide resin (A18) pellets. The polyamide resin (A18) was found to have a glass transition temperature of 100° C., and a relative viscosity of 2.01. The dried polyamide resin (A18) was found to have a moisture content of 285 ppm by mass, and a melt viscosity under a shear rate of 1216 sec$^{-1}$ at 270° C. of 265 Pa·sec.

A multilayer vessel was manufactured in the same way as in Example 2-1, except that the polyamide resin (A18) was used in place of the polyamide resin (A10).

The multilayer vessels obtained in Examples 2-1 to 2-7 and Referential Examples 2-1 to 2-3 were evaluated regarding the appearance, moldability and oxygen transmission rate (OTR), according to the methods described above. Results are summarized in Table 2-1 or Table 2-2.

TABLE 2-1

| | | | Example 2-1 | Example 2-2 | Example 2-3 | Example 2-4 | Example 2-5 |
|---|---|---|---|---|---|---|---|
| Inner Layer and Outer Layer (X) | | Cycloolefin Polymer | COP | COP | COP | COP | COP |
| | | Glass Transition Temperature (° C.) | 136 | 136 | 136 | 136 | 136 |
| | | Melt Viscosity at 300° C., 1216 Pa · sec−1 (Pa · sec) | 146 | 146 | 146 | 146 | 146 |
| | | Melt Viscosity at 260° C., 1216 Pa · sec−1 (Pa · sec) | 362 | 362 | 362 | 362 | 362 |
| Gas Barrier Layer (Y) | Polyamide Resin (A) | Diamine Unit Metaxylylenediamine (mol %)*1 | 100 | 100 | 100 | 100 | 100 |
| | | Dicarboxylic Acid Unit Adipic Acid (mol %)*2 | 50 | 50 | 50 | 50 | 40 |
| | | Isophthalic Acid (mol %)*2 | 50 | 50 | 50 | 50 | 60 |
| | | Type of Hypophosphite | Ca Salt | Ca Salt | Ca Salt | Ca Salt | Ca Salt |
| | | Amount of Added Hypophosphite (Phosphorus Atom Concentration Conversion, ppm by mass) | 25 | 25 | 25 | 25 | 25 |
| | | Concentration of Phosphorus Atom in Polyamide Resin (ppm by mass) | 24.8 | 24.7 | 24.5 | 24.5 | 24.4 |
| | | Molar Ratio of Calcium Atom to Phosphorus Atom in Polyamide Resin | 0.5 | 0.5 | 0.5 | 0.5 | 0.5 |
| | | Glass Transition Temperature (° C.) | 128 | 128 | 128 | 128 | 140 |
| | | Relative Viscosity | 1.93 | 2.03 | 2.12 | 2.12 | 2.01 |
| | | Moisture ratio (ppm by mass) | 215 | 261 | 271 | 795 | 291 |
| | | Melt Viscosity at 270° C., 1216 Pa · sec−1 (Pa · sec) | 236 | 265 | 334 | 251 | 273 |
| | | Appearance | B | A | A | B | A |
| | | Moldability | A | A | A | A | A |
| | | OTR (ml/0.21 atm · day · package) | 0.00027 | 0.00026 | 0.00027 | 0.00027 | 0.00026 |

TABLE 2-2

| | | | Example 2-6 | Example 2-7 | Referential Example 2-1 | Referential Example 2-2 | Referential Example 2-3 |
|---|---|---|---|---|---|---|---|
| Inner Layer and Outer Layer (X) | | Cycloolefin Polymer | COP | COP | COP | COP | COP |
| | | Glass Transition Temperature (° C.) | 136 | 69 | 136 | 136 | 136 |
| | | Melt Viscosity at 300° C., 1216 Pa · sec−1 (Pa · sec) | 146 | — | 146 | 146 | 146 |
| | | Melt Viscosity at 260° C., 216 Pa · sec−1 (Pa · sec) | 362 | 164 | 362 | 362 | 362 |
| Gas Barrier Layer (Y) | Polyamide Resin (A) | Diamine Unit Metaxylylenediamine (mol %)*1 | 100 | 100 | 100 | 100 | 100 |
| | | Dicarboxylic Acid Unit Adipic Acid (mol %)*2 | 60 | 50 | 50 | 50 | 80 |
| | | Isophthalic Acid (mol %)*2 | 40 | 50 | 50 | 50 | 20 |
| | | Type of Hypophosphite | Ca Salt | Ca Salt | Ca Salt | Ca Salt | Ca Salt |
| | | Amount of Added Hypophosphite (Phosphorus Atom Concentration Conversion, ppm by mass) | 25 | 25 | 25 | 25 | 25 |
| | | Concentration of Phosphorus Atom in Polyamide Resin (ppm by mass) | 24.7 | 24.8 | 24.8 | 24.7 | 24.6 |
| | | Molar Ratio of Calcium Atom to Phosphorus Atom in Polyamide Resin | 0.5 | 0.5 | 0.5 | 0.5 | 0.5 |
| | | Glass Transition Temperature (° C.) | 119 | 128 | 128 | 128 | 100 |
| | | Relative Viscosity | 2.02 | 1.93 | 1.93 | 2.03 | 2.01 |
| | | Moisture ratio (ppm by mass) | 287 | 215 | 895 | 1032 | 285 |
| | | Melt Viscosity at 270° C., 1216 Pa · sec−1 (Pa · sec) | 270 | 236 | 167 | 127 | 265 |
| | | Appearance | A | A | C | C | A |
| | | Moldability | A | A | A | A | C |
| | | OTR (ml/0.21 atm · day · package) | 0.00026 | 0.00026 | 0.00027 | 0.00027 | 0.00026 |

The multilayer vessels of Referential Examples 2-1 and 2-2 were found to have surface undulation although they were practically acceptable. The multilayer vessel of Referential Example 2-3 was found to be poorer in the moldability as compared with Example 2-1, although practically acceptable.

In contrast, the multilayer vessels of Examples 2-1 to 2-7 were found to be remarkably excellent in the appearance and moldability, and also in the oxygen barrier performance. Visual observation also proved excellence of the transparency.

The polyamide resins (A10) to (A18) used in Examples 2-1 to 2-7 were found to show a crystal melting enthalpy ΔHm in the heating process of nearly 0 J/g, indicating that they were amorphous.

Example 3-1

According to the conditions listed below, a material for composing the layer (X) was injected through an injection cylinder, a material for composing the layer (Y) was injected through other injection cylinder concurrently with the resin for composing the layer (X), and further a necessary amount of the material for composing the layer (X) was injected to fill the cavity of injection mold, to thereby manufacture a three-layered multilayer syringe barrel with an layer (X)/layer (Y)/layer (X) structure. The total weight of multilayer syringe barrel was determined to be 1.95 g, with the mass of the layer (Y) determined to be 30% by mass of the total weight of the multilayer syringe barrel. The resin used for composing the layer (X) was a cycloolefin polymer (COP, ZEONEX (registered trademark) 5000, from ZEON Corporation, Tg=69° C.). The resin used for composing the layer (Y) was the polyamide resin (A1) synthesized above in Example 1-1.

<<Geometry of Multilayer Syringe Barrel>>

The capacity was set to 1 cc (1 mL) (standard) in accordance with ISO 11040-6. The multilayer syringe barrel was manufactured using an injection molding machine (Model ASB-12N/10, from Nissei ASB Machine Co., Ltd.). The body (the portion in which chemical liquid will be filled) of the obtained multilayer syringe barrel had thicknesses of the layer (X) (inner layer), the layer (Y) and the layer (X) (outer layer)), in this order, of 300 μm, 250 μm and 950 μm. The total thickness (wall thickness, or, the sum of three layers of layer (X)/layer (Y)/layer (X)) was then given 1500 μm. The multilayer syringe barrel was 64.5 mm long, and the body of multilayer syringe barrel was 9.12 mm in outer diameter.

(Molding Conditions for Syringe)
Injection cylinder temperature for layer (X): 260° C.
Injection cylinder temperature for layer (Y): 250° C.
Temperature of resin flow path in injection mold: 270° C.
Mold temperature: 18° C.

Example 3-2

All conducted in the same way as in Example 3-1 to manufacture a multilayer syringe barrel, except that the polyamide resin (A2) synthesized in Example 1-2 was used in place of the polyamide resin (A1).

Example 3-3

All conducted in the same way as in Example 3-1 to manufacture a multilayer syringe barrel, except that the polyamide resin (A3) synthesized in Example 1-3 was used in place of the polyamide resin (A1).

Example 3-4

All conducted in the same way as in Example 3-1 to manufacture a multilayer syringe barrel, except that the polyamide resin (A4) synthesized in Example 1-4 was used in place of the polyamide resin (A1).

Example 3-5

All conducted in the same way as in Example 3-1 to manufacture a multilayer syringe barrel, except that the polyamide resin (A5) synthesized in Example 1-5 was used in place of the polyamide resin (A1).

Example 3-6

All conducted in the same way as in Example 3-1 to manufacture a multilayer syringe barrel, except that the polyamide resin (A6) synthesized in Example 1-6 was used in place of the polyamide resin (A1).

Comparative Example 3-1

All conducted in the same way as in Example 3-1 to manufacture a multilayer syringe barrel, except that the polyamide resin (A8) synthesized in Comparative Example 1-1 was used in place of the polyamide resin (A1).

Comparative Example 3-2

All conducted in the same way as in Example 3-1 to manufacture a multilayer syringe barrel, except that N-MXD6 ("MX Nylon S6007", from Mitsubishi Gas Chemical Company, Inc., relative viscosity=2.65), composed of a metaxylylenediamine unit and an adipic acid unit, was used in place of the polyamide resin (A1).

Comparative Example 3-3

All conducted in the same way as in Example 3-1 to manufacture a multilayer syringe barrel, except that polyhexamethylene isophthalamide/polyhexamethylene terephthalamide copolymer ("Novamid (registered trademark) X21", from DSM Japan Engineering Plastics, Inc.) was used in place of the polyamide resin (A1).

Comparative Example 3-4

A monolayer syringe barrel composed solely of layer (X) was manufactured, referring to Example 3-1. The thickness of layer (X) was set to 1,500 μm.

The multilayer syringe barrels obtained in Examples 3-1 to 3-6 and Comparative Examples 3-1 to 3-3, and the monolayer syringe obtained in Comparative Example 3-4 were measured regarding the haze and oxygen transmission rate (OTR), before and after storage under filling with water. Examples 3-1 to 3-6 were also measured regarding the YI value before and after storage under filling with water. Also hue of an adrenalin-containing chemical after stored therein was examined. Results are summarized in Table 3-1 or Table 3-2.

TABLE 3-1

| | | | Example 3-1 | Example 3-2 | Example 3-3 | Example 3-4 | Example 3-5 | Example 3-6 |
|---|---|---|---|---|---|---|---|---|
| Inner Layer and Outer Layer (X) | | Type of Cyclopolyolefin Based Polymer | COP | COP | COP | COP | COP | COP |
| | | Tg of Cyclopolyolefin Based Polymer (° C.) | 69 | 69 | 69 | 69 | 69 | 69 |
| Gas Barrier Layer (Y) | Polyamide Resin (A) | Diamine Unit Metaxylylenediamine (mol %)*1 | 100 | 100 | 100 | 100 | 100 | 100 |
| | | Dicarboxylic Acid Unit Adipic Acid (mol %)*2 | 50 | 40 | 60 | 50 | 50 | 50 |
| | | Isophthalic Acid (mol %)*2 | 50 | 60 | 40 | 50 | 50 | 50 |
| | | Type of Hypophosphite | Ca Salt | Ca Salt | Ca Salt | Na Salt | Ca Salt | Ca Salt |
| | | Amount of Added Hypophosphite (Phosphorus Atom Concentration Conversion, ppm by mass) | 175 | 175 | 175 | 175 | 5 | 250 |
| | | Concentration of Phosphorus Atom in Polyamide Resin (ppm by mass) | 173.3 | 172.6 | 172.2 | 170.6 | 4.8 | 247.2 |
| | | Molar Ratio of Calcium Atom to Phosphorus Atom in Polyamide Resin | 0.5 | 0.5 | 0.5 | 0 | 0.5 | 0.5 |
| HAZE (%) | | Initial States | 2.6 | 2.7 | 2.2 | 3.2 | 2.4 | 2.9 |
| | | After Storage with Filled Water | 2.6 | 3.1 | 2.3 | 5.9 | 2.2 | 4.2 |
| OTR (mL/(0.22 atm · day · package)) | | Initial States | 0.00027 | 0.00026 | 0.00028 | 0.00027 | 0.00027 | 0.00027 |
| | | After Storage with Filled Water | 0.00027 | 0.00026 | 0.00028 | 0.00027 | 0.00027 | 0.00027 |
| YI Value | | Initial States | 2.4 | 2.5 | 2.4 | 2.8 | 4.2 | 2.9 |
| | | After Storage with Filled Water | 4.2 | 4.5 | 4.1 | 4.6 | 6.7 | 5.5 |
| Hue of Adrenalin-Containing Chemical Liquid After Storage | | | Clear | Clear | Clear | Clear | Clear | Clear |

TABLE 3-2

| | | | Comparative Example 3-1 | Comparative Example 3-2 | Comparative Example 3-3 | Comparative Example 3-4 |
|---|---|---|---|---|---|---|
| Inner Layer and Outer Layer (X) | | Type of Cyclopolyolefin Based Polymer | COP | COP | COP | COP |
| | | Tg of Cyclopolyolefin Based Polymer (° C.) | 69 | 69 | 69 | |
| Gas Barrier Layer (Y) | Polyamide Resin (A) | Diamine Unit Metaxylylenediamine (mol %)*1 | 100 | 100 | N-6I/6T | |
| | | Dicarboxylic Acid Unit Adipic Acid (mol %)*2 | 94 | 100 | | |
| | | Isophthalic Acid (mol %)*2 | 6 | 0 | | |
| | | Type of Hypophosphite | Ca Salt | Ca Salt | — | |
| | | Amount of Added Hypophosphite (Phosphorus Atom Concentration Conversion, ppm by mass) | 175 | 175 | — | |
| | | Concentration of Phosphorus Atom in Polyamide Resin (ppm by mass) | 171.9 | 172.2 | — | |
| | | Molar Ratio of Calcium Atom to Phosphorus Atom in Polyamide Resin | 0.5 | 0.5 | — | |
| HAZE (%) | | Initial States | 2.7 | 2.9 | 2.7 | 1.5 |
| | | After Storage with Filled Water | 23.4 | 35.2 | 2.9 | 1.6 |
| OTR (mL/(0.22 atm · day · package)) | | Initial States | 0.00032 | 0.00031 | 0.0022 | 0.0032 |
| | | After Storage with Filled Water | 0.00032 | 0.00031 | 0.0022 | 0.0032 |
| Hue of Adrenalin-Containing Chemical Liquid After Storage | | | Clear | Clear | Slightly Yellow | Yellow |

The multilayer syringe barrels of Comparative Examples 3-1 and 3-2 showed extraordinarily high haze after storage with filled water. That is, they were found to be whitened after storage with filled water. The multilayer syringe barrel of Comparative Example 3-3 using the polyhexamethylene isophthalamide/polyhexamethylene terephthalamide copolymer, and the monolayer syringe barrel of Comparative Example 3-4 were found to show poor oxygen barrier performance, both before and after storage with filled water.

In contrast, the multilayer syringe barrels of Examples 3-1 to 3-6 were found to show excellent oxygen barrier performance even after storage with filled water, and suppressed from whitening. In particular, when the polyamide resin contained 20 to 200 ppm by mass of phosphorus atom, and contained calcium atom so that the molar ratio given by (phosphorus atom):(calcium atom) would be 1:0.3 to 0.7, obtainable were the multilayer syringe barrels showing still lower haze and YI values before and after storage with filled water.

Since a chemical liquid to be filled in the prefilled syringe is, in most cases, an aqueous solution, so that if such excellent oxygen barrier performance and suppression of whitening were observed after storage with filled water, the same effects are considered to be obtainable for the chemical liquid.

The syringe barrels obtained in Examples 3-1 to 3-6, when filled with the adrenalin-containing chemical liquid and stored over a long period, were found to suppress change of color of the chemical liquid, allowing easy seeing-through from the outside. The syringe barrels of Comparative Examples 3-1 and 3-2 were found to suppress color change of the chemical liquid, but made such external seeing-through slightly difficult. The syringe barrels of Comparative Example 3-3 and Comparative Example 3-4 were found to be poor in the oxygen barrier performance, showing change of color of the chemical liquid due to oxidation.

The multilayer syringe barrels of Examples have the oxygen barrier performance and the transparency enough to make themselves suitable for use as the multilayer syringe barrel for prefilled syringe that stores the chemical liquid. They also had highly stabilized hue. Hence the multilayer syringe barrels can store the chemical liquid over a long period, and can keep the content visually observable therethrough even after storing therein the chemical liquid, and can serve the customer's convenience through provision of a substitute for glass vessels.

Example 4-1

According to the conditions listed below, a material for composing the layer (X) was injected through an injection cylinder, a material for composing the layer (Y) was injected through other injection cylinder concurrently with the resin for composing the layer (X), and further a necessary amount of the material for composing the layer (X) was injected to fill the cavity of injection mold, to thereby manufacture a three-layered multilayer syringe barrel with an layer (X)/layer (Y)/layer (X) structure. The total weight of multilayer syringe barrel was determined to be 1.95 g, with the mass of the layer (Y) determined to be 30% by mass of the total weight of the multilayer syringe barrel. The resin used for composing the layer (X) was a cycloolefin polymer (COP, ZEONEX (registered trademark) 690R, from ZEON Corporation, Tg=136°). The resin used for composing the layer (Y) was the polyamide resin (A1) synthesized above in Example 1-1.

<<Geometry of Multilayer Syringe Barrel>>

The capacity was set to 1 cc (1 mL) (standard) in accordance with ISO 11040-6. The multilayer syringe barrel was manufactured using an injection molding machine (Model ASB-12N/10, from Nissei ASB Machine Co., Ltd.). The body (the portion in which chemical liquid will be filled) of the obtained multilayer syringe barrel had thicknesses of the layer (X) (inner layer), the layer (Y) and the layer (X) (outer layer), in this order, of 300 µm, 250 µm and 950 µm. The total thickness (wall thickness, or, the sum of three layers of layer (X)/layer (Y)/layer (X)) was then given 1500 µm. The multilayer syringe barrel was 64.5 mm long, and the body of multilayer syringe barrel was 9.2 mm in outer diameter.

(Molding Conditions for Syringe)
Injection cylinder temperature for layer (X): 260° C.
Injection cylinder temperature for layer (Y): 250° C.
Temperature of resin flow path in injection mold: 270° C.
Mold temperature: 18° C.

Example 4-2

A multilayer syringe barrel was manufactured in the same way as in Example 4-1, except that the polyamide resin (A2) synthesized in Example 1-2 was used in place of the polyamide resin (A1).

Example 4-3

A multilayer syringe barrel was manufactured in the same way as in Example 4-1, except that the polyamide resin (A3) synthesized in Example 1-3 was used in place of the polyamide resin (A1).

Example 4-4

A multilayer syringe barrel was manufactured in the same way as in Example 4-1, except that the polyamide resin (A4) synthesized in Example 1-4 was used in place of the polyamide resin (A1).

Example 4-5

A multilayer syringe barrel was manufactured in the same way as in Example 4-1, except that the polyamide resin (A5) synthesized in Example 1-5 was used in place of the polyamide resin (A1).

Example 4-6

A multilayer syringe barrel was manufactured in the same way as in Example 4-1, except that the polyamide resin (A6) synthesized in Example 1-6 was used in place of the polyamide resin (A1).

Examples 4-7 to 4-9

Multilayer syringe barrels were manufactured respectively in the same way as in Examples 4-1 to 4-3, except that a polypropylene-based polymer ("Bormed RB845MO", from BOREALIS AG) was used as the resin for composing the layer (X), in place of the cycloolefin polymer ("ZEONEX (registered trademark) 690R", from ZEON Corporation).

Comparative Example 4-1

A multilayer syringe barrel was manufactured in the same way as in Example 4-1, except that the polyamide resin (A8) synthesized in Comparative Example 1-1 was used in place of the polyamide resin (A1).

Comparative Example 4-2

A multilayer syringe barrel was manufactured in the same way as in Example 4-1, except that N-MXD6 ("MX Nylon S6007", from Mitsubishi Gas Chemical Company, Inc., relative viscosity=2.65), composed of metaxylylenediamine unit and adipic acid unit, was used in place of the polyamide resin (A1).

Comparative Example 4-3

A multilayer syringe barrel was manufactured in the same way as in Example 4-1, except that a polyhexamethylene isophthalamide/polyhexamethylene terephthalamide copolymer ("Novamid (registered trademark) X21", from DSM Japan Engineering Plastics, Inc.) was used in place of the polyamide resin (A1).

Comparative Example 4-4

A multilayer syringe barrel was manufactured in the same way as in Example 4-7, except that an ethylene-vinyl alcohol copolymer ("Eval (registered trademark) F171B", from Kuraray Co., Ltd.) was used in place of the polyamide resin (A1).

Comparative Example 4-5

A monolayer syringe barrel composed solely of the layer (X) was manufactured, according to Example 4-1. The layer (X) was 1500 µm thick.

The multilayer syringe barrels obtained in Examples 4-1 to 4-9 and Comparative Examples 4-1 to 4-5 were measured regarding the haze, the total light transmittance and the OTR, individually for their initial states, states after heat treatment, and states after storage with filled water. The multilayer syringe barrels in Examples 4-1 to 4-9 were also measured regarding the YI value, individually for their initial states, states after heat treatment, and states after storage with filled water. They were also evaluated in the oil resistance test. Results are summarized in Table 4-1 or Table 4-2.

TABLE 4-1

| | | | Example 4-1 | Example 4-2 | Example 4-3 | Example 4-4 | Example 4-5 |
|---|---|---|---|---|---|---|---|
| Inner Layer and Outer Layer (X) | | Type of Polyolefin Resin | COP | COP | COP | COP | COP |
| | | Glass Transision Temperature of Polyolefin Resin (° C.) | 136 | 136 | 136 | 136 | 136 |
| Gas Barrier Layer (Y) | Polyamide Resin (A) | Diamine Unit — Metaxylylenediamine (mol %)*1 | 100 | 100 | 100 | 100 | 100 |
| | | Dicarboxylic Acid Unit — Adipic Acid (mol %)*2 | 50 | 40 | 60 | 50 | 50 |
| | | Isophthalic Acid (mol %)*2 | 50 | 60 | 40 | 50 | 50 |
| | | Type of Hypophosphite | Ca Salt | Ca Salt | Ca Salt | Na Salt | Ca Salt |
| | | Amount of Added Hypophosphite (Phosphorus Atom Concentration Conversion, ppm by mass) | 175 | 175 | 175 | 175 | 5 |
| | | Concentration of Phosphorus Atom in Polyamide Resin (ppm by mass) | 173.3 | 172.6 | 172.2 | 170.6 | 4.8 |
| | | Molar Ratio of Calcium Atom to Phosphorus Atom in Polyamide Resin | 0.5 | 0.5 | 0.5 | 0 | 0.5 |
| Haze (%) | | Initial States | 2.6 | 2.7 | 2.2 | 2.7 | 2.4 |
| | | After Heat Treatment at 121° C. for 30 minutes | 3.2 | 3.1 | 3.6 | 5.8 | 3.3 |
| | | After Storage with Filled Water | 3.3 | 3.2 | 3.5 | 5.9 | 3.3 |
| Total Light Transmittance (%) | | Initial States | 89.6 | 89.5 | 89.7 | 88 | 89.1 |
| | | After Heat Treatment at 121° C. for 30 minutes | 89.1 | 89 | 89.3 | 86.9 | 89.8 |
| | | After Storage with Filled Water | 88.6 | 88.6 | 88.8 | 85.5 | 89 |
| YI Value | | Initial States | 2.4 | 2.5 | 2.4 | 2.3 | 2.3 |
| | | After Heat Treatment at 121° C. for 30 minutes | 4.8 | 4.5 | 4.2 | 4.6 | 7.8 |
| | | After Storage with Filled Water | 4.5 | 4.2 | 4.0 | 4.0 | 7.7 |
| OTR (mL/(0.21 atm · day · package)) | | Initial States | 0.00027 | 0.00026 | 0.00028 | 0.00027 | 0.00027 |
| | | After Heat Treatment at 121° C. for 30 minutes | 0.00027 | 0.00026 | 0.00028 | 0.00027 | 0.00027 |
| | | After Storage with Filled Water | 0.00027 | 0.00026 | 0.00028 | 0.00027 | 0.00027 |
| | | Oil Resistance Test | X | X | X | X | X |

| | | | Example 4-6 | Example 4-7 | Example 4-8 | Example 4-9 |
|---|---|---|---|---|---|---|
| Inner Layer and Outer Layer (X) | | Type of Polyolefin Resin | COP | PP | PP | PP |
| | | Glass Transision Temperature of Polyolefin Resin (° C.) | 136 | — | — | — |
| Gas Barrier Layer (Y) | Polyamide Resin (A) | Diamine Unit — Metaxylylenediamine (mol %)*1 | 100 | 100 | 100 | 100 |
| | | Dicarboxylic Acid Unit — Adipic Acid (mol %)*2 | 50 | 50 | 40 | 60 |
| | | Isophthalic Acid (mol %)*2 | 50 | 50 | 60 | 40 |
| | | Type of Hypophosphite | Ca Salt | Ca Salt | Ca Salt | Ca Salt |
| | | Amount of Added Hypophosphite (Phosphorus Atom Concentration Conversion, ppm by mass) | 250 | 175 | 175 | 175 |
| | | Concentration of Phosphorus Atom in Polyamide Resin (ppm by mass) | 247.2 | 173.3 | 172.6 | 172.2 |
| | | Molar Ratio of Calcium Atom to Phosphorus Atom in Polyamide Resin | 0.5 | 0.5 | 0.5 | 0.5 |
| Haze (%) | | Initial States | 2.1 | 57.1 | 56.2 | 53.0 |
| | | After Heat Treatment at 121° C. for 30 minutes | 3.9 | 58.0 | 57.3 | 54.3 |
| | | After Storage with Filled Water | 4.1 | 58.3 | 57.2 | 54.7 |
| Total Light Transmittance (%) | | Initial States | 89 | 78.4 | 79.3 | 76.8 |
| | | After Heat Treatment at 121° C. for 30 minutes | 88.9 | 77.2 | 78.3 | 75.2 |
| | | After Storage with Filled Water | 88.2 | 76.9 | 77.7 | 75.1 |
| YI Value | | Initial States | 2.5 | 2.1 | 2.2 | 2.3 |
| | | After Heat Treatment at 121° C. for 30 minutes | 5.0 | 4.8 | 4.3 | 4.1 |
| | | After Storage with Filled Water | 4.9 | 4.9 | 4.3 | 4.3 |
| OTR (mL/(0.21 atm · day · package)) | | Initial States | 0.00027 | 0.00029 | 0.00026 | 0.00030 |
| | | After Heat Treatment at 121° C. for 30 minutes | 0.00027 | 0.00027 | 0.00026 | 0.00028 |
| | | After Storage with Filled Water | 0.00027 | 0.00027 | 0.00026 | 0.00028 |
| | | Oil Resistance Test | X | ○ | ○ | ○ |

TABLE 4-2

| | | | | Comparative Example 4-1 | Comparative Example 4-2 | Comparative Example 4-3 | Comparative Example 4-4 | Comparative Example 4-5 |
|---|---|---|---|---|---|---|---|---|
| Inner Layer and Outer Layer (X) | | Type of Polyolefin Resin | | COP | COP | COP | PP | COP |
| | | Glass Transision Temperature of Polyolefin Resin (° C.) | | 136 | 136 | 136 | — | 136 |
| Gas Barrier Layer (Y) | Polyamide Resin (A) | Diamine Unit | Metaxylylenediamine (mol %)*1 | 100 | 100 | N-6I/6T | EVOH | — |
| | | Dicarboxylic Acid Unit | Adipic Acid (mol %)*2 | 94 | 100 | | | |
| | | | Isophthalic Acid (mol %)*2 | 6 | 0 | | | |
| | | Type of Hypophosphite | | Ca Salt | Ca Salt | — | — | |
| | | Amount of Added Hypophosphite (Phosphorus Atom Concentration Conversion, ppm by mass) | | 175 | 175 | — | — | |
| | | Concentration of Phosphorus Atom in Polyamide Resin (ppm by mass) | | 171.9 | 172.2 | — | — | |
| | | Molar Ratio of Calcium Atom to Phosphorus Atom in Polyamide Resin | | 0.5 | 0.5 | — | — | |
| Haze (%) | | | Initial States | 2.7 | 2.9 | 2.7 | 58.7 | 1.5 |
| | | | After Heat Treatment at 121° C. for 30 minutes | 87.2 | 92.1 | 5.7 | 59.2 | 1.6 |
| | | | After Storage with Filled Water | 88.0 | 92.5 | 6.1 | 60.3 | 1.7 |
| Total Light Transmittance (%) | | | Initial States | 66.3 | 58.1 | 89.7 | 76.5 | 89.9 |
| | | | After Heat Treatment at 121° C. for 30 minutes | 60.2 | 56.8 | 89.9 | 70.1 | 89.2 |
| | | | After Storage with Filled Water | 59.1 | 59.9 | 88.8 | 70.0 | 89.2 |
| OTR (mL/(0.21 atm · day · package)) | | | Initial States | 0.00032 | 0.00031 | 0.0022 | 0.00021 | 0.0032 |
| | | | After Heat Treatment at 121° C. for 30 minutes | 0.00031 | 0.00030 | 0.0023 | 0.0036 | 0.0032 |
| | | | After Storage with Filled Water | 0.00031 | 0.00030 | 0.0023 | 0.0036 | 0.0032 |
| | | Oil Resistance Test | | X | X | X | ○ | X |

The multilayer syringe barrels of Comparative Examples 4-1 and 4-2 showed high haze after heated at 121° C. for 30 minutes, and after storage with filled water. They also showed low total light transmittance in their initial states, states after heat treatment at 121° C. for 30 minutes, and states after storage with filled water. They also showed high oxygen transmission rate in their initial states, states after heat treatment at 121° C. for 30 minutes, and states after storage with filled water.

Comparative Example 4-3 using the polyhexamethylene isophthalamide/polyhexamethylene terephthalamide copolymer showed high oxygen transmission rate in its initial state, states after heat treatment at 121° C. for 30 minutes, and states after storage with filled water.

Comparative Example 4-4 using the ethylene-vinyl alcohol copolymer showed high haze after heat treatment at 121° C. for 30 minutes, and after storage with filled water. It also showed low total light transmittance in its initial state, states after heat treatment at 121° C. for 30 minutes, and states after storage with filled water. It also showed high oxygen transmission rate after heat treatment at 121° C. for 30 minutes, and after storage with filled water.

Comparative Example 4-5 using the cycloolefin polymer monolayer showed high oxygen transmission rate in its initial state, states after heat treatment at 121° C. for 30 minutes, and states after storage with filled water.

In contrast, the multilayer syringe barrels of Examples 4-1 to 4-9 showed low haze in their initial states, states after heat treatment at 121° C. for 30 minutes, and states after storage with filled water. They also showed high total light transmittance in their initial states, states after heat treatment at 121° C. for 30 minutes, and states after storage with filled water. They also showed low oxygen transmission rate in their initial states, states after heat treatment at 121° C. for 30 minutes, and states after storage with filled water.

Examples 4-7 to 4-9 showed, as compared with Examples 4-1 to 4-6, slightly higher haze, slightly lower total light transmittance, and thus slightly poorer transparency, in their initial states, states after heat treatment at 121° C. for 30 minutes, and states after storage with filled water, but the levels were enough for keeping the content visually observable therethrough. The multilayer syringe barrels were also found to excel in oil resistance.

When the polyamide resin (A) contained 20 to 200 ppm by mass of phosphorus atom, and contained calcium atom so that the molar ratio given by (phosphorus atom):(calcium atom) would be 1:0.3 to 0.7, obtainable were the multilayer syringe barrels especially good in all aspects, showing still lower haze after heat treatment at 121° C. for 30 minutes and after storage with filled water, and showing still smaller YI value after heat treatment at 121° C. for 30 minutes and after storage with filled water.

The multilayer syringe barrel of Examples has the oxygen barrier performance and the transparency enough to make themselves suitable for use as the multilayer syringe barrel for prefilled syringe that stores the chemical liquid after heat sterilization. They also had highly stabilized hue. Hence the multilayer syringe barrel can store the chemical liquid over a long period, and can keep the content visually observable therethrough even after storing therein the chemical liquid, and can serve the customer's convenience through provision of a substitute for glass vessels.

Example 5-1

Using a multilayer direct blow molding machine equipped with first to third extruders, cylindrical dies and mold, polypropylene-based polymer ("Novatec PP FY6", from Japan Polypropylene Corporation, also referred to as "PP", hereinafter) was extruded through the first extruder at 260° C., the polyamide resin (A1) synthesized in Example 1-1 was extruded through the second extruder at 260° C., and an adhesive polypropylene ("Modic P604V", from Mitsubishi Chemical Corporation, also referred to as "adhesive PP", hereinafter) was extruded through the third extruder at 230° C., and blow-molded in the mold, to manufacture a 100 mL

Example 5-2

A multilayer vessel was manufactured in the same way as in Example 5-1, except that the polyamide resin (A2) synthesized in Example 1-2 was used in place of the polyamide resin (A1).

Example 5-3

A multilayer vessel was manufactured in the same way as in Example 5-1, except that the polyamide resin (A3) synthesized in Example 1-3 was used in place of the polyamide resin (A1).

Example 5-4

A multilayer vessel was manufactured in the same way as in Example 5-1, except that the polyamide resin (A4) synthesized in Example 1-4 was used in place of the polyamide resin (A1).

Example 5-5

A multilayer vessel was manufactured in the same way as in Example 5-1, except that the polyamide resin (A5) synthesized in Example 1-5 was used in place of the polyamide resin (A1).

Example 5-6

A multilayer vessel was manufactured in the same way as in Example 5-1, except that the polyamide resin (A6) synthesized in Example 1-6 was used in place of the polyamide resin (A1).

multilayer vessel (multilayer bottle) with a triple five-layered structure. The structure of multilayer vessel, viewed from the inner layer, is given as PP layer (400 μm)/adhesive PP layer (15 μm)/polyamide resin (A1) layer (100 μm)/adhesive PP layer (15 μm)/PP layer (400 μm).

Example 5-7

A multilayer vessel was manufactured in the same way as in Example 5-1, except that the polyamide resin (A7) synthesized in Example 1-7 was used in place of the polyamide resin (A1).

Comparative Example 5-1

A multilayer vessel was manufactured in the same way as in Example 5-1, except that the polyamide resin (A8) synthesized in Comparative Example 1-1 was used in place of the polyamide resin (A1).

Comparative Example 5-2

A multilayer vessel was manufactured in the same way as in Example 5-1, except that N-MXD6 ("MX Nylon S6007", from Mitsubishi Gas Chemical Company, Inc., relative viscosity=2.65), composed of metaxylylenediamine unit and adipic acid unit, was used in place of the polyamide resin (A1).

Comparative Example 5-3

A multilayer vessel was manufactured in the same way as in Example 5-1, except that a polyhexamethylene isophthalamide/polyhexamethylene terephthalamide copolymer ("Novamid (registered trademark) X21", from DSM Japan Engineering Plastics, KK) was used in place of the polyamide resin (A1).

The multilayer vessels obtained in Examples 5-1 to 5-7 and Comparative Examples 5-1 to 5-3 were measured regarding the oxygen transmission rate (OTR) and the water vapor transmission rate (WVTR), according to the methods described above. They were also evaluated regarding self-supportability. The obtained multilayer vessels were further heat treated under the conditions described above, and then measured regarding the oxygen transmission rate (OTR) after heat treatment. Examples 5-1 to 5-7 were further measured regarding the haze and the YI value, both after heat treatment. Results are summarized in Table 5-1 or Table 5-2.

TABLE 5-1

| | | | | Example 5-1 | Example 5-2 | Example 5-3 | Example 5-4 |
|---|---|---|---|---|---|---|---|
| | | Inner Layer and Outer Layer (X) | | PP | PP | PP | PP |
| Gas Barrier Layer (Y) | Polyamide Resin (A) | Diamine Unit | Metaxylylenediamine (mol %)*1 | 100 | 100 | 100 | 100 |
| | | Dicarboxylic Acid Unit | Adipic Acid (mol %)*2 | 50 | 40 | 60 | 50 |
| | | | Isophthalic Acid (mol %)*2 | 50 | 60 | 40 | 50 |
| | | Type of Hypophosphite | | Ca Salt | Ca Salt | Ca Salt | Na Salt |
| | | Amount of Added Hypophosphite (Phosphorus Atom Concentration Conversion, ppm by mass) | | 175 | 175 | 175 | 175 |
| | | Concentration of Phosphorus Atom in Polyamide Resin (ppm by mass) | | 173.3 | 172.6 | 172.2 | 170.6 |
| | | Molar Ratio of Calcium Atom to Phosphorus Atom in Polyamide Resin | | 0.5 | 0.5 | 0.5 | 0 |
| | | Haze After Heat Treatment at 121° C. for 30 minutes (%) | | 59.0 | 56.3 | 58.2 | 65.8 |
| | | YI After Heat Treatment at 121° C. for 30 minutes | | 5.00 | 4.8 | 4.5 | 4.8 |
| | | OTR (ml/0.21 atm · day · package) | | 0.00030 | 0.00028 | 0.00029 | 0.00027 |
| | | OTR After Heat Treatment at 121° C. for 30 minutes (ml/0.21 atm · day · package) | | 0.00027 | 0.00026 | 0.00028 | 0.00027 |
| | | WVTR (g/day · package) | | 0.0008 | 0.0008 | 0.0008 | 0.0008 |
| | | Self-Supportability | | A | A | A | A |

TABLE 5-1-continued

|  |  |  |  | Example 5-5 | Example 5-6 | Example 5-7 |
|---|---|---|---|---|---|---|
|  |  | Inner Layer and Outer Layer (X) |  | PP | PP | PP |
| Gas Barrier | Polyamide | Diamine Unit | Metaxylylenediamine (mol %)*1 | 100 | 100 | 100 |
| Layer | Resin | Dicarboxylic | Adipic Acid (mol %)*2 | 50 | 50 | 50 |
| (Y) | (A) | Acid Unit | Isophthalic Acid (mol %)*2 | 50 | 50 | 50 |
|  |  | Type of Hypophosphite |  | Ca Salt | Ca Salt | Ca Salt |
|  |  | Amount of Added Hypophosphite (Phosphorus Atom Concentration Conversion, ppm by mass) |  | 5 | 250 | 25 |
|  |  | Concentration of Phosphorus Atom in Polyamide Resin (ppm by mass) |  | 4.8 | 247.2 | 24.8 |
|  |  | Molar Ratio of Calcium Atom to Phosphorus Atom in Polyamide Resin |  | 0.5 | 0.5 | 0.5 |
|  |  | Haze After Heat Treatment at 121° C. for 30 minutes (%) |  | 57.1 | 57.9 | 56.6 |
|  |  | YI After Heat Treatment at 121° C. for 30 minutes |  | 7.2 | 5.3 | 5.1 |
|  |  | OTR (ml/0.21 atm · day · package) |  | 0.00028 | 0.00028 | 0.00029 |
|  |  | OTR After Heat Treatment at 121° C. for 30 minutes (ml/0.21 atm · day · package) |  | 0.00029 | 0.00027 | 0.00027 |
|  |  | WVTR (g/day · package) |  | 0.0008 | 0.0008 | 0.0008 |
|  |  | Self-Supportability |  | A | A | A |

TABLE 5-2

|  |  |  |  | Comparative Example 5-1 | Comparative Example 5-2 | Comparative Example 5-3 |
|---|---|---|---|---|---|---|
|  |  | Inner Layer and Outer Layer (X) |  | PP | PP | PP |
| Gas Barrier | Polyamide | Diamine Unit | Metaxylylenediamine (mol %)*1 | 100 | 100 | N-6I/6T |
| Layer | Resin | Dicarboxylic Acid Unit | Adipic Acid (mol %)*2 | 94 | 100 |  |
| (Y) | (A) |  | Isophthalic Acid (mol %)*2 | 6 | 0 |  |
|  |  | Type of Hypophosphite |  | Ca Salt | Ca Salt | — |
|  |  | Amount of Added Hypophosphite (Phosphorus Atom Concentration Conversion, ppm by mass) |  | 175 | 175 | — |
|  |  | Concentration of Phosphorus Atom in Polyamide Resin (ppm by mass) |  | 171.9 | 172.2 | — |
|  |  | Molar Ratio of Calcium Atom to Phosphorus Atom in Polyamide Resin |  | 0.5 | 0.5 | — |
|  |  | Haze After Heat Treatment at 121° C. for 30 minutes (%) |  | 90.4 | 94.1 | 57.5 |
|  |  | OTR (ml/0.21 atm · day · package) |  | 0.00035 | 0.00034 | 0.0041 |
|  |  | OTR After Heat Treatment at 121° C. for 30 minutes (ml/0.21 atm · day · package) |  | 0.00034 | 0.0004 | 0.0045 |
|  |  | WVTR (g/day · package) |  | 0.0008 | 0.0008 | 0.0008 |
|  |  | Self-Supportability |  | A | A | A |

The multilayer vessels of Comparative Examples 5-1 and 5-2 showed high haze after heat treatment, and low transparency after heat treatment. Comparative Example 5-3 using the polyhexamethylene isophthalamide/polyhexamethylene terephthalamide copolymer showed poor oxygen barrier performances, both before and after the heat treatment.

In contrast, the multilayer vessels of Examples 5-1 to 5-7 were found to excel in the oxygen barrier performance, to keep a necessary level of translucency, and to excel in the water vapor barrier performance, even after the heat treatment. In particular, when the polyamide resin contained 20 to 200 ppm by mass of phosphorus atom, and contained calcium atom so that the molar ratio given by (phosphorus atom):(calcium atom) would be 1:0.3 to 0.7, the obtained multilayer vessels were found to have still higher transparency after heat treatment. When intended for use as multilayer vessels for medical packaging, high transparency after heat treatment is an important feature, and for this, the multilayer vessel of this invention is very effective.

The multilayer vessel of this invention has the oxygen barrier performance and content recognizability enough to make itself suitable for use as a medical packaging material in need of heat sterilization. It also excels in water vapor barrier performance. Hence, the vessel can store the content over a long period, can keep the content visually observable therethrough even after heat sterilization, and can therefore serve the customer's convenience through provision of a substitute for glass vessels.

Example 6-1

According to the conditions listed below, a material for composing the layer (X) was injected through an injection cylinder, a material for composing the layer (Y) was injected through other injection cylinder concurrently with the resin for composing the layer (X), and further a necessary amount of the material for composing the layer (X) was injected to fill the cavity, to thereby obtain a three-layered multilayer preform (5.1 g) with an X/Y/X structure.

The resin used for composing the layer (X) was a cycloolefin polymer ("ZEONEX (registered trademark) 690R", from ZEON Corporation). The resin used for composing the layer (Y) was the polyamide resin (A1) synthesized above in Example 1-1.

The thus obtained preform was cooled down to a predetermined temperature, and then subjected to blow molding as a secondary process, wherein the preform was transferred into mold, air was blown therein through the neck to expand the preform so as to match the mold, and then cooled to solidify. A bio-pharmaceutical vessel was thus manufactured.

<<Geometry of Bio-pharmaceutical Vessel>>

Full length=45 mm, outer diameter=24 mm, thickness (total thickness of bio-pharmaceutical vessel, that is, sum of thicknesses of outer layer (X), inner layer (X) and intermediate layer (Y))=1.0 mm, thickness of outer layer (X)=600 μm, thickness of inner layer (X)=200 μm, thickness of intermediate layer (Y)=200 μm. The bio-pharmaceutical vessel was manufactured by injection blow molding, using an integrated injection/blow molding machine (model "ASB-12N/10T", four-cavity type, from Nissei ASB Machine Co., Ltd.).

(Molding Conditions for Bio-Pharmaceutical Vessel)
Injection cylinder temperature for layer (X): 300° C.
Injection cylinder temperature for layer (Y): 280° C.
Temperature of resin flow path in injection mold: 300° C.
Blow temperature: 150° C.
Temperature of cooling water for blow mold: 40° C.

Example 6-2

A bio-pharmaceutical vessel was manufactured in the same way as in Example 6-1, except that the polyamide resin (A2) synthesized in Example 1-2 was used in place of the polyamide resin (A1).

Example 6-3

A bio-pharmaceutical vessel was manufactured in the same way as in Example 6-1, except that the polyamide resin (A3) synthesized in Example 1-3 was used in place of the polyamide resin (A1).

Example 6-4

A bio-pharmaceutical vessel was manufactured in the same way as in Example 6-1, except that the polyamide resin (A4) synthesized in Example 1-4 was used in place of the polyamide resin (A1).

Example 6-5

A bio-pharmaceutical vessel was manufactured in the same way as in Example 6-1, except that the polyamide resin (A5) synthesized in Example 1-5 was used in place of the polyamide resin (A1).

Example 6-6

A bio-pharmaceutical vessel was manufactured in the same way as in Example 6-1, except that the polyamide resin (A6) synthesized in Example 1-6 was used in place of the polyamide resin (A1).

Examples 6-7 to 6-9

Bio-pharmaceutical vessels were manufactured respectively in the same way as in Examples 6-1 to 6-3, except that a cycloolefin copolymer ("TOPAS (registered trademark) 6013S-04", from TOPAS Advanced Polymers GmbH) was used as the resin for composing the layer (X), in place of the cycloolefin polymer ("ZEONEX (registered trademark) 690R", from ZEON Corporation).

Example 6-10 to 6-12

Bio-pharmaceutical vessels were manufactured respectively in the same way as in Examples 6-1 to 6-3, except that a polypropylene-based polymer ("Bormed RB845MO", from BOREALIS AG) was used as the resin for composing the layer (X), in place of the cycloolefin polymer ("ZEONEX (registered trademark) 690R", from ZEON Corporation).

Comparative Example 6-1

A bio-pharmaceutical vessel was manufactured in the same way as in Example 6-1, except that the polyamide resin (A8) synthesized in Comparative Example 1-1 was used in place of the polyamide resin (A1).

Comparative Example 6-2

A multilayer vessel was manufactured in the same way as in Example 6-1, except that N-MXD6 ("MX Nylon S6007", from Mitsubishi Gas Chemical Company, Inc., relative viscosity=2.65), composed of metaxylylenediamine unit and adipic acid unit, was used in place of the polyamide resin (A1).

Comparative Example 6-3

A bio-pharmaceutical vessel was manufactured in the same way as in Example 6-1, except that a polyhexamethylene isophthalamide/polyhexamethylene terephthalamide copolymer ("Novamid (registered trademark) X21", from DSM Japan Engineering Plastics, KK) was used in place of the polyamide resin (A1).

Comparative Example 6-4

A bio-pharmaceutical vessel was manufactured in the same way as in Example 6-11, except that an ethylene-vinyl alcohol copolymer ("Eval (registered trademark) F171B", from Kuraray Co., Ltd.) was used in place of the polyamide resin (A1).

Comparative Example 6-5

A monolayer bio-pharmaceutical vessel composed solely of the layer (X) was manufactured, according to Example 6-1. The layer (X) was 1000 μm thick.

The bio-pharmaceutical vessels obtained in Examples 6-1 to 6-12 and Comparative Examples 6-1 to 6-5 were measured regarding the oxygen transmission rate (OTR), according to the method described above. Also the haze, the total light transmittance and the oxygen transmission rate (OTR), after heat treatment, were measured. The obtained bio-pharmaceutical vessels also subjected to oil resistance test. Retention rate of antibody activity was also measured. The bio-pharmaceutical vessels obtained in Examples 6-1 to 6-12 were also measured regarding the YI value after heat treatment.

Results are summarized in Table 6-1 to Table 6-3.

TABLE 6-1

|  |  |  |  | Example 6-1 | Example 6-2 | Example 6-3 | Example 6-4 | Example 6-5 | Example 6-6 |
|---|---|---|---|---|---|---|---|---|---|
| | | Inner Layer and Outer Layer (X) | | COP | COP | COP | COP | COP | COP |
| Gas Barrier Layer (Y) | Polyamide Resin (A) | Diamine Unit | Metaxylylenediamine*1 (mol %) | 100 | 100 | 100 | 100 | 100 | 100 |
| | | Dicarboxylic Acid Unit | Adipic Acid (mol %)*2 | 50 | 40 | 60 | 50 | 50 | 50 |
| | | | Isophthalic Acid (mol %)*2 | 50 | 60 | 40 | 50 | 50 | 50 |
| | | Type of Hypophosphite | | Ca salt | Ca salt | Ca salt | Na salt | Ca salt | Ca salt |
| | | Amount of Added Hypophosphite (Phosphorus Atom Concentration Conversion, ppm by mass) | | 175 | 175 | 175 | 175 | 5 | 250 |
| | | Concentration of Phosphorus Atom in Polyamide Resin (ppm by mass) | | 173.3 | 172.6 | 172.2 | 170.6 | 4.8 | 247.2 |
| | | Molar Ratio of Calcium Atom to Phosphorus Atom in Polyamide Resin | | 0.5 | 0.5 | 0.5 | 0 | 0.5 | 0.5 |
| Haze After Heat Treatment at 121° C. for 30 minutes (%) | | | | 3.2 | 3.1 | 3.6 | 5.8 | 3.3 | 3.9 |
| Total Transmittance After Heat Treatment at 121° C. for 30 minutes (%) | | | | 89.1 | 89.0 | 89.3 | 86.9 | 89.8 | 88.9 |
| YI After Heat Treatment at 121° C. for 30 minutes (%) | | | | 4.8 | 4.5 | 4.2 | 4.6 | 7.8 | 5.0 |
| OTR (mL/0.21 (atm · day · package)) | | | | 0.00027 | 0.00026 | 0.00028 | 0.00027 | 0.00027 | 0.00027 |
| OTR After Heat Treatment at 121° C. for 30 minutes (ml/0.21 atm · day · package) | | | | 0.00027 | 0.00026 | 0.00028 | 0.00027 | 0.00027 | 0.00027 |
| Oil Resistance Test | | | | X | X | X | X | X | X |
| Retention Rate of Antibody Activity (%) | | | | 75 | 78 | 73 | 74 | 75 | 76 |

TABLE 6-2

|  |  |  |  | Example 6-7 | Example 6-8 | Example 6-9 | Example 6-10 | Example 6-11 | Example 6-12 |
|---|---|---|---|---|---|---|---|---|---|
| | | Inner Layer and Outer Layer (X) | | COC | COC | COC | PP | PP | PP |
| Gas Barrier Layer (Y) | Polyamide Resin (A) | Diamine Unit | Metaxylylenediamine (mol %)*1 | 100 | 100 | 100 | 100 | 100 | 100 |
| | | Dicarboxylic Acid Unit | Adipic Acid (mol %)*2 | 50 | 40 | 60 | 50 | 40 | 60 |
| | | | Isophthalic Acid (mol %)*2 | 50 | 60 | 40 | 50 | 60 | 40 |
| | | Type of Hypophosphite | | Ca salt | Ca salt | Ca salt | Ca salt | Ca salt | Ca salt |
| | | Amount of Added Hypophosphite (Phosphorus Atom Concentration Conversion, ppm by mass) | | 175 | 175 | 175 | 175 | 175 | 175 |
| | | Concentration of Phosphorus Atom in Polyamide Resin (ppm by mass) | | 173.3 | 172.6 | 172.2 | 173.3 | 172.6 | 172.2 |
| | | Molar Ratio of Calcium Atom to Phosphorus Atom in Polyamide Resin | | 0.5 | 0.5 | 0.5 | 0.5 | 0.5 | 0.5 |
| Haze After Heat Treatment at 121° C. for 30 minutes (%) | | | | 3.8 | 3.7 | 3.9 | 58 | 57.3 | 54.3 |
| Total Transmittance After Heat Treatment at 121° C. for 30 minutes (%) | | | | 88.8 | 88.9 | 88.7 | 77.2 | 78.3 | 75.2 |
| YI After Heat Treatment at 121° C. for 30 minutes (%) | | | | 4.9 | 4.6 | 4.4 | 4.9 | 4.7 | 4.2 |
| OTR (mL/0.21 (atm · day · package)) | | | | 0.00029 | 0.00028 | 0.0003 | 0.00029 | 0.00026 | 0.0003 |
| OTR After Heat Treatment at 121° C. for 30 minutes (ml/0.21 atm · day · package) | | | | 0.00027 | 0.00026 | 0.00028 | 0.00027 | 0.00026 | 0.00028 |
| Oil Resistance Test | | | | X | X | X | ○ | ○ | ○ |
| Retention Rate of Antibody Activity (%) | | | | 74 | 77 | 73 | 75 | 78 | 75 |

TABLE 6-3

|  |  |  |  | Comparative Example 6-1 | Comparative Example 6-2 | Comparative Example 6-3 | Comparative Example 6-4 | Comparative Example 6-5 |
|---|---|---|---|---|---|---|---|---|
| | | Inner Layer and Outer Layer (X) | | COP | COP | COP | PP | COP |
| Gas Barrier Layer (Y) | Polyamide Resin (A) | Diamine Unit | Metaxylylenediamine (mol %)*1 | 100 | 100 | N-6I/6T | EVOH | — |
| | | Dicarboxylic Acid Unit | Adipic Acid (mol %)*2 | 94 | 100 | | | — |
| | | | Isophthalic Acid (mol %)*2 | 6 | 0 | | | |
| | | Type of Hypophosphite | | Ca Salt | Ca Salt | — | — | — |
| | | Amount of Added Hypophosphite (Phosphorus Atom Concentration Conversion, ppm by mass) | | 175 | 175 | — | — | — |
| | | Concentration of Phosphorus Atom in Polyamide Resin (ppm by mass) | | 171.9 | 172.2 | — | — | — |

TABLE 6-3-continued

|  | Comparative Example 6-1 | Comparative Example 6-2 | Comparative Example 6-3 | Comparative Example 6-4 | Comparative Example 6-5 |
|---|---|---|---|---|---|
| Molar Ratio of Calcium Atom to Phosphorus Atom in Polyamide Resin | 0.5 | 0.5 | — | — | — |
| Haze After Heat Treatment at 121° C. for 30 minutes (%) | 87.2 | 92.1 | 5.7 | 59.2 | 1.2 |
| Total Transmittance After Heat Treatment at 121° C. for 30 minutes (%) | 60.2 | 56.8 | 89.9 | 70.1 | 91.6 |
| OTR (mL/0.21 (atm · day · package)) | 0.00032 | 0.00031 | 0.0022 | 0.00021 | 0.028 |
| OTR After Heat Treatment at 121° C. for 30 minutes (ml/0.21 atm · day · package) | 0.00031 | 0.0003 | 0.0023 | 0.0036 | 0.028 |
| Oil Resistance Test | X | X | X | ◯ | X |
| Retention Rate of Antibody Activity (%) | 72 | 70 | 51 | 44 | 20 |

The bio-pharmaceutical vessels of Comparative Example 6-1 and 6-2 showed high haze and low total light transmittance after heat treatment, proving their inferiority in the transparency after heat treatment.

In Comparative Example 6-3 using the polyhexamethylene isophthalamide/polyhexamethylene terephthalamide copolymer, a bio-pharmaceutical contained therein was found to show degraded medical efficacy after storage, and poor oxygen barrier performance was shown both before and after the heat treatment.

In Comparative Example 6-4 using the ethylene-vinyl alcohol copolymer, a bio-pharmaceutical contained therein was found to show degraded medical efficacy after storage, and poor oxygen barrier performance was shown after the heat treatment.

In Comparative Example 6-5 solely using the cycloolefin polymer, a bio-pharmaceutical contained therein was found to show degraded medical efficacy, and poor oxygen barrier performance was shown both before and after the heat treatment.

In contrast, the medicine contained in the bio-pharmaceutical vessels of Examples 6-1 to 6-12 was found to suppress its medical efficacy from degrading.

The bio-pharmaceutical vessels of Examples 6-1 to 6-12 were also found to excel in transparency even after heat treatment. Examples were also found to excel in the oxygen barrier performance.

In particular, when the polyamide resin contained 20 to 200 ppm by mass of phosphorus atom, and contained calcium atom so that the molar ratio given by (phosphorus atom):(calcium atom) would be 1:0.3 to 0.7, the obtained bio-pharmaceutical vessels were found to have still higher translucency after heat treatment, and a still lower YI value after heat treatment.

Examples 6-10 to 6-12 showed, as compared with other Examples, slightly poorer transparency after heat treatment, but the levels were enough for keeping the content visually observable therethrough, and were found to excel in the oxygen barrier performance even after heat treatment. They were also found to be highly oil-resistant vessels.

The bio-pharmaceutical vessel of this invention has the transparency enough to make itself suitable for use as a bio-pharmaceutical vessel for storing a protein-derived medicinal component. It can also suppress a bio-pharmaceutical contained therein from degrading its medical efficacy after storage. It also excels in oxygen barrier performance. Hence, the vessel can store the bio-pharmaceutical over a long period, can keep the content visually observable therethrough even after heat sterilization, and can therefore serve the customer's convenience through provision of a substitute for glass vessels.

In this specification, the description content of the specification of Japanese patent application No. 2016-236445, Japanese patent application No. 2017-021354, Japanese patent application No. 2017-021352, Japanese patent application No. 2017-021353, Japanese patent application No. 2017-021355, Japanese patent application No. 2017-021351, and Japanese patent application No. 2017-022395 are incorporated.

DESCRIPTION OF REFERENCE NUMERALS 1 multilayer syringe barrel of a prefilled syringe
2 hub of the multilayer syringe barrel
3 flange of the multilayer syringe barrel
4 cap for the hub
5 gasket
6 rod of a plunger
7 chemical liquid
11 vial
12 packing
13 cap
14 medicine

The invention claimed is:
1. A multilayer vessel comprising:
a layer (X) that contains at least one type of polyolefin resin as a major ingredient; and
a layer (Y) that contains a polyamide resin (A) as a major ingredient,
the polyamide resin (A) being composed of a structural unit derived from diamine, and a structural unit derived from dicarboxylic acid,
70 mol % or more of the structural unit derived from diamine being derived from metaxylylenediamine, and
30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid,
wherein the layer (X) contains a cycloolefin-based polymer (B) as the major ingredient,
the cycloolefin-based polymer (B) has a glass transition temperature of 50 to 170° C.,
the polyamide resin (A) has a glass transition temperature of 100 to 160° C.,
the cycloolefin-based polymer (B) shows a melt viscosity of 100 to 250 Pa sec at one or more temperatures between 260 and 300° C., under a shear rate of 1216 sec$^{-1}$, and
the polyamide resin (A) shows a melt viscosity of 200 to 400 Pa sec at 270° C., under a shear rate 1216 sec$^{-1}$.
2. The multilayer vessel of claim 1, wherein the polyolefin resin further comprises a polypropylene-based polymer.

3. The multilayer vessel of claim 1, which has a difference between the glass transition temperatures of the cycloolefin-based polymer (B) and the polyamide resin (A) of 70° C. or smaller.

4. The multilayer vessel of claim 1, wherein
the a cycloolefin-based polymer (B) has a glass transition temperature of lower than 100° C., and,
the multilayer vessel is a multilayer syringe barrel for prefilled syringe.

5. The multilayer vessel of claim 4, wherein
the cycloolefin-based polymer (B) has a glass transition temperature of 50 to 90° C.

6. A syringe comprising the multilayer syringe barrel for prefilled syringe described in claim 4.

7. A prefilled syringe comprising the syringe described in claim 6, and a chemical liquid filled in the syringe.

8. The multilayer vessel of claim 1, wherein the cycloolefin-based polymer (B) has a glass transition temperature of 100° C. or higher, and,
the multilayer vessel is a multilayer syringe barrel for prefilled syringe.

9. The multilayer vessel of claim 1, comprising at least three layers, whose inner layer and outer layer being the layer (X), and at least one of intermediate layer(s) being the layer (Y).

10. The multilayer vessel of claim 1, wherein the layer (Y) has a thickness that accounts for 2 to 40% of the total thickness of the multilayer vessel.

11. The multilayer vessel of claim 1, comprising the layer (X) that contains the cycloolefin-based polymer (B) as the major ingredient, an adhesive layer, and the layer (Y) that contains the polyamide resin (A) as the major ingredient, arranged in this order.

12. The multilayer vessel of claim 11, wherein the layer (X) further contains at least one type of polypropylene-based polymer.

13. The multilayer vessel of claim 11, comprising at least five layers, whose inner layer and outer layer being the layer (X), and at least one of intermediate layers being the layer (Y).

14. The multilayer vessel of claim 1, wherein the polyamide resin (A) contains calcium atom.

15. The multilayer vessel of claim 14, wherein the calcium atom contained in the polyamide resin (A) is derived from calcium hypophosphite.

16. The multilayer vessel of claim 1, wherein the polyamide resin (A) contains 3 to 300 ppm by mass of phosphorus atom.

17. The multilayer vessel of claim 1, wherein the polyamide resin (A) contains 20 to 200 ppm by mass of phosphorus atom, and contains calcium atom so that the molar ratio given by (phosphorus atom):(calcium atom) will be 1:0.3 to 0.7.

18. The multilayer vessel of claim 1, wherein 30 to 60 mol % of the structural unit derived from dicarboxylic acid is an adipic acid-derived structural unit.

19. The multilayer vessel of claim 1, which is suitable for medical packaging.

20. A multilayer article comprising:
a layer (X) that contains at least one type of polyolefin resin as a major ingredient, and
a layer (Y) that contains a polyamide resin (A) as a major ingredient,
the polyamide resin (A) being composed of a structural unit derived from diamine, and a structural unit derived from dicarboxylic acid,
70 mol % or more of the structural unit derived from diamine being derived from metaxylylenediamine, and
30 to 60 mol % of the structural unit derived from dicarboxylic acid being derived from straight chain aliphatic α,ω-dicarboxylic acid having 4 to 20 carbon atoms, and 70 to 40 mol % being derived from isophthalic acid,
wherein the layer (X) contains at least one of cycloolefin-based polymer (B) as the major ingredient,
the cycloolefin-based polymer (B) has a glass transition temperature of 50 to 170° C.,
the polyamide resin (A) has a glass transition temperature of 100 to 160° C.,
the cycloolefin-based polymer (B) shows a melt viscosity of 100 to 250 Pa sec at one or more temperatures between 260 and 300° C., under a shear rate of 1216 $sec^{-1}$, and
the polyamide resin (A) shows a melt viscosity of 200 to 400 Pa sec at 270° C., under a shear rate 1216 $sec^{-1}$.

21. The multilayer article of claim 20,
wherein the polyamide resin (A) contains 20 to 200 ppm by mass of phosphorus atom, and contains calcium atom so that the molar ratio given by (phosphorus atom):(calcium atom) will be 1:0.3 to 0.7.

22. The multilayer article of claim 20, comprising the layer (X) that contains the cycloolefin-based polymer (B) as the major ingredient, an adhesive layer, and the layer (Y) that contains the polyamide resin (A) as the major ingredient, arranged in this order.

23. A method for manufacturing a multilayer vessel according to claim 1, comprising injection blow molding.

24. The method for manufacturing a multilayer vessel of claim 23, the method comprising:
molding a multilayer preform by individually injecting the layer (X) that contains a cycloolefin-based polymer (B) as a major ingredient, and the layer (Y) that contains the polyamide resin (A) as a major ingredient, to thereby form a multilayer preform; and,
molding the multilayer preform by blow molding, wherein
the polyamide resin (A) is composed of a structural unit derived from diamine and a structural unit derived from dicarboxylic acid,
70 mol % or more of the structural unit derived from diamine is derived from metaxylylenediamine, and
30 to 60 mol % of the structural unit derived from dicarboxylic acid is derived from a straight chain aliphatic α,ω-dicarboxylic acid having 4 to 20 carbon atoms, and 70 to 40 mol % is derived from isophthalic acid.

25. The method for manufacturing a multilayer vessel of claim 24, wherein the polyamide resin (A) contains 20 to 200 ppm by mass of phosphorus atom, and contains calcium atom so that the molar ratio given by (phosphorus atom):(calcium atom) will be 1:0.3 to 0.7.

26. The method for manufacturing a multilayer vessel of claim 11, the method comprising:
conducting direct blow molding, using
a material that composes the layer (X) containing the cycloolefin-based polymer (B) as a major ingredient;
a material that composes the adhesive layer; and,
a material that composes the layer (Y) containing the polyamide resin (A) as the major ingredient,
the polyamide resin (A) is composed of a structural unit derived from diamine and a structural unit derived from dicarboxylic acid, 70 mol % or more of the structural unit derived from diamine is derived from metaxylylenediamine, and
30 to 60 mol % of the structural unit derived from dicarboxylic acid is derived from a straight chain aliphatic α,ω-dicarboxylic acid having 4 to 20 carbon atoms, and 70 to 40 mol % is derived from isophthalic acid.

* * * * *

UNITED STATES PATENT AND TRADEMARK OFFICE
CERTIFICATE OF CORRECTION

PATENT NO. : 11,911,341 B2
APPLICATION NO. : 16/077640
DATED : February 27, 2024
INVENTOR(S) : S. Arakawa et al.

It is certified that error appears in the above-identified patent and that said Letters Patent is hereby corrected as shown below:

On the Title Page

Page 2/other publications (Line 3), please change "pharma ceuticals" to -- pharmaceuticals --.

In the Claims

Column 76, Line 61 (Claim 1, Line 23), please change "Pa sec" to -- Pa.sec --.
Column 76, Line 65 (Claim 1, Line 27), please change "Pa sec" to -- Pa.sec --.
Column 77, Line 6 (Claim 4, Line 2), please change "the a" to -- the --.
Column 78, Line 16 (Claim 20, Line 23), please change "Pa sec" to -- Pa.sec --.
Column 78, Line 20 (Claim 20, Line 27), please change "Pa sec" to -- Pa.sec --.

Signed and Sealed this
Thirteenth Day of August, 2024

Katherine Kelly Vidal
*Director of the United States Patent and Trademark Office*